US010208096B2

(12) United States Patent
Sasaki et al.

(10) Patent No.: US 10,208,096 B2
(45) Date of Patent: Feb. 19, 2019

(54) FUNCTION SUPPRESSION TYPE OF GENETICALLY-MODIFIED RHODOCYTIN MUTANT

(71) Applicant: UNIVERSITY OF YAMANASHI, Yamanashi (JP)

(72) Inventors: Tomoyuki Sasaki, Yamanashi (JP); Toshiaki Shirai, Yamanashi (JP); Katsue Inoue, Yamanashi (JP)

(73) Assignee: University of Yamanashi, Yamanashi (JP)

( * ) Notice: Subject to any disclaimer, the term of this patent is extended or adjusted under 35 U.S.C. 154(b) by 0 days.

(21) Appl. No.: 15/590,268

(22) Filed: May 9, 2017

(65) Prior Publication Data
US 2017/0320924 A1    Nov. 9, 2017

(30) Foreign Application Priority Data

May 9, 2016    (JP) ................. 2016-094203

(51) Int. Cl.
*C07K 14/00* (2006.01)
*A61K 38/00* (2006.01)
*C07K 14/46* (2006.01)
*C07K 14/705* (2006.01)

(52) U.S. Cl.
CPC .......... *C07K 14/46* (2013.01); *C07K 14/7056* (2013.01); *A61K 38/00* (2013.01)

(58) Field of Classification Search
CPC ................. C07K 14/46; A61K 38/00
See application file for complete search history.

(56) References Cited

U.S. PATENT DOCUMENTS

2014/0363423 A1* 12/2014 Huang ................. C07K 14/705
424/133.1

OTHER PUBLICATIONS

Chang et al., 2014, Inhibitory effects of polypeptides derived from a snake venom C-type lectin, aggretin, on tumor cell-induced platelet aggregation, Journal of Thrombosis and Haemostasis, 12: 540-549.*
Bruserud, 2013, The Snake Venom Rhodocytin from Calloselasma rhodostoma—A Clinically Important Toxin and a Useful Expermental Tool for Studies of C-Type Lectin-like Receptor 2 (CLEC-2), Toxins, 5: 665-674.*
Chung et al., 2001, Aggretin, a C-type Lectin Protein, Induces Platelet Aggregation via Integrin alpha2beta1 and GPIb in a Phosphatidylinositol 3-Kinase Independent Pathway, Biochemical and Biophysical Research Communications, 285: 689-695.*
Chung et al., 2004, Aggretin, a snake venom-derived endothelial integrin alpha2beta1 agonist, induces angiogenesis via expression of vascular endothelial growth factor, Blood, 103(6): 2105-2113.*
Watson et al., 2011, Molecular Analysis of the Interaction of the Snake Venom Rhodocytin with the Platelet Receptor CLEC-2, Toxins, 3: 991-1003.*
Yongchol Shin et al., "Rhodocytin, a Functional Novel Platelet Agonist Belonging to the Heterodimeric C-Type Lectin Family, Induces Platelet Aggregation Independently of Glycoprotein Ib", Biochem Biophys Res Commun. Apr. 28, 1998;245(3):741-5., 5 pgs.
Katsue Suzuki-Inoue et al., "A novel Syk-dependent mechanism of platelet activation by the C-type lectin receptor CLEC-2", Blood. Jan. 15, 2006;107(2):542-9. Epub Sep. 20, 2005., 9 pgs.
Elizabeth Hooley et al., "The Crystal Structure of the Platelet Activator Aggretin Reveals a Novel (αβ)2 Dimeric Structure", Biochemistry. Jul. 29, 2008;47(30)7831-7. doi: 1021/bi8005 28t. Epub Jul. 3, 2008. 10., 7 pgs.
Ching-Hu Chung et al., "Molecular Cloning and Sequence Analysis of Aggretin, a Collagen-like Platelet Aggregation Inducer", Biochem Biophys Res Commun. Oct. 5, 1999;263(3):723-7., 5 pgs.

* cited by examiner

*Primary Examiner* — Amber D Steele
(74) *Attorney, Agent, or Firm* — Maier & Maier, PLLC

(57) ABSTRACT

According to the present invention, a mutant rhodocytin lacking platelet aggregation ability is provided. According to the present invention, a pharmaceutical composition including a mutant rhodocytin lacking platelet aggregation ability is provided. According to the present invention, there is provided a method for inhibiting platelet aggregation by a platelet aggregating substance, including administering a pharmaceutical composition including a mutant rhodocytin lacking platelet aggregation ability to a subject in need thereof.

12 Claims, 21 Drawing Sheets

Specification includes a Sequence Listing.

Human platelet (TS): 100uL 20x10⁴PLT/uL
Agonist: 11.1uL medium
Monitor: 10min

Human platelet (TS): 20uL 100x10⁴PLT/uL
Inhibitor: 80uL medium
Incubation for 5min
Agonist: 11.1uL WT rhodocytin medium (x1)
Monitor: 10min
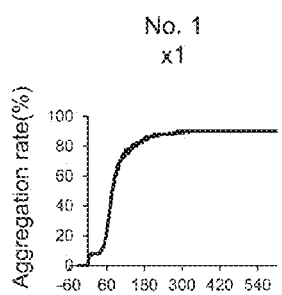
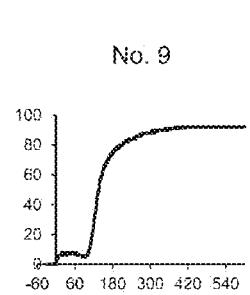
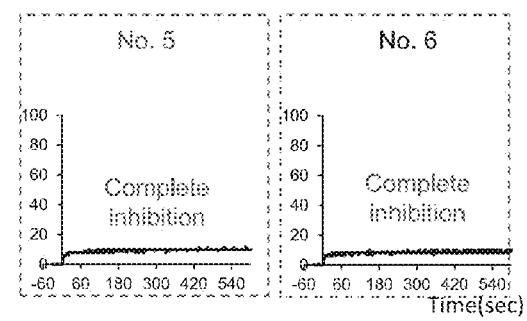
Fig.9A   Fig.9B   Fig.9C   Fig.9D
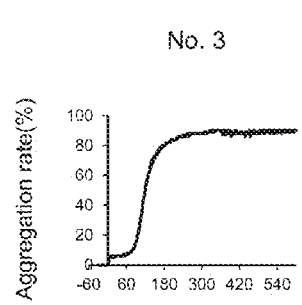
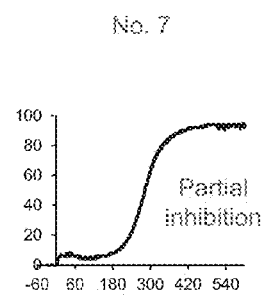
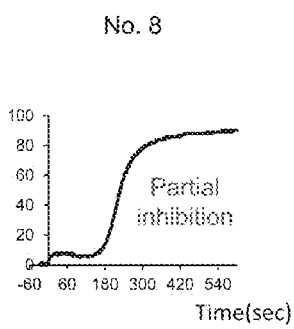
Fig.9E   Fig.9F   Fig.9G Platelets: Human
Agonist: 10 nM Rhodocytin Platelets: Human
Agonist: 2 μg/mL Collagen Tumor occupancy was measured by the ratio of tumor area over total area of the lungs.
n = 5 nude mouse in each groups. Scale bar, 500 μm.

[βS]-[α subunit](SEQ ID NO: 42)

ATGGGCCGGTTTATCTTCGTGAGCTTTGGCCTGCTGGTGGTGTTCCTGAGCCTGTCCGGCACAGGCGC
TGGACTGGAGGACTGCGACTTCGGCTGGTCCCCCTACGACCAGCACTGCTACCAGGCCTTCAACGAGC
AGAAGACCTGGGACGAGGCCGAGAAGTTCTGCAGGGCTCAGGAGAACGGCGCCCATCTGGCCAGCATC
GAGTCCAACGGCGAGGCCGACTTCGTGAGCTGGCTCATCAGCCAGAAGGACGAGCTGGCCGACGAGGA
CTACGTGTGGATCGGCCTGAGGGCTCAGAACAAGGAGCAGCAGTGCTCCTCCGAGTGGTCCGACGGCA
GCTCCGTGTCCTACGAGAACCTGATCGACCTGCACACCAAGAAGTGCGGCGCCCTGGAGAAGCTGACC
GGCTTTCGGAAGTGGGTGAACTACTACTGCGAGCAGATGCACGCCTTCGTGTGCAAGCTGCTGCCCTA
CTGA

Underline: signal sequence

Fig.20A

[βS]-[β subunit] (SEQ ID NO: 2)

ATGGGCCGGTTCATCTTCGTGTCCTTCGGCCTGCTGGTGGTGTTCCTGAGCCTGTCCGGAACAGGCGC
CGACTGTCCTTCCGGCTGGTCCTCCTACGAGGGCCACTGCTACAAGCCCTTTAACGAGCCCAAGAACT
GGGCTGACGCCGAGCGGTTCTGCAAGCTGCAGCCCAAGCACTCCCACCTCGTGAGCTTCCAGTCCGCC
GAGGAGGCCGACTTCGTGGTGAAGCTGACCAGGCCCAGGCTGAAGGCCAACCTGGTGTGGATGGGCCT
GTCCAACATCTGGCACGGCTGTAACTGGCAGTGGTCCGACGGCGCCAGGCTGAACTACAAGGACTGGC
AGGAGCAGTCCGAGTGTCTGGCCTTCAGGGGCGTGCACACCGAGTGGCTGAACATGGACTGCTCCTCC
ACCTGCTCCTTCGTGTGCAAGTTCAAGGCCTGA

Underline: signal sequence

Fig.20B

[βS]-[β subunit] (R28A and K31A) (SEQ ID NO: 43)

ATGGGCCGGTTCATCTTCGTGTCCTTCGGCCTGCTGGTGGTGTTCCTGAGCCTGTCCGGAACAGGCGC
CGACTGTCCTTCCGGCTGGTCCTCCTACGAGGGCCACTGCTACAAGCCCTTTAACGAGCCCAAGAACT
GGGCTGACGCCGAGGCGTTCTGCGCGCTGCAGCCCAAGCACTCCCACCTCGTGAGCTTCCAGTCCGCC
GAGGAGGCCGACTTCGTGGTGAAGCTGACCAGGCCCAGGCTGAAGGCCAACCTGGTGTGGATGGGCCT
GTCCAACATCTGGCACGGCTGTAACTGGCAGTGGTCCGACGGCGCCAGGCTGAACTACAAGGACTGGC
AGGAGCAGTCCGAGTGTCTGGCCTTCAGGGGCGTGCACACCGAGTGGCTGAACATGGACTGCTCCTCC
ACCTGCTCCTTCGTGTGCAAGTTCAAGGCCTGA

<div style="text-align:right">
Underline: signal sequence<br>
Box: Mutation sites
</div>

Fig.20C

[βS]-[β subunit] (R56A) (SEQ ID NO: 44)

ATGGGCCGGTTCATCTTCGTGTCCTTCGGCCTGCTGGTGGTGTTCCTGAGCCTGTCCGGAACAGGCGC
CGACTGTCCTTCCGGCTGGTCCTCCTACGAGGGCCACTGCTACAAGCCCTTTAACGAGCCCAAGAACT
GGGCTGACGCCGAGCGGTTCTGCAAGCTGCAGCCCAAGCACTCCCACCTCGTGAGCTTCCAGTCCGCC
GAGGAGGCCGACTTCGTGGTGAAGCTGACCGCGCCCAGGCTGAAGGCCAACCTGGTGTGGATGGGCCT
GTCCAACATCTGGCACGGCTGTAACTGGCAGTGGTCCGACGGCGCCAGGCTGAACTACAAGGACTGGC
AGGAGCAGTCCGAGTGTCTGGCCTTCAGGGGCGTGCACACCGAGTGGCTGAACATGGACTGCTCCTCC
ACCTGCTCCTTCGTGTGCAAGTTCAAGGCCTGA

<div style="text-align:right">
Underline: signal sequence<br>
Box: Mutation sites
</div>

Fig.20D

[βS]-[β subunit] (K53A and R56A) (SEQ ID NO: 45)

ATGGGCCGGTTCATCTTCGTGTCCTTCGGCCTGCTGGTGGTGTTCCTGAGCCTGTCCGGAACAGGCGC
CGACTGTCCTTCCGGCTGGTCCTCCTACGAGGGCCACTGCTACAAGCCCTTTAACGAGCCCAAGAACT
GGGCTGACGCCGAGCGGTTCTGCAAGCTGCAGCCCAAGCACTCCCACCTCGTGAGCTTCCAGTCCGCC
GAGGAGGCCGACTTCGTGGTGGCGCTGACCGCGCCCAGGCTGAAGGCCAACCTGGTGTGGATGGGCCT
GTCCAACATCTGGCACGGCTGTAACTGGCAGTGGTCCGACGGCGCCAGGCTGAACTACAAGGACTGGC
AGGAGCAGTCCGAGTGTCTGGCCTTCAGGGGCGTGCACACCGAGTGGCTGAACATGGACTGCTCCTCC
ACCTGCTCCTTCGTGTGCAAGTTCAAGGCCTGA

Underline: signal sequence
Box: Mutation sites

Fig.20E

[βS]-[β subunit] (R58A and K60A) (SEQ ID NO: 46)

ATGGGCCGGTTCATCTTCGTGTCCTTCGGCCTGCTGGTGGTGTTCCTGAGCCTGTCCGGAACAGGCGC
CGACTGTCCTTCCGGCTGGTCCTCCTACGAGGGCCACTGCTACAAGCCCTTTAACGAGCCCAAGAACT
GGGCTGACGCCGAGCGGTTCTGCAAGCTGCAGCCCAAGCACTCCCACCTCGTGAGCTTCCAGTCCGCC
GAGGAGGCCGACTTCGTGGTGAAGCTGACCAGGCCCGCGCTGGCGGCCAACCTGGTGTGGATGGGCCT
GTCCAACATCTGGCACGGCTGTAACTGGCAGTGGTCCGACGGCGCCAGGCTGAACTACAAGGACTGGC
AGGAGCAGTCCGAGTGTCTGGCCTTCAGGGGCGTGCACACCGAGTGGCTGAACATGGACTGCTCCTCC
ACCTGCTCCTTCGTGTGCAAGTTCAAGGCCTGA

Underline: signal sequence
Box: Mutation sites

Fig.20F

[βS]-[β subunit] (R28A, K31A, K53A and R56A) (SEQ ID NO: 47)

<u>ATGGGCCGGTTCATCTTCGTGTCCTTCGGCCTGCTGGTGGTGTTCCTGAGCCTGTCCGGAACAGGCGC</u>
<u>C</u>GACTGTCCTTCCGGCTGGTCCTCCTACGAGGGCCACTGCTACAAGCCCTTTAACGAGCCCAAGAACT
GGGCTGACGCCGAG<span style="border:1px solid">GC</span>GTTCTGC<span style="border:1px solid">GC</span>GCTGCAGCCCAAGCACTCCCACCTCGTGAGCTTCCAGTCCGCC
GAGGAGGCCGACTTCGTGGT<span style="border:1px solid">GC</span>GCTGACC<span style="border:1px solid">GC</span>GCCCAGGCTGAAGGCCAACCTGGTGTGGATGGGCCT
GTCCAACATCTGGCACGGCTGTAACTGGCAGTGGTCCGACGGCGCCAGGCTGAACTACAAGGACTGGC
AGGAGCAGTCCGAGTGTCTGGCCTTCAGGGGCGTGCACACCGAGTGGCTGAACATGGACTGCTCCTCC
ACCTGCTCCTTCGTGTGCAAGTTCAAGGCCTGA Underline: signal sequence
Box: Mutation sites

Fig.20G

[βS]-[β subunit] (R28A, K31A, R58A and K60A) (SEQ ID NO: 48)

<u>ATGGGCCGGTTCATCTTCGTGTCCTTCGGCCTGCTGGTGGTGTTCCTGAGCCTGTCCGGAACAGGCGC</u>
<u>C</u>GACTGTCCTTCCGGCTGGTCCTCCTACGAGGGCCACTGCTACAAGCCCTTTAACGAGCCCAAGAACT
GGGCTGACGCCGAG<span style="border:1px solid">GC</span>GTTCTGC<span style="border:1px solid">GC</span>GCTGCAGCCCAAGCACTCCCACCTCGTGAGCTTCCAGTCCGCC
GAGGAGGCCGACTTCGTGGTGAAGCTGACCAGGCC<span style="border:1px solid">GC</span>GCTG<span style="border:1px solid">GC</span>GGCCAACCTGGTGTGGATGGGCCT
GTCCAACATCTGGCACGGCTGTAACTGGCAGTGGTCCGACGGCGCCAGGCTGAACTACAAGGACTGGC
AGGAGCAGTCCGAGTGTCTGGCCTTCAGGGGCGTGCACACCGAGTGGCTGAACATGGACTGCTCCTCC
ACCTGCTCCTTCGTGTGCAAGTTCAAGGCCTGA Underline: signal sequence
Box: Mutation sites

Fig.20H

SEQUENCE LISTING

```
<160> NUMBER OF SEQ ID NOS: 48

<210> SEQ ID NO 1
<211> LENGTH: 504
<212> TYPE: DNA
<213> ORGANISM: Artificial Sequence
<220> FEATURE:
<223> OTHER INFORMATION: Designed Base Sequence based on Signal sequence
      of Rhodocytin beta subunit and Rhodocytin alpha subunit gene.

<400> SEQUENCE: 1
atgggccggt ttatcttcgt gagctttggc ctgctggtgg tgttcctgag cctgtccggc      60
acaggcgcta tcaggcacga gggcaccagg gctggactgg aggactgcga cttcggctgg     120 tcccctacg accagcactg ctaccaggcc ttcaacgagc agaagacctg ggacgaggcc      180
gagaagttct gcagggctca ggagaacggc gcccatctgg ccagcatcga gtccaacggc     240
gaggccgact tcgtgagctg gctcatcagc cagaaggacg agctggccga cgaggactac     300
gtgtggatcg gcctgagggc tcagaacaag gagcagcagt gctcctccga gtggtccgac     360
ggcagctccg tgtcctacga gaacctgatc gacctgcaca ccaagaagtg cggcgccctg     420
gagaagctga ccggctttcg gaagtgggtg aactactact gcgagcagat gcacgccttc     480
```

```
gtgtgcaagc tgctgcccta ctga                                            504
```

```
<210> SEQ ID NO 2
<211> LENGTH: 441
<212> TYPE: DNA
<213> ORGANISM: Artificial Sequence
<220> FEATURE:
<223> OTHER INFORMATION: Designed Base Sequence based on Signal sequence
      of Rhodocytin beta subunit and Rhodocytin beta subunit gene.

<400> SEQUENCE: 2
atgggccggt tcatcttcgt gtccttcggc ctgctggtgg tgttcctgag cctgtccgga    60
acaggcgccg actgtccttc cggctggtcc tcctacgagg ccactgctca aagcccttt    120 aacgagccca gaactgggc tgacgccgag cggttctgca agctgcagcc caagcactcc    180
cacctcgtga gcttccagtc cgccgaggag gccgacttcg tggtgaagct gaccaggccc    240
aggctgaagg ccaacctggt gtggatgggc ctgtccaaca tctggcacgg ctgtaactgg    300
cagtggtccg acggcgccag gctgaactac aaggactggc aggagcagtc cgagtgtctg    360
gccttcaggg gcgtgcacac cgagtggctg aacatggact gctcctccac ctgctccttc    420
gtgtgcaagt tcaaggcctg a                                              441
```

```
<210> SEQ ID NO 3
<211> LENGTH: 480
<212> TYPE: DNA
<213> ORGANISM: Artificial Sequence
<220> FEATURE:
<223> OTHER INFORMATION: Designed Base Sequence based on Signal sequence
      of Rhodocytin beta subunit and Rhodocytin alpha subunit gene.

<400> SEQUENCE: 3
atggggcgat tcatcttcgt gagcttcggc ttgctggtcg tgttcctctc cctgagtggt    60
actggagctg gtttggagga ttgtgacttt ggttggtctc cctatgatca gcattgctac    120
caggcattca atgaacaaaa aacctgggat gaggcagaga agttctgcag gcgcaggag    180 aatggtgcgc atctggcctc tatcgaaagc aatggagaag cagactttgt tcctggctg    240 atttctcaga aagacgaact ggcagacgaa gactacgtct ggatcggact gagggctcaa    300
aacaaagaac agcaatgcag ctcggagtgg agcgatggct ccagtgtcag ttatgagaac    360
ttgattgatc tacatacgaa aaagtgtggt gcgctggaaa aactgacagg gtttcgtaag    420
tgggtcaatt attactgtga acaaatgcat gctttcgtct gcaagctcct gccatattaa    480
```

```
<210> SEQ ID NO 4
<211> LENGTH: 441
<212> TYPE: DNA
<213> ORGANISM: Calloselasma rhodostoma

<400> SEQUENCE: 4
atggggcgat tcatcttcgt gagcttcggc ttgctggtcg tgttcctctc cctgagtggt    60
actggagctg attgtccctc tggttggtcc tcctatgaag gcattgctca aagcccttc    120 aatgaaccga aaactgggc cgatgcagag agattctgca aactgcagcc gaagcacagc    180
catctggtct cctttcagag cgctgaagaa gcagattttg tggtcaagtt gaccagacca    240
aggttgaaag ccaatttagt ctggatggga ctgagcaata tctggcacgg atgcaactgg    300
cagtggagtg atggcgccag gctcaactac aaagactggc aggaacaatc tgaatgtctc    360
gcattcaggg gagttcatac agaatggtta aatatggact gcagcagtac ttgctctttc    420
gtctgcaagt tcaaggcata g                                              441
```

<210> SEQ ID NO 5
<211> LENGTH: 4178
<212> TYPE: DNA
<213> ORGANISM: Artificial Sequence
<220> FEATURE:
<223> OTHER INFORMATION: Recombinant vector

<400> SEQUENCE: 5

| | | | | | |
|---|---|---|---|---|---|
| gagttcgagc | ttgcatgcct | gcaggtcgtt | acataactta | cggtaaatgg | cccgcctggc | 60 |
| tgaccgccca | acgacccccg | cccattgacg | tcaataatga | cgtatgttcc | catagtaacg | 120 |
| ccaataggga | ctttccattg | acgtcaatgg | gtggagtatt | tacggtaaac | tgcccacttg | 180 |
| gcagtacatc | aagtgtatca | tatgccaagt | acgcccccta | ttgacgtcaa | tgacggtaaa | 240 |
| tggcccgcct | ggcattatgc | ccagtacatg | accttatggg | actttcctac | ttggcagtac | 300 |
| atctacgtat | tagtcatcgc | tattaccatg | gtgatgcggt | tttggcagta | catcaatggg | 360 |
| cgtggatagc | ggtttgactc | acggggattt | ccaagtctcc | accccattga | cgtcaatggg | 420 |
| agtttgtttt | ggcaccaaaa | tcaacgggac | tttccaaaat | gtcgtaacaa | ctccgcccca | 480 |
| ttgacgcaaa | tgggcggtag | gcgtgtacgg | tgggaggtct | atataagcag | agctcgttta | 540 |
| gtgaaccgtc | agatcgcctg | gagacgccat | ccacgctgtt | ttgacctcca | tagaagacac | 600 |
| cgggaccgat | ccagcctccg | gactctagag | gatccggtac | tagaggaact | gaaaaaccag | 660 |
| aaagttaact | ggtaagttta | gtcttttttgt | cttttatttc | aggtcccgga | tccggtggtg | 720 |
| gtgcaaatca | aagaactgct | cctcagtgga | tgttgccttt | acttctaggc | ctgtacggaa | 780 |
| gtgttacttc | tgctctaaaa | gctgcggaat | tgtacccgcg | gcccaccat | ggcatcaatg | 840 |
| ggccggttta | tcttcgtgag | ctttggcctg | ctggtggtgt | tcctgagcct | gtccggcaca | 900 |
| ggcgctggac | tggaggactg | cgacttcggc | tggtccccct | acgaccagca | ctgctaccag | 960 |
| gccttcaacg | agcagaagac | ctgggacgag | gccgagaagt | tctgcagggc | tcaggagaac | 1020 |
| ggcgcccatc | tggccagcat | cgagtccaac | ggcgaggccg | acttcgtgag | ctggctcatc | 1080 |
| agccagaagg | acgagctggc | cgacgaggac | tacgtgtgga | tcggcctgag | ggctcagaac | 1140 |
| aaggagcagc | agtgctcctc | cgagtggtcc | gacggcagcc | ccgtgtccta | cgagaacctg | 1200 |
| atcgacctgc | acaccaagaa | gtgcggcgcc | ctggagaagc | tgaccggctt | cggaagtgg | 1260 |
| gtgaactact | actgcgagca | gatgcacgcc | ttcgtgtgca | agctgctgcc | ctactgaatc | 1320 |
| cagacatgat | aagatacatt | gatgagtttg | gacaaaccac | aactagaatg | cagtgaaaaa | 1380 |
| aatgctttat | ttgtgaaatt | tgtgatgcta | ttgctttatt | tgtaaccatt | ataagctgca | 1440 |
| ataaacaagt | taacaacaac | aattgcattc | attttatgtt | tcaggttcag | ggggaggtgt | 1500 |
| gggaggtttt | ttcggatcct | ctagagtcga | tctgcaggca | tgctagcttg | gcgtaatcat | 1560 |
| ggtcatagct | gtttcctgtg | tgaaattgtt | atccgctcac | aattccacac | aacatacgag | 1620 |
| ccggaagcat | aaagtgtaaa | gcctggggtg | cctaatgagt | gagctaactc | acattaattg | 1680 |
| cgttgcgctc | actgcccgct | ttccagtcgg | gaaacctgtc | gtgccagctg | cattaatgaa | 1740 |
| tcggccaacg | cgcggggaga | ggcggtttgc | gtattgggcg | ctcttccgct | tcctcgctca | 1800 |
| ctgactcgct | gcgctcggtc | gttcggctgc | ggcgagcgg | atcagctcac | tcaaaggcgg | 1860 |
| taatacggtt | atccacagaa | tcaggggata | acgcaggaaa | gaacatgtga | gcaaaaggcc | 1920 |
| agcaaaaggc | caggaaccgt | aaaaaggccg | cgttgctggc | gtttttccat | aggctccgcc | 1980 |
| cccctgacga | gcatcacaaa | aatcgacgct | caagtcagag | gtggcgaaac | ccgacaggac | 2040 |

| | |
|---|---|
| tataaagata ccaggcgttt cccctggaa gctccctcgt gcgctctcct gttccgaccc | 2100 |
| tgccgcttac cggataccctg tccgcctttc tcccttcggg aagcgtggcg ctttctcata | 2160 |
| gctcacgctg taggtatctc agttcggtgt aggtcgttcg ctccaagctg ggctgtgtgc | 2220 |
| acgaacccccc cgttcagccc gaccgctgcg ccttatccgg taactatcgt cttgagtcca | 2280 |
| acccggtaag cacgactta tcgccactgg cagcagccac tggtaacagg attagcagag | 2340 |
| cgaggtatgt aggcggtgct acagagttct gaagtggtg gcctaactac ggctacacta | 2400 |
| gaaggacagt atttggtatc tgcgctctgc tgaagccagt taccttcgga aaaagagttg | 2460 |
| gtagctcttg atccggcaaa caaaccaccg ctggtagcgg tggtttttt gtttgcaagc | 2520 |
| agcagattac gcgcagaaaa aaaggatctc aagaagatcc tttgatcttt tctacggggt | 2580 |
| ctgacgctca gtggaacgaa aactcacgtt aagggatttt ggtcatgaga ttatcaaaaa | 2640 |
| ggatcttcac ctagatcctt ttaaattaaa aatgaagttt taaatcaatc taaagtatat | 2700 |
| atgagtaaac ttggtctgac agttaccaat gcttaatcag tgaggcacct atctcagcga | 2760 |
| tctgtctatt tcgttcatcc atagttgcct gactccccgt cgtgtagata actacgatac | 2820 |
| gggagggctt accatctggc cccagtgctg caatgatacc gcgagaccca cgctcaccgg | 2880 |
| ctccagattt atcagcaata aaccagccag ccggaagggc cgagcgcaga agtggtcctg | 2940 |
| caactttatc cgcctccatc cagtctatta attgttgccg ggaagctaga gtaagtagtt | 3000 |
| cgccagttaa tagtttgcgc aacgttgttg ccattgctac aggcatcgtg gtgtcacgct | 3060 |
| cgtcgtttgg tatggcttca ttcagctccg gttcccaacg atcaaggcga gttacatgat | 3120 |
| cccccatgtt gtgcaaaaaa gcggttagct ccttcggtcc tccgatcgtt gtcagaagta | 3180 |
| agttggccgc agtgttatca ctcatggtta tggcagcact gcataattct cttactgtca | 3240 |
| tgccatccgt aagatgcttt tctgtgactg gtgagtactc aaccaagtca ttctgagaat | 3300 |
| agtgtatgcg gcgaccgagt tgctcttgcc cggcgtcaat acgggataat accgcgccac | 3360 |
| atagcagaac tttaaaagtg ctcatcattg gaaaacgttc ttcggggcga aaactctcaa | 3420 |
| ggatcttacc gctgttgaga tccagttcga tgtaacccac tcgtgcaccc aactgatctt | 3480 |
| cagcatcttt tactttcacc agcgtttctg ggtgagcaaa aacaggaagg caaaatgccg | 3540 |
| caaaaaaggg aataagggcg acacggaaat gttgaatact catactcttc cttttcaat | 3600 |
| attattgaag catttatcag ggttattgtc tcatgagcgg atacatattt gaatgtattt | 3660 |
| agaaaaataa acaaataggg gttccgcgca catttccccg aaaagtgcca cctgacgtct | 3720 |
| aagaaaccat tattatcatg acattaacct ataaaaatag gcgtatcacg aggccctttc | 3780 |
| gtctcgcgcg tttcggtgat gacggtgaaa acctctgaca catgcagctc ccggagacgg | 3840 |
| tcacagcttg tctgtaagcg gatgccggga gcagacaagc ccgtcagggc gcgtcagcgg | 3900 |
| gtgttggcgg gtgtcggggc tggcttaact atgcggcatc agagcagatt gtactgagag | 3960 |
| tgcaccatat gcggtgtgaa ataccgcaca gatgcgtaag gagaaaatac cgcatcaggc | 4020 |
| gccattcgcc attcaggctg cgcaactgtt gggaagggcg atcggtgcgg gcctcttcgc | 4080 |
| tattacgcca gctggcgaaa gggggatgtg ctgcaaggcg attaagttgg gtaacgccag | 4140 |
| ggttttccca gtcacgacgt tgtaaaacga cggccagt | 4178 |

<210> SEQ ID NO 6
<211> LENGTH: 4202
<212> TYPE: DNA
<213> ORGANISM: Artificial Sequence
<220> FEATURE:
<223> OTHER INFORMATION: Recombinant vector

<400> SEQUENCE: 6

```
gagttcgagc ttgcatgcct gcaggtcgtt acataactta cggtaaatgg cccgcctggc    60
tgaccgccca acgaccccg cccattgacg tcaataatga cgtatgttcc catagtaacg    120
ccaataggga ctttccattg acgtcaatgg gtggagtatt tacggtaaac tgcccacttg    180
gcagtacatc aagtgtatca tatgccaagt acgccccta ttgacgtcaa tgacggtaaa    240
tggcccgcct ggcattatgc ccagtacatg accttatggg actttcctac ttggcagtac    300
atctacgtat tagtcatcgc tattaccatg gtgatgcggt tttggcagta catcaatggg    360
cgtggatagc ggtttgactc acggggattt ccaagtctcc accccattga cgtcaatggg    420
agtttgtttt ggcaccaaaa tcaacgggac tttccaaaat gtcgtaacaa ctccgcccca    480
ttgacgcaaa tgggcggtag gcgtgtacgg tgggaggtct atataagcag agctcgttta    540
gtgaaccgtc agatcgcctg gagacgccat ccacgctgtt tgacctccaa tagaagacac    600
cgggaccgat ccagcctccg gactctagag gatccggtac tagaggaact gaaaaaccag    660
aaagttaact ggtaagttta gtcttttttgt cttttatttc aggtcccgga tccggtggtg    720
gtgcaaatca agaactgct cctcagtgga tgttgccttt acttctaggc ctgtacggaa    780
gtgttacttc tgctctaaaa gctgcggaat tgtacccgcg ggcccaccat ggcatcaatg    840
ggccggttta tcttcgtgag cttttggcctg ctggtggtgt tcctgagcct gtccggcaca    900
ggcgctatca ggcacgaggg caccagggct ggactggagg actgcgactt cggctggtcc    960
ccctacgacc agcactgcta ccaggccttc aacgagcaga gacctgggac gaggccgag   1020
aagttctgca gggctcagga gaacggcgcc catctggcca gcatcgagtc caacggcgag   1080
gccgacttcg tgagctggct catcagccag aaggacgagc tggccgacga ggactacgtg   1140
tggatcggcc tgagggctca gaacaaggag cagcagtgct cctccgagtg gtccgacggc   1200
agctccgtgt cctacgagaa cctgatcgac ctgcacacca gaagtgcgg cgccctggag   1260
aagctgaccg gctttcggaa gtgggtgaac tactactgcg agcagatgca cgccttcgtg   1320
tgcaagctgc tgccctactg aatccagaca tgataagata cattgatgag tttggacaaa   1380
ccacaactag aatgcagtga aaaaaatgct ttatttgtga aatttgtgat gctattgctt   1440
tatttgtaac cattataagc tgcaataaac aagttaacaa caacaattgc attcatttta   1500
tgtttcaggt tcaggggag gtgtgggagg ttttttcgga tcctctagag tcgatctgca   1560
ggcatgctag cttggcgtaa tcatggtcat agctgtttcc tgtgtgaaat tgttatccgc   1620
tcacaattcc acacaacata cgagccggaa gcataaagtg taaagcctgg ggtgcctaat   1680
gagtgagcta actcacatta attgcgttgc gctcactgcc cgctttccag tcgggaaacc   1740
tgtcgtgcca gctgcattaa tgaatcggcc aacgcgcggg gagaggcggt ttgcgtattg   1800
ggcgctcttc cgcttcctcg ctcactgact cgctgcgctc ggtcgttcgg ctgcggcgag   1860
cggtatcagc tcactcaaag gcggtaatac ggttatccac agaatcaggg gataacgcag   1920
gaaagaacat gtgagcaaaa ggccagcaaa aggccaggaa ccgtaaaaag gccgcgttgc   1980
tggcgttttt ccataggctc cgcccccctg acgagcatca aaaaatcga cgctcaagtc   2040
agaggtggcg aaacccgaca ggactataaa gataccaggc gtttccccct ggaagctccc   2100
tcgtgcgctc tcctgttccg accctgccgc ttaccggata cctgtccgcc tttctccctt   2160
cgggaagcgt ggcgctttct catagctcac gctgtaggta tctcagttcg gtgtaggtcg   2220
ttcgctccaa gctgggctgt gtgcacgaac cccccgttca gcccgaccgc tgcgccttat   2280
```

| | |
|---|---|
| ccggtaacta tcgtcttgag tccaacccgg taagacacga cttatcgcca ctggcagcag | 2340 |
| ccactggtaa caggattagc agagcgaggt atgtaggcgg tgctacagag ttcttgaagt | 2400 |
| ggtggcctaa ctacggctac actagaagga cagtatttgg tatctgcgct ctgctgaagc | 2460 |
| cagttacctt cggaaaaaga gttggtagct cttgatccgg caaacaaacc accgctggta | 2520 |
| gcggtggttt ttttgtttgc aagcagcaga ttacgcgcag aaaaaaagga tctcaagaag | 2580 |
| atcctttgat cttttctacg gggtctgacg ctcagtggaa cgaaaactca cgttaaggga | 2640 |
| ttttggtcat gagattatca aaaaggatct tcacctagat ccttttaaat taaaaatgaa | 2700 |
| gttttaaatc aatctaaagt atatatgagt aaacttggtc tgacagttac caatgcttaa | 2760 |
| tcagtgaggc acctatctca gcgatctgtc tatttcgttc atccatagtt gcctgactcc | 2820 |
| ccgtcgtgta gataactacg atacgggagg gcttaccatc tggccccagt gctgcaatga | 2880 |
| taccgcgaga cccacgctca ccggctccag atttatcagc aataaaccag ccagccggaa | 2940 |
| gggccgagcg cagaagtggt cctgcaactt tatccgcctc catccagtct attaattgtt | 3000 |
| gccgggaagc tagagtaagt agttcgccag ttaatagttt gcgcaacgtt gttgccattg | 3060 |
| ctacaggcat cgtggtgtca cgctcgtcgt ttggtatggc ttcattcagc tccggttccc | 3120 |
| aacgatcaag gcgagttaca tgatccccca tgttgtgcaa aaaagcggtt agctccttcg | 3180 |
| gtcctccgat cgttgtcaga agtaagttgg ccgcagtgtt atcactcatg gttatggcag | 3240 |
| cactgcataa ttctcttact gtcatgccat ccgtaagatg cttttctgtg actggtgagt | 3300 |
| actcaaccaa gtcattctga gaatagtgta tgcggcgacc gagttgctct tgcccggcgt | 3360 |
| caatacggga taataccgcg ccacatagca gaactttaaa agtgctcatc attggaaaac | 3420 |
| gttcttcggg gcgaaaactc tcaaggatct taccgctgtt gagatccagt tcgatgtaac | 3480 |
| ccactcgtgc acccaactga tcttcagcat cttttacttt caccagcgtt tctgggtgag | 3540 |
| caaaaacagg aaggcaaaat gccgcaaaaa agggaataag ggcgacacgg aaatgttgaa | 3600 |
| tactcatact cttccttttt caatattatt gaagcattta tcagggttat tgtctcatga | 3660 |
| gcggatacat atttgaatgt atttagaaaa ataaacaaat aggggttccg cgcacatttc | 3720 |
| cccgaaaagt gccacctgac gtctaagaaa ccattattat catgacatta acctataaaa | 3780 |
| ataggcgtat cacgaggccc tttcgtctcg cgcgtttcgg tgatgacggt gaaaacctct | 3840 |
| gacacatgca gctcccggag acggtcacag cttgtctgta agcggatgcc gggagcagac | 3900 |
| aagcccgtca gggcgcgtca gcgggtgttg gcgggtgtcg gggctggctt aactatgcgg | 3960 |
| catcagagca gattgtactg agagtgcacc atatgcggtg tgaaataccg cacagatgcg | 4020 |
| taaggagaaa ataccgcatc aggcgccatt cgccattcag gctgcgcaac tgttgggaag | 4080 |
| ggcgatcggt gcgggcctct tcgctattac gccagctggc gaaagggggga tgtgctgcaa | 4140 |
| ggcgattaag ttgggtaacg ccagggtttt cccagtcacg acgttgtaaa acgacggcca | 4200 |
| gt | 4202 |

<210> SEQ ID NO 7
<211> LENGTH: 4139
<212> TYPE: DNA
<213> ORGANISM: Artificial Sequence
<220> FEATURE:
<223> OTHER INFORMATION: Recombinant vector

<400> SEQUENCE: 7

| | |
|---|---|
| gagttcgagc ttgcatgcct gcaggtcgtt acataactta cggtaaatgg cccgcctggc | 60 |
| tgaccgccca acgacccccg cccattgacg tcaataatga cgtatgttcc catagtaacg | 120 |

```
ccaataggga ctttccattg acgtcaatgg gtggagtatt tacgtaaac tgcccacttg    180
gcagtacatc aagtgtatca tatgccaagt acgccccta ttgacgtcaa tgacggtaaa    240
tggcccgcct ggcattatgc ccagtacatg accttatggg actttcctac ttggcagtac    300
atctacgtat tagtcatcgc tattaccatg gtgatgcgt tttggcagta catcaatggg     360
cgtggatagc ggtttgactc acggggattt ccaagtctcc accccattga cgtcaatggg    420
agtttgtttt ggcaccaaaa tcaacgggac tttccaaaat gtcgtaacaa ctccgcccca    480
ttgacgcaaa tgggcggtag gcgtgtacgg tgggaggtct atataagcag agctcgttta    540
gtgaaccgtc agatcgcctg gagacgccat ccacgctgtt ttgacctcca tagaagacac    600
cgggaccgat ccagcctccg gactctagag gatccggtac tagaggaact gaaaaaccag    660
aaagttaact ggtaagttta gtcttttgt cttttatttc aggtcccgga tccggtggtg     720
gtgcaaatca aagaactgct cctcagtgga tgttgccttt acttctaggc ctgtacggaa    780
gtgttacttc tgctctaaaa gctgcggaat tgtaccgcg ggccaccat ggcatcaatg       840
ggccggttca tcttcgtgtc cttcggcctg ctggtggtgt tcctgagcct gtccggaaca    900
ggcgccgact gtccttccgg ctggtcctcc tacgagggcc actgctacaa gcccttaac     960
gagcccaaga actgggctga cgccgagcgg ttctgcaagc tgcagcccaa gcactccac     1020
ctcgtgagct ccagtccgc cgaggaggcc gacttcgtgg tgaagctgac caggcccagg    1080
ctgaaggcca actggtgtg gatgggcctg tccaacatct ggcacggctg taactggcag    1140
tggtccgacg gcgccaggct gaactacaag gactggcagg agcagtccga gtgtctggcc    1200
ttcagggcg tgcacaccga gtggctgaac atggactgct cctccacctg ctccttcgtg    1260
tgcaagttca aggcctgaat ccagacatga taagatacat tgatgagttt ggacaaacca    1320
caactagaat gcagtgaaaa aatgctttta tttgtgaaat ttgtgatgct attgctttat    1380
ttgtaaccat tataagctgc aataaacaag ttaacaacaa caattgcatt cattttatgt    1440
ttcaggttca gggggaggtg tgggaggttt tttcggatcc tctagagtcg atctgcaggc    1500
atgctagctt ggcgtaatca tggtcatagc tgtttcctgt gtgaaattgt tatccgctca    1560
caattccaca caacatacga gccggaagca taaagtgtaa agcctggggt gcctaatgag    1620
tgagctaact cacattaatt gcgttgcgct cactgcccgc tttccagtcg ggaaacctgt    1680
cgtgccagct gcattaatga atcggccaac gcgcggggag aggcggtttg cgtattgggc    1740
gctcttccgc ttcctcgctc actgactcgc tgcgctcggt cgttcggctg cggcgagcgg    1800
tatcagctca ctcaaaggcg gtaatacggt tatccacaga atcaggggat aacgcaggaa    1860
agaacatgtg agcaaaaggc cagcaaaagg ccaggaaccg taaaaaggcc gcgttgctgg    1920
cgttttccca taggctccgc cccctgacg agcatcacaa aaatcgacgc tcaagtcaga    1980
ggtggcgaaa cccgacagga ctataaagat accaggcgtt tccccctgga agctccctcg    2040
tgcgctctcc tgttccgacc ctgccgctta ccggatacct gtccgccttt ctcccttcgg    2100
gaagcgtggc gctttctcat agctcacgct gtaggtatct cagttcggtg taggtcgttc    2160
gctccaagct gggctgtgtg cacgaaccc ccgttcagcc cgaccgctgc gccttatccg     2220
gtaactatcg tcttgagtcc aacccggtaa gacacgactt atcgccactg gcagcagcca    2280
ctggtaacag gattagcaga gcgaggtatg taggcggtgc tacagagttc ttgaagtggt    2340
ggcctaacta cggctacact agaaggacag tatttggtat ctgcgctctg ctgaagccag    2400
ttaccttcgg aaaaagagtt ggtagctctt gatccggcaa acaaaccacc gctggtagcg    2460
```

```
gtggttttttt tgtttgcaag cagcagatta cgcgcagaaa aaaaggatct caagaagatc    2520
ctttgatctt ttctacgggg tctgacgctc agtggaacga aaactcacgt taagggattt    2580
tggtcatgag attatcaaaa aggatcttca cctagatcct tttaaattaa aaatgaagtt    2640
ttaaatcaat ctaaagtata tatgagtaaa cttggtctga cagttaccaa tgcttaatca    2700
gtgaggcacc tatctcagcg atctgtctat ttcgttcatc catagttgcc tgactccccg    2760
tcgtgtagat aactacgata cgggagggct taccatctgg ccccagtgct gcaatgatac    2820
cgcgagaccc acgctcaccg gctccagatt tatcagcaat aaaccagcca gccggaaggg    2880
ccgagcgcag aagtggtcct gcaactttat ccgcctccat ccagtctatt aattgttgcc    2940
gggaagctag agtaagtagt tcgccagtta atagtttgcg caacgttgtt gccattgcta    3000
caggcatcgt ggtgtcacgc tcgtcgtttg gtatggcttc attcagctcc ggttcccaac    3060
gatcaaggcg agttacatga tcccccatgt tgtgcaaaaa agcggttagc tccttcggtc    3120
ctccgatcgt tgtcagaagt aagttggccg cagtgttatc actcatggtt atggcagcac    3180
tgcataattc tcttactgtc atgccatccg taagatgctt ttctgtgact ggtgagtact    3240
caaccaagtc attctgagaa tagtgtatgc ggcgaccgag ttgctcttgc ccggcgtcaa    3300
tacgggataa taccgcgcca catagcagaa ctttaaaagt gctcatcatt ggaaaacgtt    3360
cttcggggcg aaaactctca aggatcttac cgctgttgag atccagttcg atgtaaccca    3420
ctcgtgcacc caactgatct tcagcatctt ttactttcac cagcgtttct gggtgagcaa    3480
aaacaggaag gcaaaatgcc gcaaaaaagg aataagggc gacacggaaa tgttgaatac    3540
tcatactctt cctttttcaa tattattgaa gcatttatca gggttattgt ctcatgagcg    3600
gatacatatt tgaatgtatt tagaaaaata acaaataggg gttccgcgc acatttcccc    3660 gaaaagtgcc acctgacgtc taagaaacca ttattatcat gacattaacc tataaaaata    3720
ggcgtatcac gaggcccttt cgtctcgcgc gtttcggtga tgacggtgaa aacctctgac    3780
acatgcagct cccggagacg gtcacagctt gtctgtaagc ggatgccggg agcagacaag    3840
cccgtcaggg cgcgtcagcg ggtgttggcg ggtgtcgggg ctggcttaac tatgcggcat    3900
cagagcagat tgtactgaga gtgcaccata tgcggtgtga ataccgcac agatgcgtaa    3960 ggagaaaata ccgcatcagg cgccattcgc cattcaggct gcgcaactgt tgggaagggc    4020
gatcggtgcg ggcctcttcg ctattacgcc agctggcgaa aggggatgt gctgcaaggc    4080 gattaagttg ggtaacgcca gggttttccc agtcacgacg ttgtaaaacg acggccagt    4139
```

<210> SEQ ID NO 8
<211> LENGTH: 4178
<212> TYPE: DNA
<213> ORGANISM: Artificial Sequence
<220> FEATURE:
<223> OTHER INFORMATION: Recombinant vector

<400> SEQUENCE: 8

```
gagttcgagc ttgcatgcct gcaggtcgtt acataactta cggtaaatgg cccgcctggc     60
tgaccgccca acgacccccg cccattgacg tcaataatga cgtatgttcc catagtaacg    120
ccaataggga ctttccattg acgtcaatgg gtggagtatt tacggtaaac tgcccacttg    180
gcagtacatc aagtgtatca tatgccaagt acgcccccta ttgacgtcaa tgacggtaaa    240
tggcccgcct ggcattatgc ccagtacatg accttatggg actttcctac ttggcagtac    300
atctacgtat tagtcatcgc tattaccatg gtgatgcggt tttggcagta catcaatggg    360
cgtggatagc ggtttgactc acggggattt ccaagtctcc accccattga cgtcaatggg    420
```

```
agtttgttttt ggcaccaaaa tcaacgggac tttccaaaat gtcgtaacaa ctccgcccca    480
ttgacgcaaa tgggcggtag gcgtgtacgg tgggaggtct atataagcag agctcgttta    540
gtgaaccgtc agatcgcctg gagacgccat ccacgctgtt tgacctcca tagaagacac    600
cgggaccgat ccagcctccg gactctagag gatccggtac tagaggaact gaaaaaccag    660
aaagttaact ggtaagttta gtcttttttgt cttttatttc aggtcccgga tccggtggtg    720
gtgcaaatca aagaactgct cctcagtgga tgttgccttt acttctaggc ctgtacggaa    780
gtgttacttc tgctctaaaa gctgcggaat gtacccgcg ggcccaccat ggcatcaatg    840
gggcgattca tcttcgtgag cttcggcttg ctggtcgtgt tcctctccct gagtggtact    900
ggagctggtt tggaggattg tgactttggt tggtctccct atgatcagca ttgctaccag    960
gcattcaatg aacaaaaaac ctgggatgag gcagagaagt tctgcagggc gcaggagaat    1020
ggtgcgcatc tggcctctat cgaaagcaat ggagaagcag actttgtttc ctggctgatt    1080
tctcagaaag acgaactggc agacgaagac tacgtctgga tcggactgag ggctcaaaac    1140
aaagaacagc aatgcagctc ggagtggagc gatggctcca gtgtcagtta tgagaacttg    1200
attgatctac atacgaaaaa gtgtggtgcg ctggaaaaac tgacagggtt tcgtaagtgg    1260
gtcaattatt actgtgaaca aatgcatgct ttcgtctgca agctcctgcc atattaaatc    1320
cagacatgat aagatacatt gatgagtttg acaaaccac aactagaatg cagtgaaaaa    1380
aatgctttat ttgtgaaatt tgtgatgcta ttgctttatt tgtaaccatt ataagctgca    1440
ataaacaagt taacaacaac aattgcattc atttttatgtt tcaggttcag ggggaggtgt    1500
gggaggtttt ttcggatcct ctagagtcga tctgcaggca tgctagcttg gcgtaatcat    1560
ggtcatagct gtttcctgtg tgaaattgtt atccgctcac aattccacac aacatacgag    1620
ccggaagcat aaagtgtaaa gcctggggtg cctaatgagt gagctaactc acattaattg    1680
cgttgcgctc actgcccgct ttccagtcgg gaaacctgtc gtgccagctg cattaatgaa    1740
tcggccaacg cgcggggaga ggcggtttgc gtattgggcg ctcttccgct tcctcgctca    1800
ctgactcgct gcgctcggtc gttcggctgc ggcgagcggt atcagctcac tcaaaggcgg    1860
taatacggtt atccacagaa tcaggggata acgcaggaaa gaacatgtga gcaaaaggcc    1920
agcaaaaggc caggaaccgt aaaaaggccg cgttgctggc gtttttccat aggctccgcc    1980
ccctgacga gcatcacaaa aatcgacgct caagtcagag gtggcgaaac ccgacaggac    2040
tataaagata ccaggcgttt ccccctggaa gctccctcgt gcgctctcct gttccgaccc    2100
tgccgcttac cggatacctg tccgcctttc tcccttcggg aagcgtggcg ctttctcata    2160
gctcacgctg taggtatctc agttcggtgt aggtcgttcg ctccaagctg ggctgtgtgc    2220
acgaaccccc cgttcagccc gaccgctgcg ccttatccgg taactatcgt cttgagtcca    2280
acccggtaag acacgactta tcgccactgg cagcagccac tggtaacagg attagcagag    2340
cgaggtatgt aggcggtgct acagagttct tgaagtggtg gcctaactac ggctacacta    2400
gaaggacagt atttggtatc tgcgctctgc tgaagccagt taccttcgga aaaagagttg    2460
gtagctcttg atccggcaaa caaaccaccg ctggtagcgg tggttttttt gtttgcaagc    2520
agcagattac gcgcagaaaa aaaggatctc aagaagatcc tttgatcttt tctacggggt    2580
ctgacgctca gtggaacgaa aactcacgtt aagggatttt ggtcatgaga ttatcaaaaa    2640
ggatcttcac ctagatcctt ttaaattaaa aatgaagttt taaatcaatc taagtatat    2700
atgagtaaac ttggtctgac agttaccaat gcttaatcag tgaggcacct atctcagcga    2760
```

| | |
|---|---|
| tctgtctatt tcgttcatcc atagttgcct gactccccgt cgtgtagata actacgatac | 2820 |
| gggagggctt accatctggc cccagtgctg caatgatacc gcgagaccca cgctcaccgg | 2880 |
| ctccagattt atcagcaata aaccagccag ccggaagggc cgagcgcaga agtggtcctg | 2940 |
| caactttatc cgcctccatc cagtctatta attgttgccg ggaagctaga gtaagtagtt | 3000 |
| cgccagttaa tagtttgcgc aacgttgttg ccattgctac aggcatcgtg gtgtcacgct | 3060 |
| cgtcgtttgg tatggcttca ttcagctccg gttcccaacg atcaaggcga gttacatgat | 3120 |
| cccccatgtt gtgcaaaaaa gcggttagct ccttcggtcc tccgatcgtt gtcagaagta | 3180 |
| agttggccgc agtgttatca ctcatggtta tggcagcact gcataattct cttactgtca | 3240 |
| tgccatccgt aagatgcttt tctgtgactg gtgagtactc aaccaagtca ttctgagaat | 3300 |
| agtgtatgcg gcgaccgagt tgctcttgcc cggcgtcaat acgggataat accgcgccac | 3360 |
| atagcagaac tttaaaagtg ctcatcattg gaaaacgttc ttcggggcga aaactctcaa | 3420 |
| ggatcttacc gctgttgaga tccagttcga tgtaacccac tcgtgcaccc aactgatctt | 3480 |
| cagcatcttt tactttcacc agcgtttctg ggtgagcaaa aacaggaagg caaaatgccg | 3540 |
| caaaaaaggg aataagggcg acacggaaat gttgaatact catactcttc ctttttcaat | 3600 |
| attattgaag catttatcag ggttattgtc tcatgagcgg atacatattt gaatgtattt | 3660 |
| agaaaaataa acaaataggg gttccgcgca catttccccg aaaagtgcca cctgacgtct | 3720 |
| aagaaaccat tattatcatg acattaacct ataaaaatag gcgtatcacg aggccctttc | 3780 |
| gtctcgcgcg tttcggtgat gacggtgaaa acctctgaca catgcagctc ccggagacgg | 3840 |
| tcacagcttg tctgtaagcg gatgccggga gcagacaagc ccgtcagggc gcgtcagcgg | 3900 |
| gtgttggcgg gtgtcggggc tggcttaact atgcggcatc agagcagatt gtactgagag | 3960 |
| tgcaccatat gcggtgtgaa ataccgcaca gatgcgtaag gagaaaatac cgcatcaggc | 4020 |
| gccattcgcc attcaggctg cgcaactgtt gggaagggcg atcggtgcgg gcctcttcgc | 4080 |
| tattacgcca gctggcgaaa gggggatgtg ctgcaaggcg attaagttgg gtaacgccag | 4140 |
| ggttttccca gtcacgacgt tgtaaaacga cggccagt | 4178 |

<210> SEQ ID NO 9
<211> LENGTH: 4139
<212> TYPE: DNA
<213> ORGANISM: Artificial Sequence
<220> FEATURE:
<223> OTHER INFORMATION: Recombinant vector

<400> SEQUENCE: 9

| | |
|---|---|
| gagttcgagc ttgcatgcct gcaggtcgtt acataactta cggtaaatgg cccgcctggc | 60 |
| tgaccgccca cgaccccccg cccattgacg tcaataatga cgtatgttcc catagtaacg | 120 |
| ccaataggga ctttccattg acgtcaatgg gtggagtatt tacggtaaac tgcccacttg | 180 |
| gcagtacatc aagtgtatca tatgccaagt acgcccccta ttgacgtcaa tgacggtaaa | 240 |
| tggcccgcct ggcattatgc ccagtacatg accttatggg actttcctac ttggcagtac | 300 |
| atctacgtat tagtcatcgc tattaccatg gtgatgcggt tttggcagta catcaatggg | 360 |
| cgtggatagc ggtttgactc acggggattt ccaagtctcc accccattga cgtcaatggg | 420 |
| agtttgtttt ggcaccaaaa tcaacgggac tttccaaaat gtcgtaacaa ctccgcccca | 480 |
| ttgacgcaaa tgggcggtag gcgtgtacgg tgggaggtct atataagcag agctcgttta | 540 |
| gtgaaccgtc agatcgcctg gagacgccat ccacgctgtt ttgacctcca tagaagacac | 600 |
| cgggaccgat ccagcctccg gactctagag gatccggtac tagaggaact gaaaaaccag | 660 |

```
aaagttaact ggtaagttta gtcttttgt cttttatttc aggtcccgga tccggtggtg      720
gtgcaaatca aagaactgct cctcagtgga tgttgccttt acttctaggc ctgtacggaa      780
gtgttacttc tgctctaaaa gctgcggaat tgtacccgcg ggcccaccat ggcatcaatg      840
gggcgattca tcttcgtgag cttcggcttg ctggtcgtgt tcctctccct gagtggtact      900
ggagctgatt gtccctctgg ttggtcctcc tatgaagggc attgctacaa gcccttcaat      960
gaaccgaaaa actgggccga tgcagagaga ttctgcaaac tgcagccgaa gcacagccat     1020
ctggtctcct ttcagagcgc tgaagaagca gattttgtgg tcaagttgac cagaccaagg     1080
ttgaaagcca atttagtctg gatgggactg agcaatatct ggcacggatg caactggcag     1140
tggagtgatg gcgccaggct caactacaaa gactggcagg aacaatctga atgtctcgca     1200
ttcaggggag ttcatacaga atggttaaat atggactgca gcagtacttg ctctttcgtc     1260
tgcaagttca aggcatagat ccagacatga taagatacat tgatgagttt ggacaaacca     1320
caactagaat gcagtgaaaa aaatgcttta tttgtgaaat tgtgatgct attgctttat      1380 ttgtaaccat tataagctgc aataaacaag ttaacaacaa caattgcatt catttatgt      1440 ttcaggttca gggggaggtg tgggaggttt tttcggatcc tctagagtcg atctgcaggc     1500
atgctagctt ggcgtaatca tggtcatagc tgtttcctgt gtgaaattgt tatccgctca     1560
caattccaca acatacga gccggaagca taaagtgtaa agcctggggt gcctaatgag      1620
tgagctaact cacattaatt gcgttgcgct cactgcccgc tttccagtcg ggaaacctgt     1680
cgtgccagct gcattaatga atcggccaac gcgcggggag aggcggtttg cgtattgggc     1740
gctcttccgc ttcctcgctc actgactcgc tgcgctcggt cgttcggctg cggcgagcgg     1800
tatcagctca ctcaaaggcg gtaatacggt tatccacaga atcaggggat aacgcaggaa     1860
agaacatgtg agcaaaaggc cagcaaaagg ccaggaaccg taaaaaggcc gcgttgctgg     1920
cgttttccca taggctccgc ccccctgacg agcatcacaa aaatcgacgc tcaagtcaga     1980
ggtggcgaaa cccgacagga ctataaagat accaggcgtt tccccctgga agctccctcg     2040
tgcgctctcc tgttccgacc ctgccgctta ccggatacct gtccgccttt ctcccttcgg     2100
gaagcgtggc gctttctcat agctcacgct gtaggtatct cagttcggtg taggtcgttc     2160
gctccaagct gggctgtgtg cacgaacccc ccgttcagcc cgaccgctgc gccttatccg     2220
gtaactatcg tcttgagtcc aacccggtaa gacacgactt atcgccactg gcagcagcca     2280
ctggtaacag gattagcaga gcgaggtatg taggcggtgc tacagagttc ttgaagtggt     2340
ggcctaacta cggctacact agaaggacag tatttggtat ctgcgctctg ctgaagccag     2400
ttaccttcgg aaaaagagtt ggtagctctt gatccggcaa acaaaccacc gctggtagcg     2460
gtggtttttt tgtttgcaag cagcagatta cgcgcagaaa aaaaggatct caagaagatc     2520
ctttgatctt ttctacgggg tctgacgctc agtggaacga aaactcacgt taagggattt     2580
tggtcatgag attatcaaaa aggatcttca cctagatcct tttaaattaa aaatgaagtt     2640
ttaaatcaat ctaaagtata tatgagtaaa cttggtctga cagttaccaa tgcttaatca     2700
gtgaggcacc tatctcagcg atctgtctat ttcgttcatc catagttgcc tgactccccg     2760
tcgtgtagat aactacgata cgggagggct taccatctgg ccccagtgct gcaatgatac     2820
cgcgagaccc acgctcaccg gctccagatt tatcagcaat aaaccagcca gccggaaggg     2880
ccgagcgcag aagtggtcct gcaactttat ccgcctccat ccagtctatt aattgttgcc     2940
gggaagctag agtaagtagt tcgccagtta atagtttgcg caacgttgtt gccattgcta     3000
```

| | |
|---|---|
| caggcatcgt ggtgtcacgc tcgtcgtttg gtatggcttc attcagctcc ggttcccaac | 3060 |
| gatcaaggcg agttacatga tcccccatgt tgtgcaaaaa agcggttagc tccttcggtc | 3120 |
| ctccgatcgt tgtcagaagt aagttggccg cagtgttatc actcatggtt atggcagcac | 3180 |
| tgcataattc tcttactgtc atgccatccg taagatgctt ttctgtgact ggtgagtact | 3240 |
| caaccaagtc attctgagaa tagtgtatgc ggcgaccgag ttgctcttgc ccggcgtcaa | 3300 |
| tacgggataa taccgcgcca catagcagaa ctttaaaagt gctcatcatt ggaaaacgtt | 3360 |
| cttcggggcg aaaactctca aggatcttac cgctgttgag atccagttcg atgtaaccca | 3420 |
| ctcgtgcacc caactgatct tcagcatctt ttactttcac cagcgtttct gggtgagcaa | 3480 |
| aaacaggaag gcaaaatgcc gcaaaaaagg gaataagggc gacacggaaa tgttgaatac | 3540 |
| tcatactctt cctttttcaa tattattgaa gcatttatca gggttattgt ctcatgagcg | 3600 |
| gatacatatt tgaatgtatt tagaaaaata aacaaatagg ggttccgcgc acatttcccc | 3660 |
| gaaaagtgcc acctgacgtc taagaaacca ttattatcat gacattaacc tataaaaata | 3720 |
| ggcgtatcac gaggcccttt cgtctcgcgc gtttcggtga tgacggtgaa aacctctgac | 3780 |
| acatgcagct cccggagacg gtcacagctt gtctgtaagc ggatgccggg agcagacaag | 3840 |
| cccgtcaggg cgcgtcagcg ggtgttggcg ggtgtcgggg ctggcttaac tatgcggcat | 3900 |
| cagagcagat tgtactgaga gtgcaccata tgcggtgtga ataccgcac agatgcgtaa | 3960 |
| ggagaaaata ccgcatcagg cgccattcgc cattcaggct gcgcaactgt tgggaagggc | 4020 |
| gatcggtgcg ggcctcttcg ctattacgcc agctggcgaa agggggatgt gctgcaaggc | 4080 |
| gattaagttg ggtaacgcca gggttttccc agtcacgacg ttgtaaaacg acggccagt | 4139 |

<210> SEQ ID NO 10
<211> LENGTH: 4139
<212> TYPE: DNA
<213> ORGANISM: Artificial Sequence
<220> FEATURE:
<223> OTHER INFORMATION: Recombinant vector

<400> SEQUENCE: 10

| | |
|---|---|
| gagttcgagc ttgcatgcct gcaggtcgtt acataactta cggtaaatgg cccgcctggc | 60 |
| tgaccgccca acgacccccg cccattgacg tcaataatga cgtatgttcc catagtaacg | 120 |
| ccaataggga ctttccattg acgtcaatgg gtggagtatt tacggtaaac tgcccacttg | 180 |
| gcagtacatc aagtgtatca tatgccaagt acgccccta ttgacgtcaa tgacggtaaa | 240 |
| tggcccgcct ggcattatgc ccagtacatg accttatggg actttcctac ttggcagtac | 300 |
| atctacgtat tagtcatcgc tattaccatg gtgatgcggt tttggcagta catcaatggg | 360 |
| cgtggatagc ggtttgactc acggggattt ccaagtctcc accccattga cgtcaatggg | 420 |
| agtttgtttt ggcaccaaaa tcaacgggac tttccaaaat gtcgtaacaa ctccgcccca | 480 |
| ttgacgcaaa tgggcggtag gcgtgtacgg tgggaggtct atataagcag agctcgttta | 540 |
| gtgaaccgtc agatcgcctg gagacgccat ccacgctgtt ttgacctcca tagaagacac | 600 |
| cgggaccgat ccagcctccg gactctagag gatccggtac tagaggaact gaaaaaccag | 660 |
| aaagttaact ggtaagttta gtcttttttgt cttttatttc aggtcccgga tccggtggtg | 720 |
| gtgcaaatca agaactgct cctcagtgga tgttgccttt acttctaggc ctgtacggaa | 780 |
| gtgttacttc tgctctaaaa gctgcggaat tgtaccgcg ggccaccat ggcatcaatg | 840 |
| ggccggttca tcttcgtgtc cttcggcctg ctggtggtgt tcctgagcct gtccggaaca | 900 |
| ggcgccgact gtccttccgg ctggtcctcc tacgagggcc actgctacaa gccctttaac | 960 |

```
gagcccaaga actgggctga cgccgaggcg ttctgcgcgc tgcagcccaa gcactcccac    1020
ctcgtgagct tccagtccgc cgaggaggcc gacttcgtgg tgaagctgac caggcccagg    1080
ctgaaggcca acctggtgtg gatgggcctg tccaacatct ggcacggctg taactggcag    1140
tggtccgacg gcgccaggct gaactacaag gactggcagg agcagtccga gtgtctggcc    1200
ttcaggggcg tgcacaccga gtggctgaac atggactgct cctccacctg ctccttcgtg    1260
tgcaagttca aggcctgaat ccagacatga taagatacat tgatgagttt ggacaaacca    1320
caactagaat gcagtgaaaa aaatgcttta tttgtgaaat tgtgatgct attgctttat     1380 ttgtaaccat tataagctgc aataaacaag ttaacaacaa caattgcatt cattttatgt    1440
ttcaggttca gggggaggtg tgggaggttt tttcggatcc tctagagtcg atctgcaggc    1500
atgctagctt ggcgtaatca tggtcatagc tgtttcctgt gtgaaattgt tatccgctca    1560
caattccaca acacatacga gccggaagca taaagtgtaa agcctggggt gcctaatgag    1620
tgagctaact cacattaatt gcgttgcgct cactgcccgc tttccagtcg ggaaacctgt    1680
cgtgccagct gcattaatga atcggccaac gcgcgggag aggcggtttg cgtattgggc     1740
gctcttccgc ttcctcgctc actgactcgc tgcgctcggt cgttcggctg cggcgagcgg    1800
tatcagctca ctcaaaggcg gtaatacggt tatccacaga atcaggggat aacgcaggaa    1860
agaacatgtg agcaaaaggc cagcaaaagg ccaggaaccg taaaaaggcc gcgttgctgg    1920 cgttttttcca taggctccgc cccctgacg agcatcacaa aaatcgacgc tcaagtcaga    1980
ggtggcgaaa cccgacagga ctataaagat accaggcgtt tcccctggaa gctccctcg    2040 tgcgctctcc tgttccgacc ctgccgctta ccggatacct gtccgccttt ctcccttcgg    2100
gaagcgtggc gctttctcat agctcacgct gtaggtatct cagttcggtg taggtcgttc    2160
gctccaagct gggctgtgtg cacgaacccc ccgttcagcc cgaccgctgc gccttatccg    2220
gtaactatcg tcttgagtcc aacccggtaa gacacgactt atcgccactg gcagcagcca    2280
ctggtaacag gattagcaga gcgaggtatg taggcggtgc tacagagttc ttgaagtggt    2340
ggcctaacta cggctacact agaaggacag tatttggtat ctgcgctctg ctgaagccag    2400
ttaccttcgg aaaaagagtt ggtagctctt gatccggcaa acaaaccacc gctggtagcg    2460
gtggtttttt tgtttgcaag cagcagatta cgcgcagaaa aaaaggatct caagaagatc    2520
ctttgatctt ttctacgggg tctgacgctc agtggaacga aaactcacgt taagggattt    2580
tggtcatgag attatcaaaa aggatcttca cctagatcct tttaaattaa aaatgaagtt    2640
ttaaatcaat ctaaagtata tatgagtaaa cttggtctga cagttaccaa tgcttaatca    2700
gtgaggcacc tatctcagcg atctgtctat ttcgttcatc catagttgcc tgactccccg    2760
tcgtgtagat aactacgata cgggagggct taccatctgg ccccagtgct gcaatgatac    2820
cgcgagaccc acgctcaccg gctccagatt tatcagcaat aaaccagcca gccggaaggg    2880
ccgagcgcag aagtggtcct gcaactttat ccgcctccat ccagtctatt aattgttgcc    2940
gggaagctag agtaagtagt tcgccagtta atagtttgcg caacgttgtt gccattgcta    3000
caggcatcgt ggtgtcacgc tcgtcgtttg gtatggcttc attcagctcc ggttcccaac    3060
gatcaaggcg agttacatga tcccccatgt tgtgcaaaaa agcggttagc tccttcggtc    3120
ctccgatcgt tgtcagaagt aagttggccg cagtgttatc actcatggtt atggcagcac    3180
tgcataattc tcttactgtc atgccatccg taagatgctt ttctgtgact ggtgagtact    3240
caaccaagtc attctgagaa tagtgtatgc ggcgaccgag ttgctcttgc ccggcgtcaa    3300
```

| | |
|---|---|
| tacgggataa taccgcgcca catagcagaa ctttaaaagt gctcatcatt ggaaaacgtt | 3360 |
| cttcggggcg aaaactctca aggatcttac cgctgttgag atccagttcg atgtaaccca | 3420 |
| ctcgtgcacc caactgatct tcagcatctt ttactttcac cagcgtttct gggtgagcaa | 3480 |
| aaacaggaag gcaaaatgcc gcaaaaaagg gaataagggc gacacggaaa tgttgaatac | 3540 |
| tcatactctt cctttttcaa tattattgaa gcatttatca gggttattgt ctcatgagcg | 3600 |
| gatacatatt tgaatgtatt tagaaaaata acaaataggg gttccgcgc acatttcccc | 3660 |
| gaaaagtgcc acctgacgtc taagaaacca ttattatcat gacattaacc tataaaaata | 3720 |
| ggcgtatcac gaggcccttt cgtctcgcgc gtttcggtga tgacggtgaa aacctctgac | 3780 |
| acatgcagct cccggagacg gtcacagctt gtctgtaagc ggatgccggg agcagacaag | 3840 |
| cccgtcaggg cgcgtcagcg ggtgttggcg ggtgtcgggg ctggcttaac tatgcggcat | 3900 |
| cagagcagat tgtactgaga gtgcaccata tgcggtgtga ataccgcac agatgcgtaa | 3960 |
| ggagaaaata ccgcatcagg cgccattcgc cattcaggct gcgcaactgt tgggaagggc | 4020 |
| gatcggtgcg ggcctcttcg ctattacgcc agctggcgaa aggggggatgt gctgcaaggc | 4080 |
| gattaagttg ggtaacgcca gggttttccc agtcacgacg ttgtaaaacg acggccagt | 4139 |

<210> SEQ ID NO 11
<211> LENGTH: 4139
<212> TYPE: DNA
<213> ORGANISM: Artificial Sequence
<220> FEATURE:
<223> OTHER INFORMATION: Recombinant vector

<400> SEQUENCE: 11

| | |
|---|---|
| gagttcgagc ttgcatgcct gcaggtcgtt acataactta cggtaaatgg cccgcctggc | 60 |
| tgaccgccca cgaccccccg cccattgacg tcaataatga cgtatgttcc catagtaacg | 120 |
| ccaataggga ctttccattg acgtcaatgg gtggagtatt tacggtaaac tgcccacttg | 180 |
| gcagtacatc aagtgtatca tatgccaagt acgccccta ttgacgtcaa tgacggtaaa | 240 |
| tggcccgcct ggcattatgc ccagtacatg accttatggg actttcctac ttggcagtac | 300 |
| atctacgtat tagtcatcgc tattaccatg gtgatgcggt tttggcagta catcaatggg | 360 |
| cgtggatagc ggtttgactc acggggattt ccaagtctcc accccattga cgtcaatggg | 420 |
| agtttgtttt ggcaccaaaa tcaacgggac tttccaaaat gtcgtaacaa ctccgcccca | 480 |
| ttgacgcaaa tgggcggtag gcgtgtacgg tgggaggtct atataagcag agctcgttta | 540 |
| gtgaaccgtc agatcgcctg gagacgccat ccacgctgtt ttgacctcca tagaagacac | 600 |
| cgggaccgat ccagcctccg gactctagag gatccggtac tagaggaact gaaaaaccag | 660 |
| aaagttaact ggtaagttta gtcttttgt cttttatttc aggtcccgga tccggtggtg | 720 |
| gtgcaaatca aagaactgct cctcagtgga tgttgccttt acttctaggc ctgtacggaa | 780 |
| gtgttacttc tgctctaaaa gctgcggaat tgtacccgcg gcccaccat ggcatcaatg | 840 |
| ggccggttca tcttcgtgtc cttcggcctg ctggtggtgt tcctgagcct gtccggaaca | 900 |
| ggcgccgact gtcettccgg ctggtcctcc tacgagggcc actgctacaa gcccttaaac | 960 |
| gagcccaaga ctgggctga cgccgagcgg ttctgcaagc tgcagcccaa gcactcccac | 1020 |
| ctcgtgagct ccagtccgc cgaggaggcc gacttcgtgg tgaagctgac cgcgcccagg | 1080 |
| ctgaaggcca acctggtgtg gatgggcctg tccaacatct ggcacggctg taactggcag | 1140 |
| tggtccgacg gcgccaggct gaactacaag gactggcagg agcagtccga gtgtctggcc | 1200 |
| ttcaggggcg tgcacaccga gtggctgaac atggactgct cctccacctg ctccttcgtg | 1260 |

```
tgcaagttca aggcctgaat ccagacatga taagatacat tgatgagttt ggacaaacca    1320
caactagaat gcagtgaaaa aaatgcttta tttgtgaaat ttgtgatgct attgctttat    1380
ttgtaaccat tataagctgc aataaacaag ttaacaacaa caattgcatt cattttatgt    1440
ttcaggttca gggggaggtg tgggaggttt tttcggatcc tctagagtcg atctgcaggc    1500
atgctagctt ggcgtaatca tggtcatagc tgtttcctgt gtgaaattgt tatccgctca    1560
caattccaca acatacga gccggaagca taaagtgtaa agcctggggt gcctaatgag    1620
tgagctaact cacattaatt gcgttgcgct cactgcccgc tttccagtcg gaaacctgt    1680 cgtgccagct gcattaatga atcggccaac gcgcggggag aggcggtttg cgtattgggc    1740
gctcttccgc ttcctcgctc actgactcgc tgcgctcggt cgttcggctg cggcgagcgg    1800
tatcagctca ctcaaaggcg gtaatacggt tatccacaga atcaggggat aacgcaggaa    1860
agaacatgtg agcaaaaggc cagcaaaagg ccaggaaccg taaaaaggcc gcgttgctgg    1920
cgttttccca taggctccgc cccctgacg agcatcacaa aatcgacgc tcaagtcaga    1980 ggtggcgaaa cccgacagga ctataaagat accaggcgtt tccccctgga agctccctcg    2040
tgcgctctcc tgttccgacc ctgccgctta ccggatacct gtccgccttt ctcccttcgg    2100
gaagcgtggc gctttctcat agctcacgct gtaggtatct cagttcggtg taggtcgttc    2160
gctccaagct gggctgtgtg cacgaaccc ccgttcagcc cgaccgctgc gccttatccg    2220
gtaactatcg tcttgagtcc aacccggtaa gacacgactt atcgccactg gcagcagcca    2280
ctggtaacag gattagcaga gcgaggtatg taggcggtgc tacagagttc ttgaagtggt    2340
ggcctaacta cggctacact agaaggacag tatttggtat ctgcgctctg ctgaagccag    2400
ttaccttcgg aaaaagagtt ggtagctctt gatccggcaa acaaaccacc gctggtagcg    2460
gtggtttttt tgtttgcaag cagcagatta cgcgcagaaa aaaaggatct caagaagatc    2520
ctttgatctt ttctacgggg tctgacgctc agtggaacga aaactcacgt taagggattt    2580
tggtcatgag attatcaaaa aggatcttca cctagatcct tttaaattaa aaatgaagtt    2640
ttaaatcaat ctaaagtata tatgagtaaa cttggtctga cagttaccaa tgcttaatca    2700
gtgaggcacc tatctcagcg atctgtctat ttcgttcatc catagttgcc tgactccccg    2760
tcgtgtagat aactacgata cgggagggct taccatctgg ccccagtgct gcaatgatac    2820
cgcgagaccc acgctcaccg gctccagatt tatcagcaat aaaccagcca gccggaaggg    2880
ccgagcgcag aagtggtcct gcaactttat ccgcctccat ccagtctatt aattgttgcc    2940
gggaagctag agtaagtagt tcgccagtta atagtttgcg caacgttgtt gccattgcta    3000
caggcatcgt ggtgtcacgc tcgtcgtttg gtatggcttc attcagctcc ggttcccaac    3060
gatcaaggcg agttacatga tcccccatgt tgtgcaaaaa agcggttagc tccttcggtc    3120
ctccgatcgt tgtcagaagt aagttggccg cagtgttatc actcatggtt atggcagcac    3180
tgcataattc tcttactgtc atgccatccg taagatgctt ttctgtgact ggtgagtact    3240
caaccaagtc attctgagaa tagtgtatgc ggcgaccgag ttgctcttgc ccggcgtcaa    3300
tacgggataa taccgcgcca catagcagaa ctttaaaagt gctcatcatt ggaaaacgtt    3360
cttcggggcg aaaactctca aggatcttac cgctgttgag atccagttcg atgtaaccca    3420
ctcgtgcacc caactgatct tcagcatctt ttactttcac cagcgtttct gggtgagcaa    3480
aaacaggaag gcaaaatgcc gcaaaaaagg gaataagggc gacacggaaa tgttgaatac    3540
tcatactctt cctttttcaa tattattgaa gcatttatca gggttattgt ctcatgagcg    3600
```

| | | |
|---|---|---|
| gatacatatt tgaatgtatt tagaaaaata aacaaatagg ggttccgcgc acatttcccc | 3660 | |
| gaaaagtgcc acctgacgtc taagaaacca ttattatcat gacattaacc tataaaaata | 3720 | |
| ggcgtatcac gaggcccttt cgtctcgcgc gtttcggtga tgacggtgaa aacctctgac | 3780 | |
| acatgcagct cccggagacg gtcacagctt gtctgtaagc ggatgccggg agcagacaag | 3840 | |
| cccgtcaggg cgcgtcagcg ggtgttggcg ggtgtcgggg ctggcttaac tatgcggcat | 3900 | |
| cagagcagat tgtactgaga gtgcaccata tgcggtgtga ataccgcac agatgcgtaa | 3960 | |
| ggagaaaata ccgcatcagg cgccattcgc cattcaggct gcgcaactgt tgggaagggc | 4020 | |
| gatcggtgcg ggcctcttcg ctattacgcc agctggcgaa aggggatgt gctgcaaggc | 4080 | |
| gattaagttg ggtaacgcca gggttttccc agtcacgacg ttgtaaaacg acggccagt | 4139 | |

<210> SEQ ID NO 12
<211> LENGTH: 4139
<212> TYPE: DNA
<213> ORGANISM: Artificial Sequence
<220> FEATURE:
<223> OTHER INFORMATION: Recombinant vector

<400> SEQUENCE: 12

| | | |
|---|---|---|
| gagttcgagc ttgcatgcct gcaggtcgtt acataactta cggtaaatgg cccgcctggc | 60 | |
| tgaccgccca acgacccccg cccattgacg tcaataatga cgtatgttcc catagtaacg | 120 | |
| ccaataggga ctttccattg acgtcaatgg gtggagtatt tacggtaaac tgcccacttg | 180 | |
| gcagtacatc aagtgtatca tatgccaagt acgcccccta ttgacgtcaa tgacggtaaa | 240 | |
| tggcccgcct ggcattatgc ccagtacatg accttatggg actttcctac ttggcagtac | 300 | |
| atctacgtat tagtcatcgc tattaccatg gtgatgcggt tttggcagta catcaatggg | 360 | |
| cgtggatagc ggtttgactc acggggattt ccaagtctcc accccattga cgtcaatggg | 420 | |
| agtttgtttt ggcaccaaaa tcaacgggac tttccaaaat gtcgtaacaa ctccgcccca | 480 | |
| ttgacgcaaa tgggcggtag gcgtgtacgg tgggaggtct atataagcag agctcgttta | 540 | |
| gtgaaccgtc agatcgcctg gagacgccat ccacgctgtt ttgacctcca tagaagacac | 600 | |
| cgggaccgat ccagcctccg gactctagag gatccggtac tagaggaact gaaaaaccag | 660 | |
| aaagttaact ggtaagttta gtcttttttgt cttttatttc aggtcccgga tccggtggtg | 720 | |
| gtgcaaatca aagaactgct cctcagtgga tgttgccttt acttctaggc ctgtacggaa | 780 | |
| gtgttacttc tgctctaaaa gctgcggaat tgtacccgcg gcccaccat ggcatcaatg | 840 | |
| ggccggttca tcttcgtgtc cttcggcctg ctggtggtgt tcctgagcct gtccggaaca | 900 | |
| ggcgccgact gtccttccgg ctggtcctcc tacgagggcc actgctacaa gcccttaac | 960 | |
| gagcccaaga ctgggctga cgccgagcgg ttctgcaagc tgcagccaa gcactccac | 1020 | |
| ctcgtgagct tccagtccgc cgaggaggcc gacttcgtgg tggcgctgac cgcgcccagg | 1080 | |
| ctgaaggcca acctggtgtg gatgggcctg tccaacatct ggcacggctg taactggcag | 1140 | |
| tggtccgacg gcgccaggct gaactacaag gactggcagg agcagtccga gtgtctggcc | 1200 | |
| ttcagggggcg tgcacaccga gtggctgaac atggactgct cctccacctg ctccttcgtg | 1260 | |
| tgcaagttca aggcctgaat ccagacatga taagatacat tgatgagttt ggacaaacca | 1320 | |
| caactagaat gcagtgaaaa aaatgcttta tttgtgaaat ttgtgatgct attgctttat | 1380 | |
| ttgtaaccat tataagctgc aataaacaag ttaacaacaa caattgcatt catttatgt | 1440 | |
| ttcaggttca gggggaggtg tgggaggttt tttcggatcc tctagagtcg atctgcaggc | 1500 | |
| atgctagctt ggcgtaatca tggtcatagc tgtttcctgt gtgaaattgt tatccgctca | 1560 | |

```
caattccaca caacatacga gccggaagca taaagtgtaa agcctggggt gcctaatgag    1620
tgagctaact cacattaatt gcgttgcgct cactgcccgc tttccagtcg ggaaacctgt    1680
cgtgccagct gcattaatga atcggccaac gcgcggggag aggcggtttg cgtattgggc    1740
gctcttccgc ttcctcgctc actgactcgc tgcgctcggt cgttcggctg cggcgagcgg    1800
tatcagctca ctcaaaggcg gtaatacggt tatccacaga atcaggggat aacgcaggaa    1860
agaacatgtg agcaaaaggc cagcaaaagg ccaggaaccg taaaaaggcc gcgttgctgg    1920
cgttttccca taggctccgc cccccctgacg agcatcacaa aaatcgacgc tcaagtcaga    1980
ggtggcgaaa cccgacagga ctataaagat accaggcgtt tccccctgga agctccctcg    2040
tgcgctctcc tgttccgacc ctgccgctta ccggatacct gtccgccttt ctcccttcgg    2100
gaagcgtggc gctttctcat agctcacgct gtaggtatct cagttcggtg taggtcgttc    2160
gctccaagct gggctgtgtg cacgaacccc ccgttcagcc cgaccgctgc gccttatccg    2220
gtaactatcg tcttgagtcc aacccggtaa gacacgactt atcgccactg gcagcagcca    2280
ctggtaacag gattagcaga gcgaggtatg taggcggtgc tacagagttc ttgaagtggt    2340
ggcctaacta cggctacact agaaggacag tatttggtat ctgcgctctg ctgaagccag    2400
ttaccttcgg aaaaagagtt ggtagctctt gatccggcaa acaaaccacc gctggtagcg    2460
gtggtttttt tgtttgcaag cagcagatta cgcgcagaaa aaaaggatct caagaagatc    2520
ctttgatctt ttctacgggg tctgacgctc agtggaacga aaactcacgt taagggattt    2580
tggtcatgag attatcaaaa aggatcttca cctagatcct tttaaattaa aaatgaagtt    2640
ttaaatcaat ctaaagtata tatgagtaaa cttggtctga cagttaccaa tgcttaatca    2700
gtgaggcacc tatctcagcg atctgtctat ttcgttcatc catagttgcc tgactccccg    2760
tcgtgtagat aactacgata cgggagggct taccatctgg ccccagtgct gcaatgatac    2820
cgcgagaccc acgctcaccg gctccagatt tatcagcaat aaaccagcca gccgaaggg    2880 ccgagcgcag aagtggtcct gcaactttat ccgcctccat ccagtctatt aattgttgcc    2940
gggaagctag agtaagtagt tcgccagtta atagtttgcg caacgttgtt gccattgcta    3000
caggcatcgt ggtgtcacgc tcgtcgtttg gtatggcttc attcagctcc ggttcccaac    3060
gatcaaggcg agttacatga tcccccatgt tgtgcaaaaa agcggttagc tccttcggtc    3120
ctccgatcgt tgtcagaagt aagttggccg cagtgttatc actcatggtt atggcagcac    3180
tgcataattc tcttactgtc atgccatccg taagatgctt ttctgtgact ggtgagtact    3240
caaccaagtc attctgagaa tagtgtatgc ggcgaccgag ttgctcttgc ccggcgtcaa    3300
tacgggataa taccgcgcca catagcagaa ctttaaaagt gctcatcatt ggaaaacgtt    3360
cttcggggcg aaaactctca aggatcttac cgctgttgag atccagttcg atgtaaccca    3420
ctcgtgcacc caactgatct tcagcatctt ttactttcac cagcgtttct gggtgagcaa    3480
aaacaggaag gcaaaatgcc gcaaaaaagg aataagggc gacacggaaa tgttgaatac    3540
tcatactctt cctttttcaa tattattgaa gcatttatca gggttattgt ctcatgagcg    3600
gatacatatt tgaatgtatt tagaaaaata aacaaatagg ggttccgcgc acatttcccc    3660
gaaaagtgcc acctgacgtc taagaaacca ttattatcat gacattaacc tataaaaata    3720
ggcgtatcac gaggcccttt cgtctcgcgc gtttcggtga tgacggtgaa aacctctgac    3780
acatgcagct cccggagacg gtcacagctt gtctgtaagc ggatgccggg agcagacaag    3840
cccgtcaggg cgcgtcagcg ggtgttggcg ggtgtcgggg ctggcttaac tatgcggcat    3900
```

| | |
|---|---|
| cagagcagat tgtactgaga gtgcaccata tgcggtgtga aataccgcac agatgcgtaa | 3960 |
| ggagaaaata ccgcatcagg cgccattcgc cattcaggct gcgcaactgt tgggaagggc | 4020 |
| gatcggtgcg ggcctcttcg ctattacgcc agctggcgaa agggggatgt gctgcaaggc | 4080 |
| gattaagttg ggtaacgcca gggttttccc agtcacgacg ttgtaaaacg acggccagt | 4139 |

```
<210> SEQ ID NO 13
<211> LENGTH: 4139
<212> TYPE: DNA
<213> ORGANISM: Artificial Sequence
<220> FEATURE:
<223> OTHER INFORMATION: Recombinant vector

<400> SEQUENCE: 13
```

| | |
|---|---|
| gagttcgagc ttgcatgcct gcaggtcgtt acataactta cggtaaatgg cccgcctggc | 60 |
| tgaccgccca acgaccccg cccattgacg tcaataatga cgtatgttcc catagtaacg | 120 |
| ccaatagga cttttccattg acgtcaatgg gtggagtatt tacggtaaac tgcccacttg | 180 |
| gcagtacatc aagtgtatca tatgccaagt acgccccta ttgacgtcaa tgacggtaaa | 240 |
| tggcccgcct ggcattatgc ccagtacatg accttatggg actttcctac ttggcagtac | 300 |
| atctacgtat tagtcatcgc tattaccatg gtgatgcggt tttggcagta catcaatggg | 360 |
| cgtggatagc ggtttgactc acggggattt ccaagtctcc accccattga cgtcaatggg | 420 |
| agtttgtttt ggcaccaaaa tcaacgggac tttccaaaat gtcgtaacaa ctccgcccca | 480 |
| ttgacgcaaa tgggcggtag gcgtgtacgg tgggaggtct atataagcag agctcgttta | 540 |
| gtgaaccgtc agatcgcctg gagacgccat ccacgctgtt ttgacctcca tagaagacac | 600 |
| cgggaccgat ccagcctccg gactctagag gatccggtac tagaggaact gaaaaaccag | 660 |
| aaagttaact ggtaagttta gtcttttgt cttttatttc aggtcccgga tccggtggtg | 720 |
| gtgcaaatca aagaactgct cctcagtgga tgttgccttt acttctaggc ctgtacggaa | 780 |
| gtgttacttc tgctctaaaa gctgcggaat tgtacccgcg gcccaccat ggcatcaatg | 840 |
| ggccggttca tcttcgtgtc cttcggcctg ctggtggtgt cctgagcct gtccggaaca | 900 |
| ggcgccgact gtccttccgg ctggtcctcc tacgagggcc actgctacaa gccctttaac | 960 |
| gagcccaaga ctgggctga cgccgagcgg ttctgcaagc tgcagcccaa gcactccac | 1020 |
| ctcgtgagct ccagtccgc cgaggaggcc gacttcgtgg tgaagctgac caggcccgcg | 1080 |
| ctggcggcca acctggtgtg gatgggcctg tccaacatct ggcacggctg taactggcag | 1140 |
| tggtccgacg gcgccaggct gaactacaag gactggcagg agcagtccga gtgtctggcc | 1200 |
| tcaggggcg tgcacaccga gtggctgaac atggactgct cctccacctg ctccttcgtg | 1260 |
| tgcaagttca aggcctgaat ccagacatga taagatacat tgatgagttt ggacaaacca | 1320 |
| caactagaat gcagtgaaaa aatgctttta tttgtgaaat ttgtgatgct attgctttat | 1380 |
| ttgtaaccat tataagctgc aataaacaag ttaacaacaa caattgcatt cattttatgt | 1440 |
| ttcaggttca gggggaggtg tgggaggttt tttcggatcc tctagagtcg atctgcaggc | 1500 |
| atgctagctt ggcgtaatca tggtcatagc tgtttcctgt gtgaaattgt tatccgctca | 1560 |
| caattccaca acatacga gccggaagca taaagtgtaa agcctggggt gcctaatgag | 1620 |
| tgagctaact cacattaatt gcgttgcgct cactgcccgc tttccagtcg ggaaacctgt | 1680 |
| cgtgccagct gcattaatga atcggccaac gcgcggggag aggcggtttg cgtattgggc | 1740 |
| gctcttccgc ttcctcgctc actgactcgc tgcgctcggt cgttcggctg cggcgagcgg | 1800 |
| tatcagctca ctcaaaggcg gtaatacggt tatccacaga atcaggggat aacgcaggaa | 1860 |

-continued

```
agaacatgtg agcaaaaggc cagcaaaagg ccaggaaccg taaaaaggcc gcgttgctgg    1920
cgttttccca taggctccgc cccctgacg agcatcacaa aaatcgacgc tcaagtcaga    1980
ggtggcgaaa cccgacagga ctataaagat accaggcgtt tccccctgga agctccctcg    2040
tgcgctctcc tgttccgacc ctgccgctta ccggatacct gtccgccttt ctcccttcgg    2100
gaagcgtggc gctttctcat agctcacgct gtaggtatct cagttcggtg taggtcgttc    2160
gctccaagct gggctgtgtg cacgaacccc ccgttcagcc cgaccgctgc gccttatccg    2220
gtaactatcg tcttgagtcc aacccggtaa gacacgactt atcgccactg gcagcagcca    2280
ctggtaacag gattagcaga gcgaggtatg taggcggtgc tacagagttc ttgaagtggt    2340
ggcctaacta cggctacact agaaggacag tatttggtat ctgcgctctg ctgaagccag    2400
ttaccttcgg aaaaagagtt ggtagctctt gatccggcaa acaaaccacc gctggtagcg    2460
gtggtttttt tgtttgcaag cagcagatta cgcgcagaaa aaaggatctc aagaagatc     2520 ctttgatctt ttctacgggg tctgacgctc agtggaacga aaactcacgt taagggattt    2580
tggtcatgag attatcaaaa aggatcttca cctagatcct tttaaattaa aaatgaagtt    2640
ttaaatcaat ctaaagtata tatgagtaaa cttggtctga cagttaccaa tgcttaatca    2700
gtgaggcacc tatctcagcg atctgtctat ttcgttcatc catagttgcc tgactccccg    2760
tcgtgtagat aactacgata cgggagggct taccatctgg ccccagtgct gcaatgatac    2820
cgcgagaccc acgctcaccg gctccagatt tatcagcaat aaaccagcca gccggaaggg    2880
ccgagcgcag aagtggtcct gcaactttat ccgcctccat ccagtctatt aattgttgcc    2940
gggaagctag agtaagtagt tcgccagtta atagtttgcg caacgttgtt gccattgcta    3000
caggcatcgt ggtgtcacgc tcgtcgtttg gtatggcttc attcagctcc ggttcccaac    3060
gatcaaggcg agttacatga tcccccatgt tgtgcaaaaa agcggttagc tccttcggtc    3120
ctccgatcgt tgtcagaagt aagttggccg cagtgttatc actcatggtt atggcagcac    3180
tgcataattc tcttactgtc atgccatccg taagatgctt ttctgtgact ggtgagtact    3240
caaccaagtc attctgagaa tagtgtatgc ggcgaccgag ttgctcttgc ccggcgtcaa    3300
tacgggataa taccgcgcca catagcagaa ctttaaaagt gctcatcatt ggaaaacgtt    3360
cttcggggcg aaaactctca aggatcttac cgctgttgag atccagttcg atgtaaccca    3420
ctcgtgcacc caactgatct tcagcatctt ttactttcac cagcgtttct gggtgagcaa    3480
aaacaggaag gcaaaatgcc gcaaaaaagg gaataagggc gacacggaaa tgttgaatac    3540
tcatactctt ccttttttcaa tattattgaa gcatttatca gggttattgt ctcatgagcg    3600
gatacatatt tgaatgtatt tagaaaaata acaaataggg gttccgcgc acatttcccc    3660 gaaaagtgcc acctgacgtc taagaaacca ttattatcat gacattaacc tataaaaata    3720
ggcgtatcac gaggcccttt cgtctcgcgc gtttcggtga tgacggtgaa aacctctgac    3780
acatgcagct cccggagacg gtcacagctt gtctgtaagc ggatgccggg agcagacaag    3840
cccgtcaggg cgcgtcagcg ggtgttggcg ggtgtcgggg ctggcttaac tatgcggcat    3900
cagagcagat tgtactgaga gtgcaccata tgcggtgtga ataccgcac agatgcgtaa    3960 ggagaaaata ccgcatcagg cgccattcgc cattcaggct gcgcaactgt tgggaagggc    4020
gatcggtgcg ggcctcttcg ctattacgcc agctggcgaa agggggatgt gctgcaaggc    4080
gattaagttg ggtaacgcca gggttttccc agtcacgacg ttgtaaaacg acggccagt     4139
```

<210> SEQ ID NO 14

<211> LENGTH: 4139
<212> TYPE: DNA
<213> ORGANISM: Artificial Sequence
<220> FEATURE:
<223> OTHER INFORMATION: Recombinant vector

<400> SEQUENCE: 14

| | |
|---|---|
| gagttcgagc ttgcatgcct gcaggtcgtt acataactta cggtaaatgg cccgcctggc | 60 |
| tgaccgccca acgaccccg cccattgacg tcaataatga cgtatgttcc catagtaacg | 120 |
| ccaataggga ctttccattg acgtcaatgg gtggagtatt tacggtaaac tgcccacttg | 180 |
| gcagtacatc aagtgtatca tatgccaagt acgcccccta ttgacgtcaa tgacggtaaa | 240 |
| tggcccgcct ggcattatgc ccagtacatg accttatggg actttcctac ttggcagtac | 300 |
| atctacgtat tagtcatcgc tattaccatg gtgatgcggt tttggcagta catcaatggg | 360 |
| cgtggatagc ggtttgactc acggggattt ccaagtctcc accccattga cgtcaatggg | 420 |
| agtttgtttt ggcaccaaaa tcaacgggac tttccaaaat gtcgtaacaa ctccgcccca | 480 |
| ttgacgcaaa tgggcggtag gcgtgtacgg tgggaggtct atataagcag agctcgttta | 540 |
| gtgaaccgtc agatcgcctg gagacgccat ccacgctgtt ttgacctcca tagaagacac | 600 |
| cgggaccgat ccagcctccg gactctagag gatccggtac tagaggaact gaaaaaccag | 660 |
| aaagttaact ggtaagttta gtcttttgt cttttatttc aggtcccgga tccggtggtg | 720 |
| gtgcaaatca aagaactgct cctcagtgga tgttgccttt acttctaggc ctgtacggaa | 780 |
| gtgttacttc tgctctaaaa gctgcggaat tgtacccgcg gcccaccat ggcatcaatg | 840 |
| ggccggttca tcttcgtgtc cttcggcctg ctggtggtgt cctgagcct gtccggaaca | 900 |
| ggcgccgact gtccttccgg ctggtcctcc tacgagggcc actgctacaa gcccttaac | 960 |
| gagcccaaga ctgggctga cgccgaggcg ttctgcgcgc tgcagcccaa gcactcccac | 1020 |
| ctcgtgagct ccagtccgc cgaggaggcc gacttcgtgg tggcgctgac cgcgcccagg | 1080 |
| ctgaaggcca acctggtgtg gatgggcctg tccaacatct ggcacggctg taactggcag | 1140 |
| tggtccgacg gcgccaggct gaactacaag gactggcagg agcagtccga gtgtctggcc | 1200 |
| ttcagggcg tgcacaccga gtggctgaac atggactgct cctccacctg ctccttcgtg | 1260 |
| tgcaagttca aggcctgaat ccagacatga taagatacat tgatgagttt ggacaaacca | 1320 |
| caactagaat gcagtgaaaa aaatgcttta tttgtgaaat ttgtgatgct attgctttat | 1380 |
| ttgtaaccat tataagctgc aataaacaag ttaacaacaa caattgcatt catttatgt | 1440 |
| ttcaggttca gggggaggtg tgggaggttt tttcggatcc tctagagtcg atctgcaggc | 1500 |
| atgctagctt ggcgtaatca tggtcatagc tgtttcctgt gtgaaattgt tatccgctca | 1560 |
| caattccaca caacatacga gccgaagca taaagtgtaa agcctggggt gcctaatgag | 1620 |
| tgagctaact cacattaatt gcgttgcgct cactgcccgc tttccagtcg ggaaacctgt | 1680 |
| cgtgccagct gcattaatga atcggccaac gcgcggggag aggcggtttg cgtattgggc | 1740 |
| gctcttccgc ttcctcgctc actgactcgc tgcgctcggt cgttcggctg cggcgagcgg | 1800 |
| tatcagctca ctcaaaggcg gtaatacggt tatccacaga atcaggggat aacgcaggaa | 1860 |
| agaacatgtg agcaaaaggc cagcaaaagg ccaggaaccg taaaaaggcc gcgttgctgg | 1920 |
| cgttttccca taggctccgc cccctgacg agcatcacaa aaatcgacgc tcaagtcaga | 1980 |
| ggtggcgaaa cccgacagga ctataaagat accaggcgtt tcccctggaa gctccctcg | 2040 |
| tgcgctctcc tgttccgacc ctgccgctta ccggatacct gtccgccttt ctcccttcgg | 2100 |
| gaagcgtggc gctttctcat agctcacgct gtaggtatct cagttcggtg taggtcgttc | 2160 |

```
gctccaagct gggctgtgtg cacgaaccccc ccgttcagcc cgaccgctgc gccttatccg    2220
gtaactatcg tcttgagtcc aacccggtaa gacacgactt atcgccactg gcagcagcca    2280
ctggtaacag gattagcaga gcgaggtatg taggcggtgc tacagagttc ttgaagtggt    2340
ggcctaacta cggctacact agaaggacag tatttggtat ctgcgctctg ctgaagccag    2400
ttaccttcgg aaaaagagtt ggtagctctt gatccggcaa acaaaccacc gctggtagcg    2460
gtggtttttt tgtttgcaag cagcagatta cgcgcagaaa aaaaggatct caagaagatc    2520
ctttgatctt ttctacgggg tctgacgctc agtggaacga aaactcacgt taagggattt    2580
tggtcatgag attatcaaaa aggatcttca cctagatcct tttaaattaa aaatgaagtt    2640
ttaaatcaat ctaaagtata tatgagtaaa cttggtctga cagttaccaa tgcttaatca    2700
gtgaggcacc tatctcagcg atctgtctat ttcgttcatc catagttgcc tgactccccg    2760
tcgtgtagat aactacgata cgggagggct taccatctgg ccccagtgct gcaatgatac    2820
cgcgagaccc acgctcaccg gctccagatt tatcagcaat aaaccagcca gccggaaggg    2880
ccgagcgcag aagtggtcct gcaactttat ccgcctccat ccagtctatt aattgttgcc    2940
gggaagctag agtaagtagt tcgccagtta atagtttgcg caacgttgtt gccattgcta    3000
caggcatcgt ggtgtcacgc tcgtcgtttg gtatggcttc attcagctcc ggttcccaac    3060
gatcaaggcg agttacatga tcccccatgt tgtgcaaaaa agcggttagc tccttcggtc    3120
ctccgatcgt tgtcagaagt aagttggccg cagtgttatc actcatggtt atggcagcac    3180
tgcataattc tcttactgtc atgccatccg taagatgctt ttctgtgact ggtgagtact    3240
caaccaagtc attctgagaa tagtgtatgc ggcgaccgag ttgctcttgc ccggcgtcaa    3300
tacgggataa taccgcgcca catagcagaa ctttaaaagt gctcatcatt ggaaaacgtt    3360
cttcggggcg aaaactctca aggatcttac cgctgttgag atccagttcg atgtaaccca    3420
ctcgtgcacc caactgatct tcagcatctt ttactttcac cagcgtttct gggtgagcaa    3480
aaacaggaag gcaaaatgcc gcaaaaaagg gaataagggc gacacggaaa tgttgaatac    3540
tcatactctt cctttttcaa tattattgaa gcatttatca gggttattgt ctcatgagcg    3600
gatacatatt tgaatgtatt tagaaaaata aacaaatagg ggttccgcgc acatttcccc    3660
gaaaagtgcc acctgacgtc taagaaacca ttattatcat gacattaacc tataaaaata    3720
ggcgtatcac gaggcccttt cgtctcgcgc gtttcggtga tgacggtgaa aacctctgac    3780
acatgcagct cccggagacg gtcacagctt gtctgtaagc ggatgccggg agcagacaag    3840
cccgtcaggg cgcgtcagcg ggtgttggcg ggtgtcgggg ctggcttaac tatgcggcat    3900
cagagcagat tgtactgaga gtgcaccata tgcggtgtga ataccgcac agatgcgtaa    3960 ggagaaaata ccgcatcagg cgccattcgc cattcaggct gcgcaactgt tgggaagggc    4020
gatcggtgcg ggcctcttcg ctattacgcc agctggcgaa agggggatgt gctgcaaggc    4080
gattaagttg ggtaacgcca gggttttccc agtcacgacg ttgtaaaacg acggccagt    4139
```

<210> SEQ ID NO 15
<211> LENGTH: 4139
<212> TYPE: DNA
<213> ORGANISM: Artificial Sequence
<220> FEATURE:
<223> OTHER INFORMATION: Recombinant vector

<400> SEQUENCE: 15

```
gagttcgagc ttgcatgcct gcaggtcgtt acataactta cggtaaatgg cccgcctggc       60
```

```
tgaccgccca acgaccccg cccattgacg tcaataatga cgtatgttcc catagtaacg    120
ccaataggga ctttccattg acgtcaatgg gtggagtatt tacggtaaac tgcccacttg    180
gcagtacatc aagtgtatca tatgccaagt acgccccta ttgacgtcaa tgacggtaaa    240
tggcccgcct ggcattatgc ccagtacatg accttatggg actttcctac ttggcagtac    300
atctacgtat tagtcatcgc tattaccatg gtgatgcggt tttggcagta catcaatggg    360
cgtggatagc ggtttgactc acggggattt ccaagtctcc accccattga cgtcaatggg    420
agtttgtttt ggcaccaaaa tcaacgggac tttccaaaat gtcgtaacaa ctccgcccca    480
ttgacgcaaa tgggcggtag gcgtgtacgg tgggaggtct atataagcag agctcgttta    540
gtgaaccgtc agatcgcctg gagacgccat ccacgctgtt tgacctccaa tagaagacac    600
cgggaccgat ccagcctccg gactctagag gatccggtac tagaggaact gaaaaaccag    660
aaagttaact ggtaagttta gtcttttgt cttttatttc aggtcccgga tccggtggtg    720
gtgcaaatca aagaactgct cctcagtgga tgttgccttt acttctaggc ctgtacggaa    780
gtgttacttc tgctctaaaa gctgcggaat tgtacccgcg gcccaccat ggcatcaatg    840 ggccggttca tcttcgtgtc cttcggcctg ctggtggtgt tcctgagcct gtccggaaca    900
ggcgccgact gtccttccgg ctggtcctcc tacgagggcc actgctacaa gcccttaac    960 gagcccaaga ctgggctga cgccgaggcg ttctgcgcgc tgcagcccaa gcactcccac   1020
ctcgtgagct tccagtccgc cgaggaggcc gacttcgtgg tgaagctgac caggcccgcg   1080
ctggcggcca acctggtgtg gatgggcctg tccaacatct ggcacggctg taactggcag   1140
tggtccgacg gcgccaggct gaactacaag gactggcagg agcagtccga gtgtctggcc   1200
ttcaggggcg tgcacaccga gtggctgaac atggactgct cctccacctg ctccttcgtg   1260
tgcaagttca aggcctgaat ccagacatga taagatacat tgatgagttt ggacaaacca   1320
caactagaat gcagtgaaaa aaatgcttta tttgtgaaat ttgtgatgct attgctttat   1380
ttgtaaccat tataagctgc aataaacaag ttaacaacaa caattgcatt catttattgt   1440
ttcaggttca gggggaggtg tgggaggttt tttcggatcc tctagagtcg atctgcaggc   1500
atgctagctt ggcgtaatca tggtcatagc tgtttcctgt gtgaaattgt tatccgctca   1560
caattccaca acaatacga gccggaagca taaagtgtaa agcctgggt gcctaatgag   1620 tgagctaact cacattaatt gcgttgcgct cactgcccgc tttccagtcg ggaaacctgt   1680
cgtgccagct gcattaatga atcggccaac gcgcgggag aggcggtttg cgtattgggc   1740
gctcttccgc ttcctcgctc actgactcgc tgcgctcggt cgttcggctg cggcgagcgg   1800
tatcagctca ctcaaaggcg gtaatacggt tatccacaga atcaggggat aacgcaggaa   1860
agaacatgtg agcaaaaggc cagcaaaagg ccaggaaccg taaaaaggcc gcgttgctgg   1920 cgttttcca taggctccgc cccctgacg agcatcacaa aaatcgacgc tcaagtcaga   1980
ggtggcgaaa cccgacagga ctataaagat accaggcgtt tccccctgga agctccctcg   2040
tgcgctctcc tgttccgacc ctgccgctta ccggatacct gtccgccttt ctcccttcgg   2100
gaagcgtggc gctttctcat agctcacgct gtaggtatct cagttcggtg taggtcgttc   2160
gctccaagct gggctgtgtg cacgaacccc cgttcagcc cgaccgctgc gccttatccg   2220
gtaactatcg tcttgagtcc aacccggtaa gacacgactt atcgccactg gcagcagcca   2280
ctggtaacag gattagcaga gcgaggtatg taggcggtgc tacagagttc ttgaagtggt   2340
ggcctaacta cggctacact agaaggacag tatttggtat ctgcgctctg ctgaagccag   2400
ttaccttcgg aaaaagagtt ggtagctctt gatccggcaa acaaaccacc gctggtagcg   2460
```

```
gtggttttttt tgtttgcaag cagcagatta cgcgcagaaa aaaaggatct caagaagatc   2520
ctttgatctt ttctacgggg tctgacgctc agtggaacga aaactcacgt taagggattt   2580
tggtcatgag attatcaaaa aggatcttca cctagatcct tttaaattaa aaatgaagtt   2640
ttaaatcaat ctaaagtata tatgagtaaa cttggtctga cagttaccaa tgcttaatca   2700
gtgaggcacc tatctcagcg atctgtctat ttcgttcatc catagttgcc tgactccccg   2760
tcgtgtagat aactacgata cgggagggct taccatctgg ccccagtgct gcaatgatac   2820
cgcgagaccc acgctcaccg gctccagatt tatcagcaat aaaccagcca gccggaaggg   2880
ccgagcgcag aagtggtcct gcaactttat ccgcctccat ccagtctatt aattgttgcc   2940
gggaagctag agtaagtagt tcgccagtta atagtttgcg caacgttgtt gccattgcta   3000
caggcatcgt ggtgtcacgc tcgtcgtttg gtatggcttc attcagctcc ggttcccaac   3060
gatcaaggcg agttacatga tcccccatgt tgtgcaaaaa agcggttagc tccttcggtc   3120
ctccgatcgt tgtcagaagt aagttggccg cagtgttatc actcatggtt atggcagcac   3180
tgcataattc tcttactgtc atgccatccg taagatgctt ttctgtgact ggtgagtact   3240
caaccaagtc attctgagaa tagtgtatgc ggcgaccgag ttgctcttgc ccggcgtcaa   3300
tacgggataa taccgcgcca catagcagaa ctttaaaagt gctcatcatt ggaaaacgtt   3360
cttcggggcg aaaactctca aggatcttac cgctgttgag atccagttcg atgtaaccca   3420
ctcgtgcacc caactgatct tcagcatctt ttactttcac cagcgtttct gggtgagcaa   3480
aaacaggaag gcaaaatgcc gcaaaaaagg aataagggc gacacggaaa tgttgaatac   3540
tcatactctt cctttttcaa tattattgaa gcatttatca gggttattgt ctcatgagcg   3600
gatacatatt tgaatgtatt tagaaaaata acaaataggg gttccgcgc acatttcccc   3660 gaaaagtgcc acctgacgtc taagaaacca ttattatcat gacattaacc tataaaaata   3720
ggcgtatcac gaggcccttt cgtctcgcgc gtttcggtga tgacggtgaa aacctctgac   3780
acatgcagct cccggagacg gtcacagctt gtctgtaagc ggatgccggg agcagacaag   3840
cccgtcaggg cgcgtcagcg ggtgttggcg ggtgtcgggg ctggcttaac tatgcggcat   3900
cagagcagat tgtactgaga gtgcaccata tgcggtgtga ataccgcac agatgcgtaa   3960 ggagaaaata ccgcatcagg cgccattcgc cattcaggct gcgcaactgt tgggaagggc   4020
gatcggtgcg ggcctcttcg ctattacgcc agctggcgaa aggggggatgt gctgcaaggc   4080 gattaagttg ggtaacgcca gggttttccc agtcacgacg ttgtaaaacg acggccagt   4139
```

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
cccaccatgg catcaatggg ccggtttatc                                      30

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
gataaaccgg cccattgatg ccatggtggg                                          30

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
cccaccatgg catcaatggg gcgattcatc                                          30

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
gatgaatcgc cccattgatg ccatggtggg                                          30

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
ttatcatgtc tggattcagt agggcagcag                                          30

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
ctgctgccct actgaatcca gacatgataa                                          30

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
ttatcatgtc tggattcagg ccttgaactt                                          30

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
aagttcaagg cctgaatcca gacatgataa                                          30

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
ttatcatgtc tggattcaat atggcaggag         30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
ctcctgccat attgaatcca gacatgataa         30

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
ttatcatgtc tggattcatg ccttgaactt         30

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27
aagttcaagg catgaatcca gacatgataa         30

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
tccggcacag gcgctggact ggaggactgc         30

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
gcagtcctcc agtccagcgc ctgtgccgga         30

<210> SEQ ID NO 30
<211> LENGTH: 41
<212> TYPE: DNA
<213> ORGANISM: Artificial Sequence
<220> FEATURE:
<223> OTHER INFORMATION: Primer

<400> SEQUENCE: 30
tgggctgacg ccgaggcgtt ctgcgcgctg cagcccaagc a         41

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
gcgctgacca ggcccaggct gaaggccaac                                    30

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
gcgctgaccg cgcccaggct gaaggccaac                                    30

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
cccgcgctgg cggccaacct ggtgtggatg                                    30

<210> SEQ ID NO 34
<211> LENGTH: 41
<212> TYPE: DNA
<213> ORGANISM: Artificial Sequence
<220> FEATURE:
<223> OTHER INFORMATION: Primer

<400> SEQUENCE: 34
tgcttgggct gcagcgcgca gaacgcctcg gcgtcagccc a                       41

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
gccgacttcg tggtggcgct gaccaggccc                                    30

<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36
gggcgcggtc agcgccacca cgaagtcggc                                    30

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
ggccgccagc gcgggcctgg tcagcttcac                                    30

<210> SEQ ID NO 38
<211> LENGTH: 69
<212> TYPE: DNA
<213> ORGANISM: Calloselasma rhodostoma

<400> SEQUENCE: 38
atggggcgat tcatcttcgt gagcttcggc ttgctggtcg tgttcctctc cctgagtggt    60
actggagct                                                            69

<210> SEQ ID NO 39
<211> LENGTH: 69
<212> TYPE: DNA
<213> ORGANISM: Artificial Sequence
<220> FEATURE:
<223> OTHER INFORMATION: Designed Base Sequence based on Signal sequence
      of Rhodocytin beta subunit.

<400> SEQUENCE: 39
atgggccggt tcatcttcgt gtccttcggc ctgctggtgg tgttcctgag cctgtccgga    60
acaggcgcc                                                            69

<210> SEQ ID NO 40
<211> LENGTH: 66
<212> TYPE: DNA
<213> ORGANISM: Artificial Sequence
<220> FEATURE:
<223> OTHER INFORMATION: Designed Base Sequence based on Signal sequence
      of Rhodocytin beta subunit.

<400> SEQUENCE: 40
atgggccggt ttatcttcgt gagctttggc ctgctggtgg tgttcctgag cctgtccggc    60
acaggc                                                               66

<210> SEQ ID NO 41
<211> LENGTH: 2710
<212> TYPE: DNA
<213> ORGANISM: Artificial Sequence
<220> FEATURE:
<223> OTHER INFORMATION: Vector

<400> SEQUENCE: 41
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctggc ttaactatgc ggcatcaga gcagattgta ctgagagtgc    180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgagctcggt acctcgcgaa   420
tgcatctaga tatcggatcc cgggcccgtc gactgcagag gcctgcatgc aagcttggcg   480
taatcatggt catagctgtt tcctgtgtga aattgttatc cgctcacaat tccacacaac   540
atacgagccg gaagcataaa gtgtaaagcc tggggtgcct aatgagtgag ctaactcaca   600
ttaattgcgt tgcgctcact gcccgctttc cagtcgggaa acctgtcgtg ccagctgcat   660

```
taatgaatcg gccaacgcgc ggggagaggc ggtttgcgta ttgggcgctc ttccgcttcc    720
tcgctcactg actcgctgcg ctcggtcgtt cggctgcggc gagcggtatc agctcactca    780
aaggcggtaa tacggttatc cacagaatca ggggataacg caggaaagaa catgtgagca    840
aaaggccagc aaaaggccag gaaccgtaaa aaggccgcgt tgctggcgtt tttccatagg    900
ctccgccccc ctgacgagca tcacaaaaat cgacgctcaa gtcagaggtg gcgaaacccg    960
acaggactat aaagatacca ggcgtttccc cctggaagct ccctcgtgcg ctctcctgtt   1020
ccgaccctgc cgcttaccgg atacctgtcc gcctttctcc cttcgggaag cgtggcgctt   1080
tctcatagct cacgctgtag gtatctcagt tcggtgtagg tcgttcgctc caagctgggc   1140
tgtgtgcacg aaccccccgt tcagcccgac cgctgcgcct tatccggtaa ctatcgtctt   1200
gagtccaacc cggtaagaca cgacttatcg ccactggcag cagccactgg taacaggatt   1260
agcagagcga ggtatgtagg cggtgctaca gagttcttga agtggtggcc taactacggc   1320
tacactagaa gaacagtatt tggtatctgc gctctgctga agccagttac cttcggaaaa   1380
agagttggta gctcttgatc cggcaaacaa accaccgctg gtagcggtgg ttttttttgtt   1440
tgcaagcagc agattacgcg cagaaaaaaa ggatctcaag aagatccttt gatcttttct   1500
acggggtctg acgctcagtg gaacgaaaac tcacgttaag ggattttggt catgagatta   1560
tcaaaaagga tcttcaccta gatccttttta aattaaaaat gaagttttaa atcaatctaa   1620
agtatatatg agtaaacttg gtctgacagt taccaatgct taatcagtga ggcacctatc   1680
tcagcgatct gtctatttcg ttcatccata gttgcctgac tccccgtcgt gtagataact   1740
acgatacggg agggcttacc atctggcccc agtgctgcaa tgataccgcg agacccacgc   1800
tcaccggctc cagatttatc agcaataaac cagccagccg aagggccga gcgcagaagt   1860
ggtcctgcaa ctttatccgc ctccatccag tctattaatt gttgccggga agctagagta   1920
agtagttcgc cagttaatag tttgcgcaac gttgttgcca ttgctacagg catcgtggtg   1980
tcacgctcgt cgtttggtat ggcttcattc agctccggtt cccaacgatc aaggcgagtt   2040
acatgatccc ccatgttgtg caaaaaagcg gttagctcct tcggtcctcc gatcgttgtc   2100
agaagtaagt tggccgcagt gttatcactc atggttatgg cagcactgca taattctctt   2160
actgtcatgc catccgtaag atgcttttct gtgactggtg agtactcaac caagtcattc   2220
tgagaatagt gtatgcggcg accgagttgc tcttgcccgg cgtcaatacg ggataatacc   2280
gcgccacata gcagaacttt aaaagtgctc atcattggaa aacgttcttc ggggcgaaaa   2340
ctctcaagga tcttaccgct gttgagatcc agttcgatgt aacccactcg tgcacccaac   2400
tgatcttcag catcttttac tttcaccagc gtttctgggt gagcaaaaac aggaaggcaa   2460
aatgccgcaa aaaagggaat aagggcgaca cggaaatgtt gaatactcat actcttcctt   2520
tttcaatatt attgaagcat ttatcagggt tattgtctca tgagcggata catatttgaa   2580
tgtatttaga aaaataaaca aataggggtt ccgcgcacat ttccccgaaa agtgccacct   2640
gacgtctaag aaaccattat tatcatgaca ttaacctata aaaataggcg tatcacgagg   2700
ccctttcgtc                                                          2710
```

<210> SEQ ID NO 42
<211> LENGTH: 480
<212> TYPE: DNA
<213> ORGANISM: Artificial Sequence
<220> FEATURE:
<223> OTHER INFORMATION: Designed Base Sequence based on Signal sequence of Rhodocytin beta subunit and Rhodocytin alpha subunit gene.

-continued

<400> SEQUENCE: 42

```
atgggccggt ttatcttcgt gagctttggc ctgctggtgg tgttcctgag cctgtccggc    60
acaggcgctg gactggagga ctgcgacttc ggctggtccc cctacgacca gcactgctac   120
caggccttca cgagcagaa gacctgggac gaggccgaga gttctgcag gctcaggag    180 aacggcgccc atctggccag catcgagtcc aacggcgagg ccgacttcgt gagctggctc   240
atcagccaga aggacgagct ggccgacgag gactacgtgt ggatcggcct gagggctcag   300
aacaaggagc agcagtgctc ctccgagtgg tccgacggca gctccgtgtc ctacgagaac   360
ctgatcgacc tgcacaccaa gaagtgcggg ccctggaga agctgaccgg ctttcggaag   420
tgggtgaact actactgcga gcagatgcac gccttcgtgt gcaagctgct gccctactga   480
```

<210> SEQ ID NO 43
<211> LENGTH: 441
<212> TYPE: DNA
<213> ORGANISM: Artificial Sequence
<220> FEATURE:
<223> OTHER INFORMATION: [Beta S]-[Beta subunit] (R28A, K31A)

<400> SEQUENCE: 43

```
atgggccggt tcatcttcgt gtccttcggc ctgctggtgg tgttcctgag cctgtccgga    60
acaggcgccg actgtccttc cggctggtcc tcctacgagg ccactgcta caagcccttt   120 aacgagccca gaactgggc tgacgccgag gcgttctgcg cgctgcagcc caagcactcc   180
cacctcgtga gcttccagtc cgccgaggag gccgacttcg tggtgaagct gaccaggccc   240
aggctgaagg ccaacctggt gtggatgggc ctgtccaaca tctggcacgg ctgtaactgg   300
cagtggtccg acggcgccag gctgaactac aaggactggc aggagcagtc cgagtgtctg   360
gccttcaggg gcgtgcacac cgagtggctg aacatggact gctcctccac ctgctccttc   420
gtgtgcaagt tcaaggcctg a                                              441
```

<210> SEQ ID NO 44
<211> LENGTH: 441
<212> TYPE: DNA
<213> ORGANISM: Artificial Sequence
<220> FEATURE:
<223> OTHER INFORMATION: [Beta S]-[Beta subunit] (R56A)

<400> SEQUENCE: 44

```
atgggccggt tcatcttcgt gtccttcggc ctgctggtgg tgttcctgag cctgtccgga    60
acaggcgccg actgtccttc cggctggtcc tcctacgagg ccactgcta caagcccttt   120 aacgagccca gaactgggc tgacgccgag cggttctgca agctgcagcc caagcactcc   180
cacctcgtga gcttccagtc cgccgaggag gccgacttcg tggtgaagct gaccgcgccc   240
aggctgaagg ccaacctggt gtggatgggc ctgtccaaca tctggcacgg ctgtaactgg   300
cagtggtccg acggcgccag gctgaactac aaggactggc aggagcagtc cgagtgtctg   360
gccttcaggg gcgtgcacac cgagtggctg aacatggact gctcctccac ctgctccttc   420
gtgtgcaagt tcaaggcctg a                                              441
```

<210> SEQ ID NO 45
<211> LENGTH: 441
<212> TYPE: DNA
<213> ORGANISM: Artificial Sequence
<220> FEATURE:
<223> OTHER INFORMATION: [Beta S]-[Beta subunit] (K53A, R56A)

<400> SEQUENCE: 45

```
atgggccggt tcatcttcgt gtccttcggc ctgctggtgg tgttcctgag cctgtccgga    60
acaggcgccg actgtccttc cggctggtcc tcctacgagg ccactgcta caagcccttt   120 aacgagccca gaactgggc tgacgccgag cggttctgca agctgcagcc caagcactcc   180
cacctcgtga gcttccagtc cgccgaggag ccgacttcg tggtggcgct gaccgcgccc   240
aggctgaagg ccaacctggt gtggatgggc ctgtccaaca tctggcacgg ctgtaactgg   300
cagtggtccg acggcgccag gctgaactac aaggactggc aggagcagtc cgagtgtctg   360
gccttcaggg gcgtgcacac cgagtggctg aacatggact gctcctccac ctgctccttc   420
gtgtgcaagt tcaaggcctg a                                             441
```

<210> SEQ ID NO 46
<211> LENGTH: 441
<212> TYPE: DNA
<213> ORGANISM: Artificial Sequence
<220> FEATURE:
<223> OTHER INFORMATION: [Beta S]-[Beta subunit] (R58A, K60A)

<400> SEQUENCE: 46

```
atgggccggt tcatcttcgt gtccttcggc ctgctggtgg tgttcctgag cctgtccgga    60
acaggcgccg actgtccttc cggctggtcc tcctacgagg ccactgcta caagcccttt   120 aacgagccca gaactgggc tgacgccgag cggttctgca agctgcagcc caagcactcc   180
cacctcgtga gcttccagtc cgccgaggag ccgacttcg tggtgaagct gaccaggccc   240
gcgctggcgg ccaacctggt gtggatgggc ctgtccaaca tctggcacgg ctgtaactgg   300
cagtggtccg acggcgccag gctgaactac aaggactggc aggagcagtc cgagtgtctg   360
gccttcaggg gcgtgcacac cgagtggctg aacatggact gctcctccac ctgctccttc   420
gtgtgcaagt tcaaggcctg a                                             441
```

<210> SEQ ID NO 47
<211> LENGTH: 441
<212> TYPE: DNA
<213> ORGANISM: Artificial Sequence
<220> FEATURE:
<223> OTHER INFORMATION: [Beta S]-[Beta subunit] (R28A, K31A, K53A, R56A)

<400> SEQUENCE: 47

```
atgggccggt tcatcttcgt gtccttcggc ctgctggtgg tgttcctgag cctgtccgga    60
acaggcgccg actgtccttc cggctggtcc tcctacgagg ccactgcta caagcccttt   120 aacgagccca gaactgggc tgacgccgag gcgttctgcg cgctgcagcc caagcactcc   180
cacctcgtga gcttccagtc cgccgaggag ccgacttcg tggtggcgct gaccgcgccc   240
aggctgaagg ccaacctggt gtggatgggc ctgtccaaca tctggcacgg ctgtaactgg   300
cagtggtccg acggcgccag gctgaactac aaggactggc aggagcagtc cgagtgtctg   360
gccttcaggg gcgtgcacac cgagtggctg aacatggact gctcctccac ctgctccttc   420
gtgtgcaagt tcaaggcctg a                                             441
```

<210> SEQ ID NO 48
<211> LENGTH: 441
<212> TYPE: DNA
<213> ORGANISM: Artificial Sequence
<220> FEATURE:
<223> OTHER INFORMATION: [Beta S]-[Beta subunit] (R28A, K31A, R58A, K60A)

```
<400> SEQUENCE: 48
atgggccggt tcatcttcgt gtccttcggc ctgctggtgg tgttcctgag cctgtccgga    60
acaggcgccg actgtccttc cggctggtcc tcctacgagg gccactgcta caagcccttt   120
aacgagccca agaactgggc tgacgccgag gcgttctgcg cgctgcagcc caagcactcc   180 caccctcgtga gcttccagtc cgccgaggag gccgacttcg tggtgaagct gaccaggccc   240
gcgctggcgg ccaacctggt gtggatgggc ctgtccaaca tctggcacgg ctgtaactgg   300
cagtggtccg acggcgccag gctgaactac aaggactggc aggagcagtc cgagtgtctg   360
gccttcaggg gcgtgcacac cgagtggctg aacatggact gctcctccac ctgctccttc   420
gtgtgcaagt tcaaggcctg a                                             441
```

FUNCTION SUPPRESSION TYPE OF GENETICALLY-MODIFIED RHODOCYTIN MUTANT

CROSS REFERENCE TO RELATED APPLICATIONS

This application claims priority to Japan Patent Application No. 2016-094203, filed on May 9, 2016, which is incorporated by reference herein in its entirety.

TECHNICAL FIELD

The present invention relates to a function suppression type of genetically-modified rhodocytin mutant, more specifically, to a mutant rhodocytin lacking platelet aggregation ability.

BACKGROUND ART

Rhodocytin, also called aggretin, is a platelet aggregation-inducing protein isolated from a venom gland of *Calloselasma rhodostoma* (non-patent document 1). Since the rhodocytin acts to aggregate platelets and then coagulate blood, it has been used for many studies to elucidate a platelet activation mechanism.

The platelets are small discoid blood cells and are indispensable for hemostasis and wound healing. When collagen or the like binds to platelet surface receptors, a signaling pathways are stimulated, resulting that platelet aggregation and blood coagulation are triggered by the stimulation. The rhodocytin has greatly contributed to the discovery of C-type lectin-like receptor 2 (CLEC-2) which is one of the platelet surface receptors (non-patent document 2). CLEC-2 has been reported to be associated not only with the platelet aggregation but also with cancer metastasis, lymphangiogenesis, inflammatory response and HIV seeding. In order to develop agents useful for the treatment of diseases associated with the platelet aggregation, there is a need for a method for enabling the identification of an agent effective for blocking the responses of the platelet surface receptors and their signaling pathways. Thus, it is necessary to identify the platelet surface receptors. Therefore, the studies of ligands (such as rhodocytin) that bind to the platelet surface receptors are essential for developing the agents useful for the treatment of the diseases associated with the platelet aggregation as described above.

The rhodocytin is snake venom isolated from *Calloselasma rhodostoma*. On the basis of the crystal structure analysis of the rhodocytin, it has been found that the rhodocytin is a secretory protein being a heterotetramer composed of rhodocytin α subunits and rhodocytin β subunits (non-patent document 3).

It has been reported that each of the rhodocytin α subunit and rhodocytin β subunit was encoded by a corresponding independent gene, which was cloned (non-patent document 4).

PRIOR ART DOCUMENT(S)

Non-Patent Document

Non-Patent Document 1: Biochem Biophys Res Commun. 1998 Apr. 28; 245(3): 741-5.
Non-Patent Document 2: Blood. 2006 Jan. 15; 107(2): 542-9. Epub 2005 Sep. 20.
Non-Patent Document 3: Biochemistry. 2008 Jul. 29; 47(30): 7831-7. doi: 10.1021/bi800528t. Epub 2008 Jul. 3.
Non-Patent Document 4: Biochem Biophys Res Commun. 1999 Oct. 5; 263(3): 723-7.

SUMMARY OF THE INVENTION

Problem to be Solved by the Invention

Although an inhibitory action of CLEC-2 has been expected to be used as antiplatelet agents, anti-cancer metastatic drugs and the like, no useful inhibitors have not been reported yet. The present invention has been made in view of the above circumstances. An object of the present invention is to provide a mutant rhodocytin lacking platelet aggregation ability.

Means to Solve the Problem

When the inventors examined a function and structure of wild-type rhodocytin, it was found that rhodocytin having mutated amino acids at one or more specific positions interacts with CLEC-2, but does not cause the platelet aggregation. As a result of detailed examination, it was found that the number of the subunits of the rhodocytin having mutated amino acids at the one or more specific positions was lower than that of the wild-type rhodocytin. In addition, the wild-type rhodocytin has been reported to being a tetramer. However, in this experiment, it was found that the wild-type rhodocytin also is an octamer. On the basis of these findings, the present invention has been completed.

The present invention provides a mutant rhodocytin lacking platelet aggregation ability. This mutant rhodocytin does not cause platelet aggregation. The present invention also provides a structural gene encoding a subunit of a mutant rhodocytin lacking platelet aggregation ability. The structural gene encoding the subunit of the mutant rhodocytin lacking the platelet aggregation ability can be introduced into vectors. The present invention also provides a vector including a structural gene encoding a subunit of a mutant rhodocytin lacking platelet aggregation ability. By using the vector including the structural gene, a transformant can be prepared from host cells. The present invention also provides a transformant containing a vector including a structural gene encoding a subunit of a mutant rhodocytin lacking platelet aggregation ability. By using the transformant, a mutant rhodocytin can be obtained.

The present invention also provides a pharmaceutical composition including a mutant rhodocytin lacking platelet aggregation ability. By using the pharmaceutical composition, the mutant rhodocytin can be administered to a subject in need thereof.

The present invention further provides a method for inhibiting platelet aggregation by a platelet aggregating substance, comprising administering a pharmaceutical composition including a mutant rhodocytin lacking platelet aggregation ability to a subject in need thereof. In accordance with the method, the platelet aggregation by the platelet aggregating substance can be inhibited by administering the pharmaceutical composition to the subject in need thereof.

BRIEF DESCRIPTION OF DRAWINGS

FIGS. 9A to 9G show experimental results for inhibition tests of platelet aggregation caused by wild-type rhodocytin, using mutant rhodocytins.

FIG. 20A shows a sequence of SEQ ID NO: 42 ([βS]-[α subunit]).

FIG. 20B shows a sequence of SEQ ID NO: 2 ([βS]-[α subunit]).

FIG. 20C shows a sequence of SEQ ID NO: 43 ([βS]-[α subunit] (R28A and K31A)).

FIG. 20D shows a sequence of SEQ ID NO: 44 ([βS]-[α subunit] (R56A)).

FIG. 20E shows a sequence of SEQ ID NO: 45 ([βS]-[α subunit] (K53A and R56A)).

FIG. 20F shows a sequence of SEQ ID NO: 46 ([βS]-[α subunit] (R58A and K60A)).

FIG. 20G shows a sequence of SEQ ID NO: 47 ([βS]-[α subunit] (R28A, K31A, K53A and R56A)).

FIG. 20H shows a sequence of SEQ ID NO: 48 ([βS]-[α subunit] (R28A, K31A, R58A and K60A)).

DETAILED DESCRIPTION OF THE INVENTION

Figure 1:
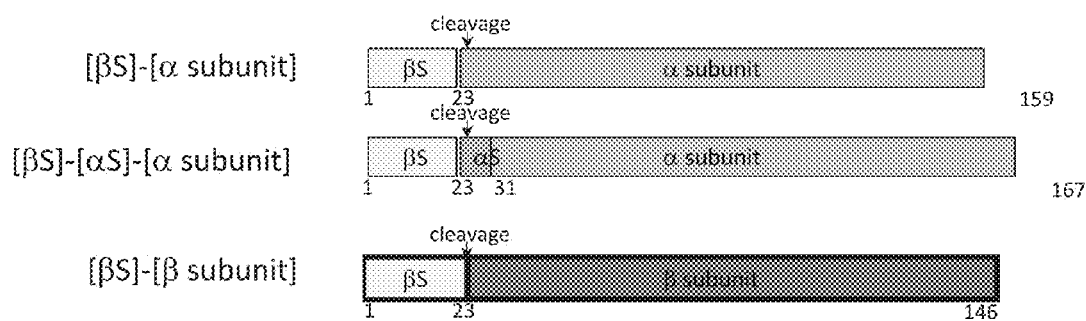
FIG. 1 shows a schematic diagram relating to designs for expression of wild-type rhodocytin α subunit and wild-type rhodocytin β subunit.
Figure 2:
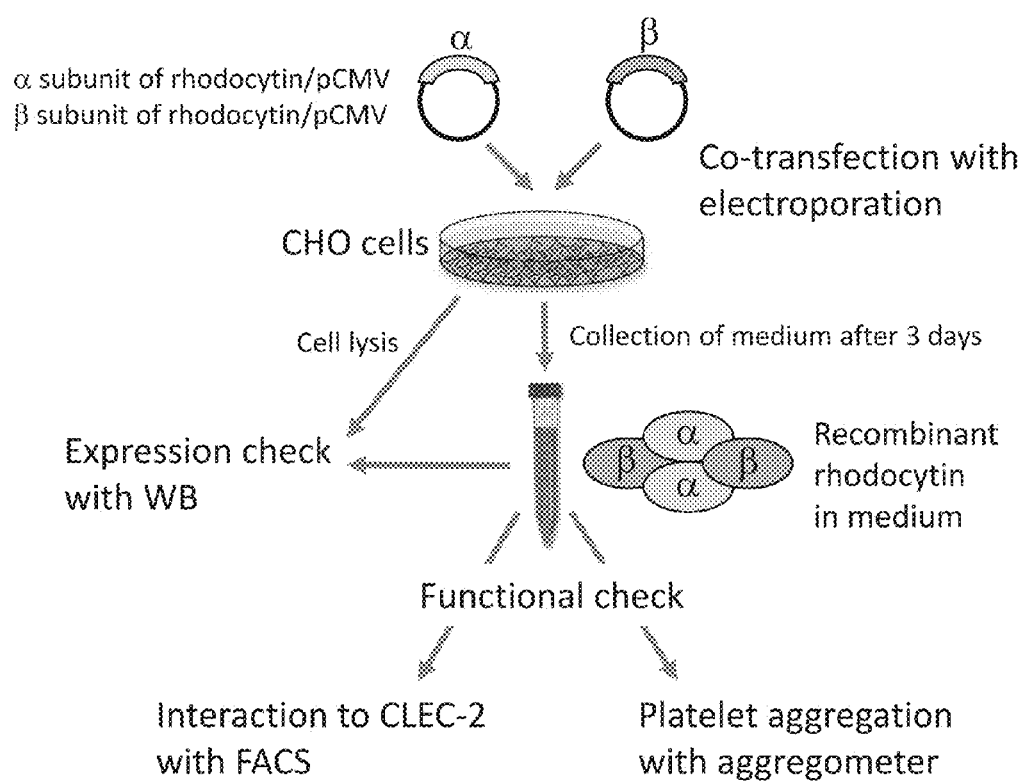
FIG. 2 shows a schematic diagram showing simple flows of a method for producing rhodocytin and a method for identifying platelet aggregation ability.

Embodiments of the present invention are described as follows. The following embodiments are illustrative, and the scope of the present invention is not limited to the following embodiments. Explanation about the same contents is omitted in order to avoid redundant description based on repetition. The singular forms "a", "an", and "the" are used herein to include plural referents unless the context clearly dictates otherwise.

Mutant Rhodocytin

In the present embodiment, a mutant rhodocytin lacking platelet aggregation ability refers to a rhodocytin lacking the platelet aggregation ability in which wild-type rhodocytin has. As described later in Examples, the mutant rhodocytin in the present embodiment lacks the platelet aggregation ability and therefore can be used, for example, for a functional analysis of a rhodocytin. Without being limited to a particular theory, it is believed that the (wild-type) rhodocytin triggers platelet aggregation by interacting with CLEC-2 present on platelets. In the present embodiment, "lacking platelet aggregation ability" means that the platelet aggregation ability of the mutant rhodocytin is preferably 10% or less, more preferably 5% or less, further preferably 2% or less, as compared with that of the wild-type rhodocytin. In certain embodiments, the platelet aggregation ability of the mutant rhodocytin does not aggregate the platelets at detectable level of a detector. The platelet aggregation ability of the rhodocytin can be evaluated by the change from absorbance of a platelet sample to absorbance of a platelet sample after the addition of the rhodocytin (e.g., 10 minutes after the addition of the rhodocytin), but it is not limited to this.

The mutant rhodocytin means a rhodocytin having an amino acid sequence different from that of the wild-type rhodocytin. In the present embodiment, the mutant rhodocytin means a rhodocytin having an amino acid mutation at one or more position involved in the loss of the platelet aggregation ability. The amino acid mutation can include, but are not limited to, an amino acid substitution occupied by an amino acid residue different from an original amino acid residue and an amino acid deletion in which an original amino acid residue is deleted. The amino acid mutation may also be an amino acid modification in which an original amino acid residue is modified with any compound. In certain embodiments, the mutant rhodocytin can interact with CLEC-2, but lacks the platelet aggregation ability.

The mutant rhodocytin of the present embodiment can be obtained cell-technologically by using a structural gene obtained by genetically modifying a structural gene encoding the wild-type rhodocytin. For example, by transfecting an appropriate expression vector containing a structural gene encoding the mutant rhodocytin into appropriate host cells, the mutant rhodocytin can be collected from the host cells or culture medium thereof. The mutant rhodocytin of the present embodiment can also be obtained by cloning the structural gene of the mutant rhodocytin from *Calloselasma rhodostoma* secreting the mutant rhodocytin. Furthermore, the mutant rhodocytin of the present embodiment can also be obtained by isolating and purifying the mutant rhodocytin from *Calloselasma rhodostoma* secreting the mutant rhodocytin.

In the present embodiment, the host cells used for preparing a transformant containing an expression vector are not particularly limited as long as the host cells can produce the mutant rhodocytin. Examples of the host cells include microbial cells, yeasts, animal cells, insect cells, plant cells and the like. The host cells are preferably the animal cells, more preferably CHO cells derived from a chinese hamster ovary tissue. The CHO cells, which are a cell line established in 1957, are used for research and production of therapeutic proteins because its growth is fast, its gene expression profile is stable and its protein productivity is high.

The mutant rhodocytin of the present embodiment includes a plurality of subunits having at least one α subunit and at least one β subunit. Since the mutant rhodocytin of the present embodiment includes the plurality of the subunits, a group of vectors containing the structural gene encoding each subunit may be prepared. In certain embodiments, an expression vector comprises the structural gene encoding the a subunit of the mutant rhodocytin and the structural gene encoding the β subunit of the mutant rhodocytin. By transfecting this expression vector into the host cells, the mutant rhodocytin can be obtained. In another embodiment, the structural gene encoding the α subunit of the mutant rhodocytin is inserted into one expression vector (e.g., a first expression vector), and the structural gene encoding the β subunit of the mutant rhodocytin is inserted into another expression vector (e.g., a second expression vector). By transfecting these expression vectors into the host cells, the mutant rhodocytin can be obtained. A vector type for the α subunit may be the same as or different from a vector type for the β subunit. These structural genes may also be derived from cDNAs of the subunits. In some embodiments, a codon usage of the structural gene encoding the mutant rhodocytin is changed to a suitable codon usage for the host cells to be used.

In order to secrete the mutant rhodocytin into medium, the expression vector containing the structural gene may contain a nucleotide sequence encoding a signal sequence capable of extracellular secretion. The signal sequence capable of the extracellular secretion is, but not particularly limited to, a signal sequence of rhodocytin β subunit. As an example, the signal sequence has the signal sequence of the rhodocytin β subunit shown in SEQ ID NO: 38, 39 or 40. The signal sequence is preferably the signal sequence of the rhodocytin β subunit shown in SEQ ID NO: 38. The signal sequence is more preferably the signal sequence of the rhodocytin β subunit shown in SEQ ID NO: 39.

The signal sequence capable of the extracellular secretion is:

(i) a nucleotide sequence having 95% or more sequence homology with the signal sequence of the rhodocytin β subunit shown in SEQ ID NO: 38, 39 or 40;

(ii) a nucleotide sequence in which one or several nucleotides are deleted, substituted, or added in the signal sequence of the rhodocytin β subunit shown in SEQ ID NO: 38, 39 or 40; or (iii) a nucleotide sequence capable of hybridizing, under stringent conditions, with a complementary sequence of the signal sequence of the rhodocytin β subunit shown in SEQ ID NO: 38, 39 or 40.

Identity score and homology score in this specification can be calculated by using the known programs such as BLAST. A nucleotide sequence having sequence homology with the nucleotide sequence shown in the sequence listing may have at least 95% sequence homology, such as 96% or more, 97% or more, 98% or more, 99% or more, 99.5% or more, 99.8% or more sequence homology.

In the present specification, the term "several nucleotides" in the expression "nucleotide sequence in which one or several nucleotides are deleted, substituted, or added" is, for example, 2 to 10 bases, 2 to 9 bases, 2 to 8 bases, 2 to 7 bases, 2 to 6 bases, 2 to 5 bases, 2 to 4 bases, 2 to 3 bases or 2 bases preferably. It is generally preferable that the number of bases for the deletion, the substitution or the addition is as small as possible. Any combination of base deletion, substitution and addition may exist at the same time. The base deletion, substitution and addition can be generated by using known techniques.

In the present specification, the term "stringent conditions" includes, for example, the following (1), (2) and the like:

(1) low ionic strength and high washing temperature (e.g., 0.015 M NaCl, 0.0015 M sodium citrate and 0.1% SDS at 50° C.); and (2) use of denaturants such as formamide during a hybridization (e.g., 0.1% bovine serum albumin, 0.1% Ficoll, 0.1% polyinyl pyrrolidone, 50 mM sodium phosphate buffer (pH 6.5), 750 mM NaCl and 75 mM sodium citrate in 50% formamide (vol/vol) at 42° C.). Another example includes 50% formamide, 5×SSC (0.75 M NaCl, 0.075 M sodium citrate), 50 mM sodium phosphate (pH 6.8), 0.1% sodium pyrophosphate, 5×Denhardt's solution, Sonicated Salmon sperm DNA (50 μg/ml), 0.1% SDS, 10% dextran sulfate, temperature 42° C., washing temperature 42° C., 0.2×SSC and 0.1% SDS. Those skilled in the art will appreciate that the stringent conditions can be suitably modified to obtain clear and detectable hybridization signals.

The expression vector in the present embodiment can be prepared by insertion and the like of a desired polynucleotide into a cloning vector. Examples of the above cloning vectors include a plasmid, a phage, a phagemid, a cosmid, a fosmid, an artificial chromosome and the like. Specifically, plasmids derived from *Escherichia coli* (for example, pBR322, pBR325, pUC12 and pUC13), yeast-derived plasmids (for example, pSH19 and pSH15), *Bacillus subtilis*-derived plasmids (for example, pUB110, pTP5 and pC194), animal cell expression plasmids (for example, pA1-11, pXT1, PRc/CMV, pRc/RSV and pcDNAI/Neo), bacteriophages such as lambda phage, vectors derived from viruses such as HIV, adenovirus, retrovirus, vaccinia virus and baculovirus, and artificial chromosomes can be used. These vectors may contain a component necessary for protein expression, such as a promoter, an origin of replication and an antibiotic resistance gene.

In this embodiment, the mutant rhodocytin comprises 2, 3 or 4 subunits. In Examples described later, the wild-type rhodocytin contained eight subunits (i.e., octamer), unlike the conventional reports. On the other hand, the number of subunits in the mutant rhodocytin of the present embodiment is smaller than that of the wild-type rhodocytin. The number of subunits can be evaluated using Blue-native PAGE described later. In certain embodiments, the mutant rhodocytin comprises one α subunit and one β subunit. In another embodiment, the mutant rhodocytin comprises one α subunit and two β subunits. In another embodiment, the mutant rhodocytin comprises two α subunits and one β subunit. In another embodiment, the mutant rhodocytin comprises two α subunits and two β subunits.

In the present embodiment, at least one of the subunits is a mutant subunit having one or more amino acid residues different from the wild-type subunit, whereby the number of subunits in the mutant rhodocytin is different from that of wild-type rhodocytin. The expression "amino acid different from the wild-type subunit" may mean an amino acid mutation. In certain embodiments, the amino acid mutation in the mutant subunit exists at least in a position where the number of subunits in the mutant rhodocytin is smaller than that of the wild-type rhodocytin.

The amino acid mutation in the mutant subunit can be generated by random mutation, preferably by mutating the amino acid at a specific position by PCR method. PCR is performed using a primer containing a mismatch codon designed to form a mutation at a target position to prepare a DNA fragment encoding the desired mutant subunit. The mutant subunit may be achieved by the substitution with any amino acid, preferably alanine, or by amino acid deletion. For example, when an amino acid mutation (alanine) is introduced by using the above-described PCR method, the mismatch codon is designed to be alanine.

The amino acid mutation may be present in the α subunit, in the β subunit, or in both. In certain embodiments, the mutant subunit includes a mutant α subunit having one or more amino acids different from the wild-type α subunit. In another embodiment, the mutant subunit includes a mutant β subunit having one or more amino acids different from the wild-type β subunit. In yet another embodiment, the mutant subunit includes the mutant α subunit having one or more amino acids different from the wild-type α subunit and the mutant β subunit having one or more amino acids different from the wild-type β subunit. In certain embodiments, the mutant β subunit has amino acid mutations at one or more positions selected from the group consisting of the positions [K53 and R56], [R58 and K60], and [R28 and K31] of the wild-type β subunit. In another embodiment, the mutant β subunit has amino acid mutations at either position [K53 and R56] or [R58 and K60] of the wild-type β subunit. In yet another embodiment, the mutant β subunit has amino acid mutations at the positions [K53 and R56] and [R58 and K60] of the wild-type β subunit.

In this embodiment, the mutant rhodocytin inhibits the platelet aggregation by a platelet aggregating substance. As described in Examples later, since the mutant rhodocytin in this embodiment inhibits the platelet aggregation by the platelet aggregating substance, the mutant rhodocytin can be used as an inhibitor for suppressing such platelet aggregation. The platelet aggregating substance may include in vivo substances and in vitro substances. In certain embodiments, the platelet aggregating substance interacts with CLEC-2. In another embodiment, the platelet aggregating substance competes with the mutant rhodocytin for the interaction with CLEC-2. In certain embodiments, the platelet aggregating substance is selected from the group consisting of thrombin, collagen, thromboxane A2, ADP, adrenaline, noradrenaline, serotonin, fucoidan, rhodocytin and podoplanin. In another embodiment, the platelet aggregating substance is selected from the group consisting of fucoidan, rhodocytin and podoplanin. In yet another embodiment, the platelet aggregating substance is selected from the group consisting of rhodocytin and podoplanin.

In this embodiment, the mutant rhodocytin inhibits cancer metastasis. As described in Examples later, since the mutant rhodocytin in the present embodiment can suppress the cancer metastasis, the mutant rhodocytin can be used as an inhibitor for suppressing the cancer metastasis. In certain embodiments, the cancer metastasis involves the platelet aggregating substance. In another embodiment, the cancer metastasis involves podoplanin. In yet another embodiment, the cancer metastasis is hematogenous metastasis. The hematogenous metastasis means that the cancer cells are metastasized by blood flow, and then metastatic lesions are easily formed in organs (e.g., lungs and liver) with a high flow rate of the blood flow. In certain embodiments, the cancer metastasis is derived from carcinoma and/or sarcoma. In another embodiment, the cancer metastasis is at least one selected from the group consisting of lung metastasis, liver metastasis, brain metastasis, bone metastasis and peritoneal metastasis (peritoneal dissemination).

Pharmaceutical Composition Having Mutant Rhodocytin

In this embodiment, a pharmaceutical composition having a mutant rhodocytin lacking platelet aggregating ability is provided. By using this pharmaceutical composition, the mutant rhodocytin lacking the platelet aggregating ability can be administered to a subject in need thereof. In certain embodiments, the pharmaceutical composition is administered to inhibit or prevent the platelet aggregation based on the platelet aggregating substance. In another embodiment, the pharmaceutical composition is administered to inhibit or prevent the cancer metastasis.

When the mutant rhodocytin is used as the pharmaceutical composition, the pharmaceutical composition may be prepared by using a mutant rhodocytin crystal. In the case of preparing injectable solution using the pharmaceutical composition containing the mutant rhodocytin, a pH adjuster, a buffering agent, a stabilizer, a solubilizing agent and the like may be added, if necessary.

The pharmaceutical composition, whether administered alone or in combination with other therapeutic agents, is administered in an effective amount to inhibit or prevent the platelet aggregation and/or the cancer metastasis based on the platelet aggregating substance. However, the total dose of the mutant rhodocytin is determined by attending physicians within the scope of appropriate medical judgment. The effective amount for the subject will depend on the severity, age, body weight, general health, sex and diet of the subject; time of administration; route of administration; rate of excretion or degradation of the mutant rhodocytin; duration of treatment; and drugs used in combination with or concurrently with the pharmaceutical composition. The dose of the pharmaceutical composition may not be constant in each administration. For example, it may be administered at a dose lower than a dose required to achieve a desired effect, and then the dose may be gradually increased until the desired effect is obtained.

If necessary, an effective dose per day may be divided into multiple doses depending on the purpose of administration. Those skilled in the art would be able to easily optimize the effective dose and concomitant dosage regimen depending on good medical practice and clinical symptoms of individual subjects.

The dose per day (daily dose) of the pharmaceutical composition may be in the range between two points selected from the group consisting of 0.01, 0.05, 0.1, 0.5, 1, 5, 10, 50, 100, 150 and 200 mg of the mutant rhodocytin/kg of body weight. Administration methods include intravenous, intraperitoneal, subcutaneous, intramuscular, topical, parenteral, intranasal or intradermal administration. The pharmaceutical composition is continuously administered over a certain period of time, for example, 3 days or more, preferably 1 week or more, more preferably 2 weeks or more, further preferably 1 month or more, 6 months or 1 year or more. The pharmaceutical composition may be administered daily, but the pharmaceutical composition is not necessary to be administered daily as long as the administration is performed continuously during the period. The pharmaceutical composition may be administered once a day in a daily dose or may be administered two or more times a day in several divided doses. The administration of the pharmaceutical composition may be terminated by a judgment made by medical doctors or may be terminated by subject's own judgment.

Method for Inhibiting Platelet Aggregation by Platelet Aggregating Substance

In this embodiment, there is provided a method for inhibiting platelet aggregation by platelet aggregating substance including administering a pharmaceutical composition having a mutant rhodocytin lacking platelet aggregating ability to a subject in need thereof. When the pharmaceutical composition is administered to the subject, dose may vary depending on conditions such as severity of symptoms, age, body weight, PSA value, urine flow rate, health condition and the like of the subject. Generally, the pharmaceutical composition may be administered once or more a day with the above-mentioned dosage and usage regimen, and the number and amount of the administration may be appropriately increased or decreased according to the above-mentioned conditions.

The term "subject" in this embodiment refers to any mammal including, e.g., humans and livestock animals, pet animals, zoo animals and sports animals such as dogs, cats, cows, pigs, horses, sheep, rabbits, mice and the like. In certain embodiments, the subject is human.

Method for Producing Recombinant Cells Producing Mutant Rhodocytin

In the present embodiment, recombinant cells producing the mutant rhodocytin can be prepared by introducing the above-described expression vector into the host cells and obtaining transformants thereof.

Ready-made kits or known methods for introducing genes can be used in order to introduce the above-mentioned vector into the host cells and obtaining the transformants thereof. The expression vector containing the structural gene of the α subunit and the expression vector containing the structural gene of the β subunit may be introduced into the host cells simultaneously or separately.

In this specification, as techniques of molecular biology (e.g., techniques such as cloning, plasmid extraction, DNA fragment cleavage, ligation, hybridization, site-specific mutagenesis, PCR and Western blotting), well-known ordinary methods can be used. These methods can be found in Sambrook, J., Fritsch, E. F., and Maniatis, T., "Molecular Cloning A Laboratory Manual, Second Edition", Cold Spring Harbor Laboratory Press, (1989).

Method for Producing Mutant Rhodocytin

The method for producing the mutant rhodocytin in the present embodiment includes steps of culturing the recombinant cells and collecting the mutant rhodocytin.

The step of culturing the recombinant cells in the method for producing the mutant rhodocytin of the present embodiment is not particularly limited as long as the recombinant cells of the present embodiment can be cultured. For example, well-known methods can be used.

The step of collecting the mutant rhodocytin in the method for producing the mutant rhodocytin of the present embodiment is not particularly limited as long as the mutant rhodocytin can be obtained from the recombinant cells. For example, well-known methods can be used. As an example, a method for obtaining culture medium used in culturing the recombinant cells by a syringe or the like, a method for obtaining the supernatant of the culture medium used in culturing the recombinant cells by centrifugation or a method of disrupting the recombinant cells by cell lysis solution or ultrasonic wave to obtain the mutant rhodocytin can be used. Also, the mutant rhodocytin may be purified by gel filtration and ion exchange.

Analysis Method

The expression of the mutant rhodocytin α subunit protein and the mutant rhodocytin β subunit protein. A method for evaluating the expression of the mutant rhodocytin α subunit protein and the mutant rhodocytin β subunit protein in this embodiment may be, but not particularly limited to, known methods. For example, Western blotting is included. Using the Western blotting, proteins, for example, in culture medium used in culturing cells into which a gene was introduced, or cell lysis solution derived from the cells can be evaluated. The Western blotting may be a standard Western blotting on the basis of commercially available experimental protocols and the like.

When the Western blotting to the rhodocytin was performed on SDS-PAGE, two bands, the mutant rhodocytin α subunit protein and the mutant rhodocytin β subunit protein, can be detected. As described in later Examples, the mutant rhodocytin is composed of the α subunit and β subunit. Thus, when disulfide bonds between the mutant rhodocytin α subunit protein and the mutant rhodocytin β subunit protein are cleaved by SDS sample buffer containing a reducing agent (e.g., mercaptoethanol and dithiothreitol), two bands can be detected.

Measurement of Platelet Aggregation Ability

As a method for measuring the platelet aggregation ability in this embodiment, known methods can be used. For example, the platelet aggregation ability can be measured by using a platelet aggregation ability measuring apparatus. Mouse or human washed platelets prepared are used to mix with the sample and then measure aggregation rate over time for a certain period.

Since the mutant rhodocytin obtained from the recombinant cells in this embodiment lacks the platelet aggregation ability, the mutant rhodocytin can be used as an antagonist against platelet surface receptors, for developing a drug useful for treating diseases associated with the platelet aggregation or as an experimental reagent for identifying an effective agent for inhibiting reactions of signaling pathways.

The above-described method for the production can also be applied to the wild-type rhodocytin.

Reagents, Diagnostic Agents and Kits

The mutant rhodocytin or a polynucleotide or vector encoding the mutant rhodocytin according to this embodiment can be used, produced or sold as reagents, diagnostic agents or kits including the above. These reagents, diagnostic reagents, or kits can be used, for example, as the antagonists against the platelet surface receptors and reagents to search inhibitors for inhibiting the reactions of the signaling pathways related to the platelet aggregation.

Note that, the above kit may include an instruction for describing a method of use or an example of use of the rhodocytin and the like according to the present embodiment, the document describing the location of the instruction, an antibody recognizing the rhodocytin according to this embodiment or various buffers.

EXAMPLE

Hereinafter, the present invention will be further described with reference to examples, but the present invention is not limited thereto.

Example 1

Preparation of Genetic Recombination Vector Containing α and β Subunit Genes of Wild-Type Rhodocytin Nucleotide sequences used in the Examples were designed based on gene sequences of α and β subunits of the rhodocytin described in Non-Patent Document 4 (Table 1). By entrusting to GENEWIZ Japan branch office, polynucleotides were synthesized based on the designed nucleotide sequences, and each synthesized polynucleotide was introduced into the corresponding pUC57-Amp vector (SEQ ID NO: 41)(GENEWIZ). The obtained recombinant vectors were shown in Table 2.

TABLE 1

| Name | SEQ ID NO |
|---|---|
| [βS]-[αS]-[α subunit] | SEQ ID NO: 1 |
| [βS]-[β subunit] | SEQ ID NO: 2 |
| Original [βS]-[α subunit] | SEQ ID NO: 3 |
| Original [βS]-[β subunit] | SEQ ID NO: 4 |

TABLE 2

| Name | Description |
|---|---|
| [βS]-[αS]-[α subunit]/pUC57-Amp | SEQ ID NO: 1 was introduced into the pUC57-Amp vector. |
| [βS]-[β subunit]/pUC57-Amp | SEQ ID NO: 2 was introduced into the pUC57-Amp vector. |
| Original [βS]-[α subunit]/pUC57-Amp | SEQ ID NO: 3 was introduced into the pUC57-Amp vector. |
| Original [βS]-[β subunit]/pUC57-Amp | SEQ ID NO: 4 was introduced into the pUC57-Amp vector. |

Using the above recombinant vectors and the pCMV vectors (Stratagene), the recombinant vectors described in Table 3 were prepared. Experiments were conducted with reference to the Overlap Extension PCR cloning method (Biotechniques. 2010 June; 48 (6): 463-465.).

Using the recombinant vectors and the pCMV vectors (Stratagene) as templates, PCR products were obtained by PCR using primers listed in Table 3. The PCR method using Q5 High-Fidelity DNA polymerase (New England Biolab) was performed using a thermal cycler Veriti 200 (Applied Biosystems) with the following PCR reaction profile: 25 cycles each at 98° C. for 30 seconds, at 55° C. for 30 seconds, and at 72° C. for 3 minutes.

5 μL of each of PCR products obtained by using the recombinant vectors as templates and 1 μL of each of PCR products obtained by using the pCMV vectors as templates were mixed. Each mixture was transfected into 100 μL of *Escherichia coli* DH5α competent cell solution by using heat shock method and then the transfected cells were plated on LB agar medium with 100 μg/mL of Ampicillin.

Based on Sambrook, J., Fritsch, E F, and Maniatis, T., "Molecular Cloning A Laboratory Manual, Second Edition", Cold Spring Harbor Laboratory Press, (1989), the competent cells were prepared and the heat shock was performed. The recombinant vectors were obtained from the transfected *E. coli* using QIAGEN Plasmid Maxi Kit (QIAGEN).

Also, using the recombinant vectors described in Table 3, recombinant vectors described in Table 4 were prepared. PCR products were obtained by inverse PCR method using the recombinant vectors described in Table 3 as templates and primers listed in Table 4. The conditions of the inverse PCR method are the same as those of the above PCR method. 6 μL of each of the obtained PCR products was transfected into 100 μL of *E. coli* DH5α competent cell solution by using the heat shock method and then the transfected cells were plated on LB agar medium with 100 μg/mL of Ampicillin. Recombinant vectors were obtained from the transfected *E. coli* by using the QIAGEN Plasmid Maxi Kit (QIAGEN).

Using order sequence analysis service (Macrogene Japan), it was evaluated that there were no defection, substitution or addition in sequences of the α and β subunit genes of the rhodocytins in the recombinant vectors as compared to the designed nucleotide sequences.

TABLE 3

| Prepared recombinant vector | SEQ ID NO | Template | Primer 1 | Primer 2 |
|---|---|---|---|---|
| [βS]-[α3S]-[α subunit]/pCMV | 5 | [βS]-[α3S][α subunit]/pUC57-Amp | 5'-CCCACCATGGCATC AATGGGCCGGTTTATC-3' (SEQ ID NO: 16) | 5'-TTATCATGTCTGGA TTCAGTAGGGCAGCA G-3' (SEQ ID NO: 20) |
| | | pCMV | 5'-GATAAACCGGCCCA TTGATGCCATGGTGGG-3' (SEQ ID NO: 17) | 5'-CTGCTGCCCTACT GAATCCAGACATGAT AA-3' (SEQ ID NO: 21) |
| [βS]-[β subunit]/pCMV | 6 | [βS]-[β subunit]/pUC57-Amp | 5'-CCCACCATGGCATC AATGGGCCGGTTTATC-3' (SEQ ID NO: 16) | 5'-TTATCATGTCTGGA TTCAGGCCTTGAACT T-3' (SEQ ID NO: 22) |
| | | pCMV | 5'-GATAAACCGGCCCA TTGATGCCATGGTGGG-3' (SEQ ID NO: 17) | 5'-AAGTTCAAGGCCT GAATCCAGACATGAT AA-3' (SEQ ID NO: 23) |

TABLE 3-continued

| Prepared recombinant vector | SEQ ID NO | Template | Primer 1 | Primer 2 |
|---|---|---|---|---|
| Original [βS]-[α subunit]/ pCMV | 7 | Original [βS]-[α subunit]/ pUC57-Amp pCMV | 5'-CCCACCATGGCATC AATGGGGCGATTCATC-3' (SEQ ID NO: 18)<br><br>5'-GATGAATCGCCCCA TTGATGCCATGGTGGG-3' (SEQ ID NO: 19) | 5'-TTATCATGTCTGGA TTCAATATGGCAGGA G-3' (SEQ ID NO: 24)<br><br>5'-CTCCTGCCATATTG AATCCAGACATGATA A-3' (SEQ ID NO: 25) |
| Original [βS]-[β subunit]/ pCMV | 8 | Original [βS]-[β subunit]/ pUC57-Amp pCMV | 5'-CCCACCATGGCATC AATGGGGCGATTCATC-3' (SEQ ID NO: 18)<br><br>5'-GATGAATCGCCCCA TTGATGCCATGGTGGG-3' (SEQ ID NO: 19) | 5'-TTATCATGTCTGGA TTCATGCCTTGAACT T-3' (SEQ ID NO: 26)<br><br>5'-AAGTTCAAGGCAT GAATCCAGACATGAT AA-3' (SEQ ID NO: 27) |

TABLE 4

| Prepared recombinant vector | SEQ ID NO | Template | Primer 1 | Primer 2 |
|---|---|---|---|---|
| [βS]-[α subunit]/ pCMV | 9 | [βS]-[αS]-α subunit]/ pCMV | 5'-TCCGGCACAGG CGCTGGACTGGAG GACTGC-3' (SEQ ID NO: 28) | 5'-GCAGTCCTCCA GTCCAGCGCCTGT GCCGGA-3' (SEQ ID NO: 29) |

Example 2

Preparation of Recombinant Cells Containing Expression Vector Using CHO Cells as Host Cells Culture Conditions CHO cells were used for protein expression. Culture conditions are as follows: the CHO cells were added to 15 cm diameter culture dishes having 25 mL of serum DMEM medium (Dulbecco's Modified Eagle's Medium (DMEM, Life Technologies) including 10% fetal bovine serum (FBS, Life Technologies), 1% P/S solution (10,000 units/mL Penicillin G, 10,000 µg/mL streptomycin sulfate); and the CHO cells in the dishes were cultured at 37° C. under 5% $CO_2$ until the CHO cells had 100% confluency in the 15 cm diameter dish. The culture conditions of the CHO cells after gene transfection were also the same as the above culture conditions.

Production of Competent Cells for Transfection into CHO Cells by Electroporation Method Culture media in each dish, used in culturing the CHO cells which became 100% confluency in 15 cm diameter dish, were discarded and the cells were washed once with 15 ml of 1×PBS per one culture dish. 2 ml of Trypsin-EDTA-Na solution (the mixture of 0.25% (w/v) of trypsin solution and 1 mM EDTA-Na solution) per one culture dish was added to each dish. After the Trypsin-EDTA-Na solution has been distributed throughout the culture dishes, the Trypsin-EDTA-Na solution in each dish was collected and the culture dishes were incubated at 37° C. for 2 minutes.

After the incubation, the CHO cells in each dish were suspended in a solution containing 20 mL of DMEM medium and 0.2 mL of P/S solution. The suspension in each dish was collected in 50 mL Falcon tube and centrifuged at 1,000 rpm for 5 minutes at room temperature (about 25° C.). After discarding the supernatant in each tube, 0.3 mL of Cytomix solution (120 mM KCl, 0.15 mM $CaCl_2$, 10 mM $K_2HPO_4$, 10 mM $KH_2PO_4$, 25 mM HEPES, 2 mM EGTA, 5 mM $MgCl_2$, 2 mM ATP, 5 mM glutathione) was added to each tube to resuspend the cells. The number of the CHO cells in this state was counted and adjusted by adding the Cytomix solution so that the number of the CHO cells was $2.5 \times 10^7$ cells/ml (as a guide, volume which can be obtained from 15 cm diameter culture dish is usually 0.5 to 0.6 ml).

Electroporation

40 µg of each of the recombinant vectors selected from Tables 3 and 4 was added to a cuvette for electroporation (Cell Projects, EP-104, GAP: 4 mm) in order to obtain the CHO cells listed in Table 5. Further, 400 µL of each CHO cell suspension adjusted to $2.5 \times 10^7$ cells/ml was added to the cuvette. After the cuvettes were capped and mixed by inversion, the cuvettes were incubated for 10 minutes at room temperature. A BIO-RAD GENE PULSERR II Electroporation System (BIO-RAD) was used as an electroporation system. The electroporation was performed using 250 mV and 950 µF as gene transfection condition. After the electroporation, the cuvettes were incubated on ice for 10 minutes. Then, 13 mL serum DMEM was prepared in 10 cm diameter culture dishes. The electroporated CHO cells in each cuvettes were added to the culture dishes and cultured overnight. The culture media in each dish was removed and the cells were washed once with 15 mL of 1×PBS per one culture dish. After that, 13 mL of Opti-MEM medium (Life Technologies) was added to each culture dish and the culture was continued. The obtained recombinant cells are shown in Table 5.

TABLE 5

| Recombinant cell number | Recombinant vector possessed by host cell | Host cell |
|---|---|---|
| 1 | [βS]-[α subunit]/pCMV<br>[βS]-[β subunit]/pCMV | CHO cell |
| 2 | Original [βS]-[α subunit]/pCMV<br>Original [βS]-[β subunit]/pCMV | CHO cell |

Example 3

Evaluation of Protein Expression by Western Blotting Method

In order to evaluate the expression of the rhodocytins in the recombinant cells, Western blotting method was performed.

Preparation of Culture Medium of Recombination Cells

After culturing the recombinant cells obtained in Example 2 in the Opti-MEM medium for 72 hours, the culture media were collected and centrifuged at 3,000 rpm for 30 minutes to remove floating cells and the like. The culture media were stored at −80° C. as needed. The culture media used in culturing the recombinant cells were centrifuged at 15,000 rpm for 30 minutes at 4° C., and the culture media were collected.

Preparation of Cell Lysate of Recombinant Cells

After the culture collection, the recombinant cells were washed twice with 1× ice-cold PBS. Cell lysis buffer (1% NP 40, 150 mM NaCl, 10 mM Tris, 1 mM $Na_3VO_3$, 1 mM EGTA, 1 mM EDTA, 1 µg/mL leupeptin, 1 µg/mL aprotinin, 1 µg/mL pepstatin and 1 mM PMSF, at pH 7.5) was added to the cells, obtaining cell lysates. The additional cell lysis buffer was used to dilute the cell lysate, as needed.

Western Blotting Method

The culture media used in culturing the recombinant cells were diluted by adding the Opti-MEM medium as needed. 20 µL of SDS sample buffer was added to the culture media used in culturing the prepared recombinant. After that, the electrophoresis by SDS-PAGE was performed, and proteins included in a gel subjected to the electrophoresis were transferred to a PVDF membrane. One of more rhodocytins on the PVDF membrane were detected with ECL Prime Western Blotting Detection System (GE Healthcare Life Science) using anti-rhodocytin antibody (rabbit polyclonal antibody) as a primary antibody and HRP-labeled rabbit IgG as a secondary antibody. Images were obtained in High Resolution mode using ImageQuant LAS 4000 mini (GE Healthcare Life Science). Bands for low exposure were taken with an exposure time of 2 minutes, and bands for high exposure were taken with an exposure time of 10 minutes.

The expression of the rhodocytin α subunit and rhodocytin β subunit protein was evaluated using the culture media used in culturing the above recombinant cells. The results are shown in FIG. 3.

Figure 3:
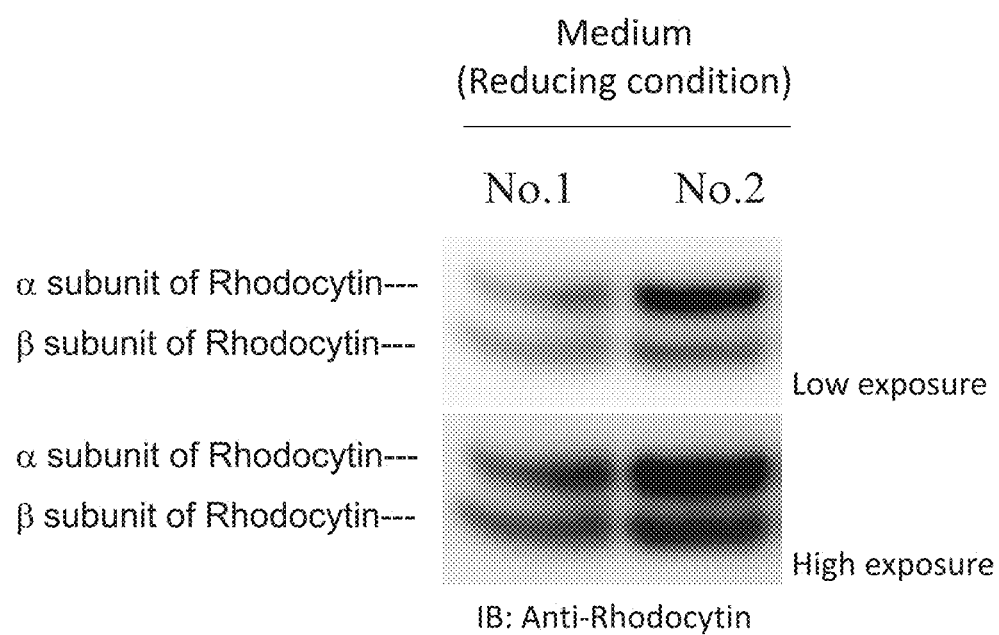
FIG. 3 shows results of Western blot tests in Example 3.

With reference to FIG. 3, band intensity of the rhodocytin α subunit protein and rhodocytin β subunit protein in the 4-fold diluted culture medium derived from recombinant cell No. 1 was stronger than that derived from recombinant cell No. 2. That is, rhodocytin producing ability of recombinant cell No. 1 is higher than that of recombinant cell No. 2.

Example 4

Evaluation of Platelet Aggregation Ability
Preparation of Washed Platelets from Mouse 6 to 8-week old C57BL/6 mice (wild-type) or 6 to 8-week old C57BL/6 (Clec1b (fl/fl) PF4-Cre mice (platelet CLEC-2 knockout mice) (J Biol Chem. 2012 Jun. 22; 287 (26): 22241-22252.)) were given general anesthetic by diethyl ether inhalation and cut open abdominal sections of the mice. 900 µL of blood was collected from a postcaval vein in the abdominal of each mouse using 1 mL syringe with a 25 G needle, filled preliminarily with 100 µL of acid citrate dextrose solution (ACD solution: 2.5% sodium citrate, 1.5% citric acid and 2% glucose) as an anticoagulant.

The collected blood in each mouse was transferred to 2 mL tube. 900 µL of Calcium-Freen modified Tyrode buffer (CFT solution: 137 mM NaCl, 11.9 mM $NaHCO_3$, 0.4 mM $NaH_2PO_4$, 2.7 mM KCl, 1.1 mM $MgCl_2$ and 5.6 mM glucose at pH 7.4) and 100 µL of ACD solution warmed previously to 37° C. were added to the above tubes, and then, the tubes were mixed by inversion. The tubes were centrifuged at 100 G for 10 minutes at room temperature by using an angle rotor centrifuge. Supernatant in each tube was transferred to another 2 mL tube.

The tube from which the supernatant in each tube was removed were further centrifuged at room temperature. Supernatant in each tube was transferred to 2 mL tube containing the initially-transferred supernatant. Then, 2 µL of 1 µg/µL Prostaglandin I2 (PGI2) solution was added to each 2 mL tube containing the supernatant. Each tube was mixed by inversion, and centrifuged at 2,300 rpm for 10 minutes at room temperature with a swing rotor centrifuge.

Precipitated platelets was obtained by removing the supernatant from each tube, and resuspended with 215 µL of CFT solution. After 15 µL of the resuspension solution in each tube was collected, the collected solution was diluted to 10-fold with 135 µL of the CFT solution. The number of platelets in the diluted solution was counted with a multi-item automatic blood cell analyzer XE-2100 (Sysmex Corporation). Based on the obtained number of the platelets, each of the resuspension solutions was diluted with the CFT solution so as to be $20×10^4$ PLT/µL, obtaining sample solutions. The sample solutions were used for measuring the platelet aggregation ability.

The multi-item automatic blood cell analyzer XE-2100 is a blood cell analyzer set for human. Although an optical method (PLT-O) and an impedance method (PLT-I) are known as counting methods, PLT-O was used for the counting of mouse platelets, because the mouse platelets are smaller than the human platelets.

Preparation of Washed Platelets from Human

Blood was drawn from a median cubital vein of a healthy donor. In order to prevent coagulation, 1 volume of 3.8% sodium citrate was mixed with 9 volumes of blood. The blood sample was centrifuged at 1,100 rpm for 10 minutes at room temperature with the swing rotor centrifuge to precipitate red blood cells and white blood cells. Supernatant of the centrifuged blood sample was collected to obtain platelet-rich plasma (PRP).

Further, ACD and PGI2 were mixed with PRP so that a final concentration of ACD was 15% and a final concentration of PGI2 was 1 µM. The mixture was centrifuged at 2,500 rpm for 10 minutes at room temperature with the swing rotor centrifuge to precipitate the platelets.

After discarding the supernatant of the centrifuged mixture, the liquid mixture of 5 mL of the CFT solution with 750 µL of the ACD solution was added to the precipitated platelets to resuspend the platelets. Furthermore, 20 mL of the CFT solution, 3 mL of the ACD solution, and 10 μL of 1 μg/μL PGI2 solution were added to the resuspended platelet solution. The platelet solution was centrifuged at 2,500 rpm for 10 minutes at room temperature with the swing rotor centrifuge.

After the supernatant of the centrifuged platelet solution was discarded, the CFT solution was added to precipitated platelets. After the platelets were resuspended, the number of platelets was counted with the multi-item automatic blood cell analyzer XE-2100 (Sysmex Corporation). The optical method (PLT-O) was used for counting. Based on the obtained number of the platelets, the resuspension solution was diluted with CFT solution so as to be 20×10$^4$ PLT/μL, obtaining sample solution. The sample solution was used for measuring the platelet aggregation ability.

Preparation of Culture Medium of Recombinant Cells

The culture media used in culturing the recombinant cells prepared in Example 3 were used for platelet aggregation ability test. 1-fold, 2-fold, 4-fold, 8-fold and 16-fold diluted culture media with the Opti-MEM medium were prepared as needed.

Measurement of Platelet Aggregation Ability

The platelet aggregation ability was measured using the platelet aggregation test apparatus, Hematracer 712 (MCM HEMA TRACER 712, LMS Co., Ltd.). After 11.1 μL of the culture medium used in culturing each of recombinant cells Nos. 1 and 2 was added to 100 μL of mouse washed platelet solution or 100 μL of human washed platelet solution, aggregation rates were measured over time for 10 minutes. The CFT solution, collagen solution adjusted to have a final concentration of 2 μg/ml collagen or rhodocytin solution having a desired concentration of purified snake venom rhodocytin was used as controls instead of the culture medium of each of recombinant cells Nos. 1 and 2, and was added to the platelet solution. The results are shown in FIGS. 4 and 5

Discussion of Results

Figure 4:
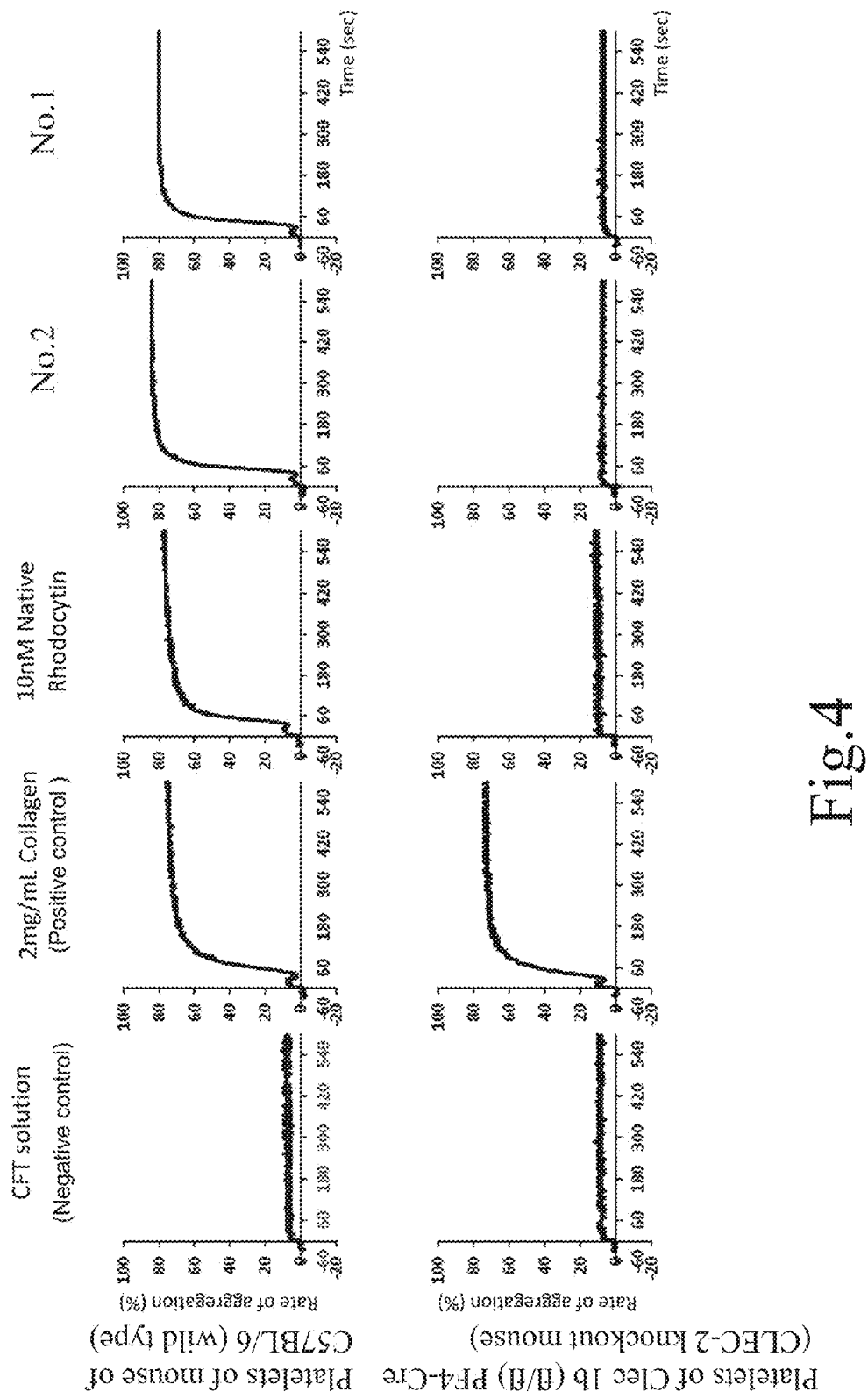
FIG. 4 shows experimental results for evaluating platelet aggregation ability in Example 4.
Figure 5:
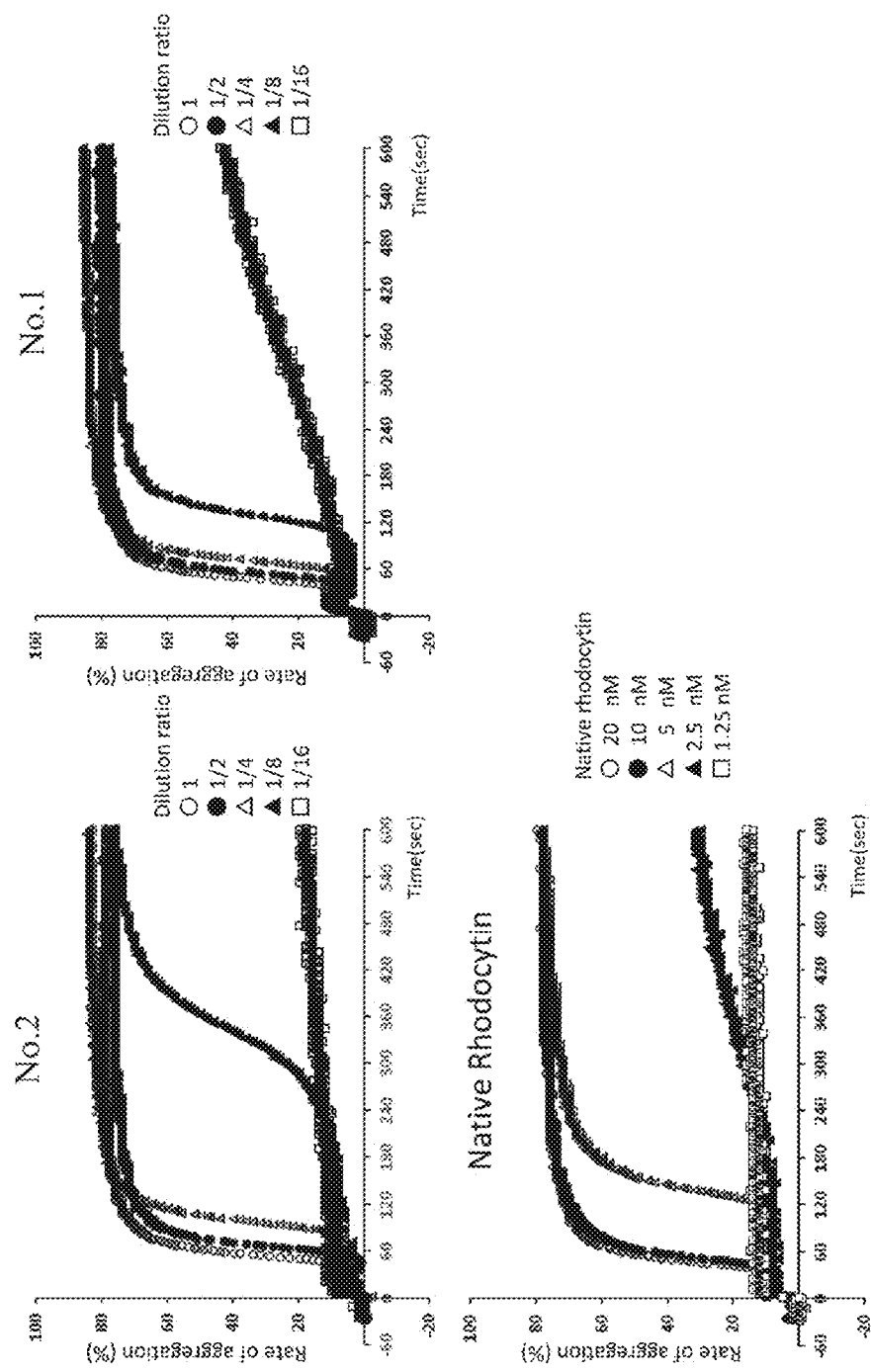
FIG. 5 shows experimental results for evaluating dose-dependency of human platelet aggregation in Example 4.

With reference to FIG. 4, the culture medium used in culturing of each recombinant cell was used without dilution. When the platelets derived from C57BL/6 (wild-type) mice were added to the culture medium used in culturing each of recombinant cells Nos. 1 and 2, the platelet aggregation appeared. On the other hand, when the platelets derived from CLEC-2 knockout mice were added to the culture medium used in culturing each of recombinant cells Nos. 1 and 2, platelet aggregation did not appear. It has already been reported that the collagen bound to the platelet surface receptors different from CLEC-2 binding receptor to stimulate the signaling pathways, causing the platelet aggregation.

The culture medium used in culturing each of recombinant cells Nos. 1 and 2 has the platelet aggregation ability against the platelets derived from C57BL/6 (wild-type) mice, and does not have the platelet aggregation ability against the platelets derived from CLEC-2 knockout mice. That is, recombinant cells Nos. 1 and 2 can produce the rhodocytin having the platelet activating ability.

With respect to FIG. 5, 1-fold, 2-fold, 4-fold, 8-fold and 16-fold diluted culture media of the culture media used in culturing each of recombinant cells Nos. 1 and 2 were prepared and used. It was found that the culture medium used in culturing recombinant cell No. 1 has higher platelet aggregation ability in a short time than the culture medium used in culturing recombinant cell No. 2 in comparison between the platelet aggregation abilities of the 8-fold diluted culture media of recombinant cells Nos. 1 and 2. On the basis of the combination of this result with the results of the western blotting in Example 3, it can be determined that the rhodocytin producing ability of recombinant cell No. 1 is higher than that of recombinant cell No. 2.

Example 5

Preparation of Genetic Recombination Vector Containing Mutant β Subunit Gene

Figure 6:
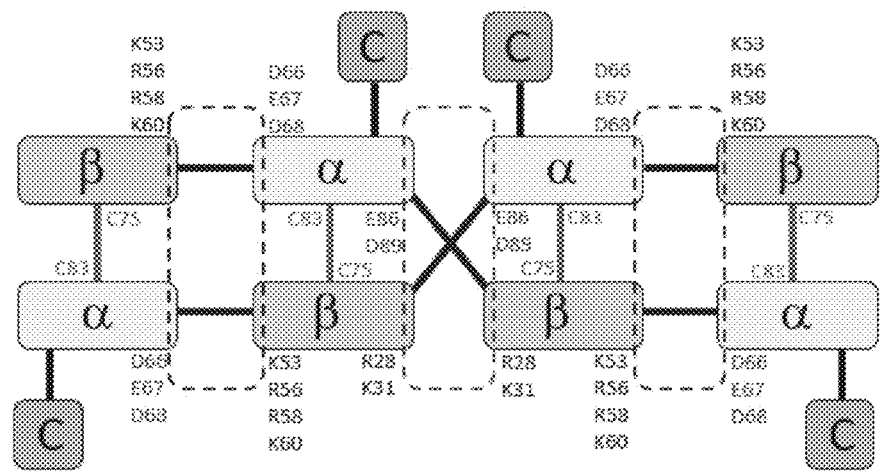
FIG. 6 schematically shows an octameric rhodocytin. Symbol "α" refers to a α subunit. Symbol "β" refers to a β subunit. Symbol "C" refers to CLEC-2. Amino acids and their positions in each subunit indicate the amino acids and their positions involved in an interaction between the subunits.

FIG. 6 shows amino acid residues and these positions for an interaction of the α subunit with the β subunit on the basis of simulation of a 3D structure of the wild-type rhodocytin. The amino acid residues to be mutated in an amino acid sequence of the β subunit and these positions were R28, K31, K53, R58, R56 and K60. Hereinafter, unless otherwise specified, the amino acid mutation refers to the mutation in the β subunit. One or more amino acid mutations were carried out by exchanging alanine. Six genetic recombination vectors were prepared by using [βS]-[β subunit]/pCMV described in Table 3, each vector having one of the following mutant β subunit genes: R28A and K31A (SEQ ID NO: 10), R56A (SEQ ID NO: 11), K53A and R56A (SEQ ID NO: 12), R58A and K60A (SEQ ID NO: 13), R28A, K31A, K53A and R56A (SEQ ID NO: 14) and R28A, K31A, R58A and K60A (SEQ ID NO: 15) (Table 6). The one or more amino acid mutations were carried out by executing the Overlap Extension PCR cloning method described in Example 1, with primers for substituting one or more amino acid residues at target position(s) with alanine.

TABLE 6

| Prepared recombinant vector | SEQ ID NO | Template | Primer 1 | Primer 2 |
|---|---|---|---|---|
| [β subunit] (R28A and K31A)/ | 10 | [βS-[β subunit]/ pCMV | 5'-TGGGCTGACG CCGAGGCGTTCT GCGCGCTGCAG CCCAAGCA-3' (SEQ ID NO: 30) | 5'-TGCTTGGGCT GCAGCGCGCAG AACGCCTCGGCG TCAGCCCA-3' (SEQ ID NO: 34) |
| [β subunit] (R56A)/pCMV | 11 | [βS-[β subunit]/ pCMV | 5'-GCGCTGACCA GGCCCAGGCTG AAGGCCAAC-3' (SEQ ID NO: 31) | 5'-GCCGACTTCG TGGTGGCGCTGA CCAGGCCC-3' (SEQ ID NO: 35) |
| [β subunit] (K53A and R56A)/pCMV | 12 | [βS-[β subunit]/ pCMV | 5'-GCGCTGACCG CGCCCAGGCTGA AGGCCAAC-3' (SEQ ID NO: 32) | 5'-GGGCGCGGTC AGCGCCACCACG AAGTCGGC-3' (SEQ ID NO: 36) |

TABLE 6-continued

| Prepared recombinant vector | SEQ ID NO | Template | Primer 1 | Primer 2 |
|---|---|---|---|---|
| [β subunit] (R58A and K60A)/pCMV | 13 | [βS-[β subunit]/ pCMV | 5'-CCCGCGCTGG CGGCCAACCTGG TGTGGATG-3' (SEQ ID NO: 33) | 5'-GGCCGCCAGC GCGGGCCTGGT CAGCTTCAC-3' (SEQ ID NO: 37) |
| [β subunit] (R28A, K31A, K53A and R56A)/pCMV | 14 | [βS-[β subunit] (R28A, and K31A,)/pCMV | 5'-GCGCTGACCG CGCCCAGGCTGA AGGCCAAC-3' (SEQ ID NO: 32) | 5'-GGGCGCGGTC AGCGCCACCACG AAGTCGGC-3' (SEQ ID NO: 36) |
| [β subunit] (R28A, K31A, R58A and R60A)/pCMV | 15 | [βS-[β subunit] (R28A, and K31A,)/pCMV | 5'-CCCGCGCTGG CGGCCAACCTGG TGTGGATG-3' (SEQ ID NO: 33) | 5'-GGCCGCCAGC GCGGGCCTGGT CAGCTTCAC-3' (SEQ ID NO: 37) |

Structural genes inserted into the prepared recombinant vector are listed in Table 7 and FIGS. 20A to 20H.

TABLE 7

| Inserted structural gene | SEQ ID NO |
|---|---|
| [βS]-[α subunit] | SEQ ID NO: 42 |
| [βS]-[β subunit] | SEQ ID NO: 2 |
| [βS]-[β subunit] (R28A and K31A) | SEQ ID NO: 43 |
| [βS]-[β subunit] (R56A) | SEQ ID NO: 44 |
| [βS]-[β subunit] (K53A and R56A) | SEQ ID NO: 45 |
| [βS]-[β subunit] (R58A and K60A) | SEQ ID NO: 46 |
| [βS]-[β subunit] (R28A, K31A, K53A and R56A) | SEQ ID NO: 47 |
| [βS]-[β subunit] (R28A, K31A, R58A and K60A) | SEQ ID NO: 48 |

Example 6

Confirmation of Protein Expression by Western Blotting Method

Each of vectors prepared in Example 5 and [βS]-[α subunit]/pCMV were transfected into the CHO cells according to Example 2. The produced CHO cells are listed in Table 8.

TABLE 8

| Recombinant cell number | Recombinant vector possessed by host cell | Host cell |
|---|---|---|
| 3 | [βS]-[α subunit]/pCMV [βS]-[β subunit] (R28A and K31A)/pCMV | CHO cell |
| 4 | [βS]-[α subunit]/pCMV [βS]-[β subunit] (R56A)/pCMV | CHO cell |
| 5 | [βS]-[α subunit]/pCMV [βS]-[β subunit] (K53A and R56A)/pCMV | CHO cell |
| 6 | [βS]-[α subunit]/pCMV [βS]-[β subunit](R58A and K60A)/pCMV | CHO cell |
| 7 | [βS]-[α subunit]/pCMV [βS]-[β subunit] (R28A, K31A, K53A and R56A)/pCMV | CHO cell |
| 8 | [βS]-[α subunit]/pCMV [βS]-[β subunit] (R28A, K31A, R58A and K60A)/pCMV | CHO cell |
| 9 | None | CHO cell |

Figure 7:
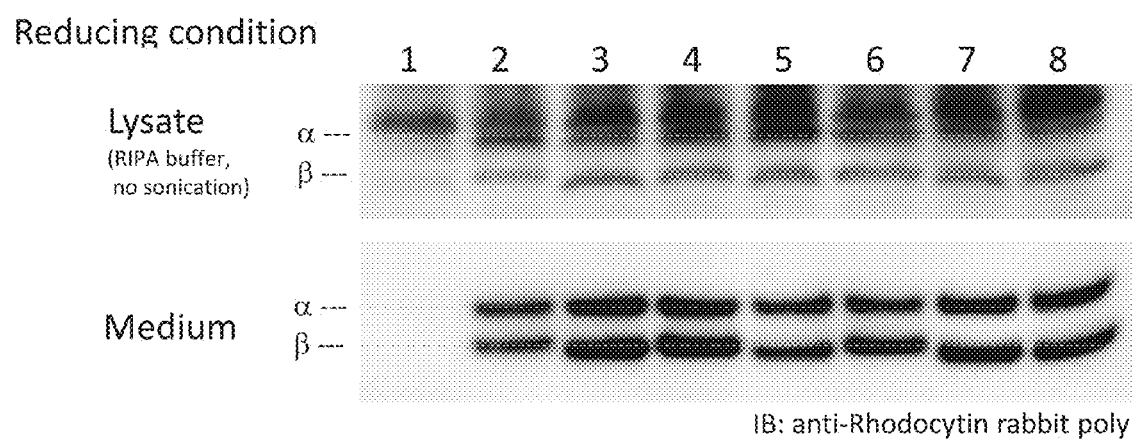
FIG. 7 shows results of Western blotting tests in Example 6.

According to Example 3, the expression of the rhodocytins was evaluated by using the CHO cells described in Tables 5 and 8 (except No. 2 recombinant cell). The results are shown in FIG. 7. The correspondence between lanes and recombinant cell numbers in FIG. 7 is shown in Table 9.

TABLE 9

| Lane | Recombinant cell number |
|---|---|
| 1 | 9 |
| 2 | 1 |
| 3 | 5 |
| 4 | 4 |
| 5 | 6 |
| 6 | 3 |
| 7 | 7 |
| 8 | 8 |

As shown in FIG. 7, it was revealed that the CHO cells listed in Table 8 can secret α and β subunits in the medium, and that the β subunits were secreted to the medium to the same extent as the α subunits.

Example 7

Evaluation of Platelet Aggregation Ability of Mutant Rhodocytins

Figures 8A, 8B, 8C, 8D:
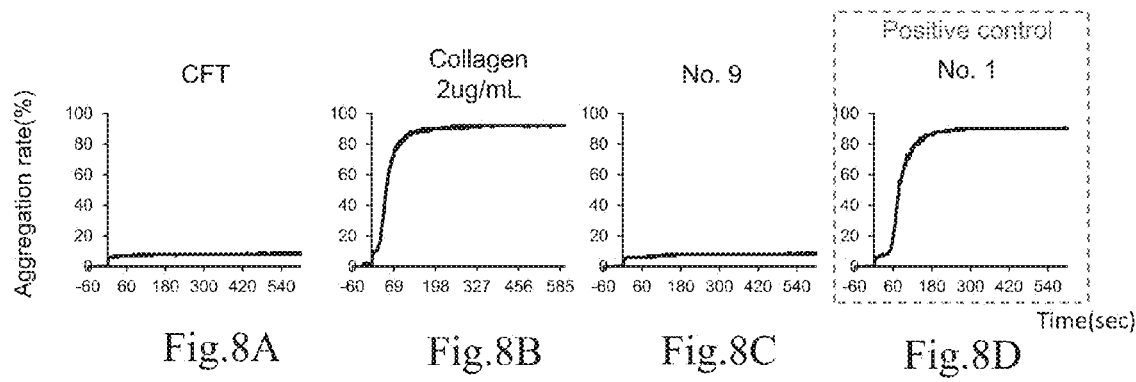
FIGS. 8A to 8J show experimental results for evaluating platelet aggregation ability of mutant rhodocytins in Example 7.
Figures 8E, 8F, 8G, 8H:
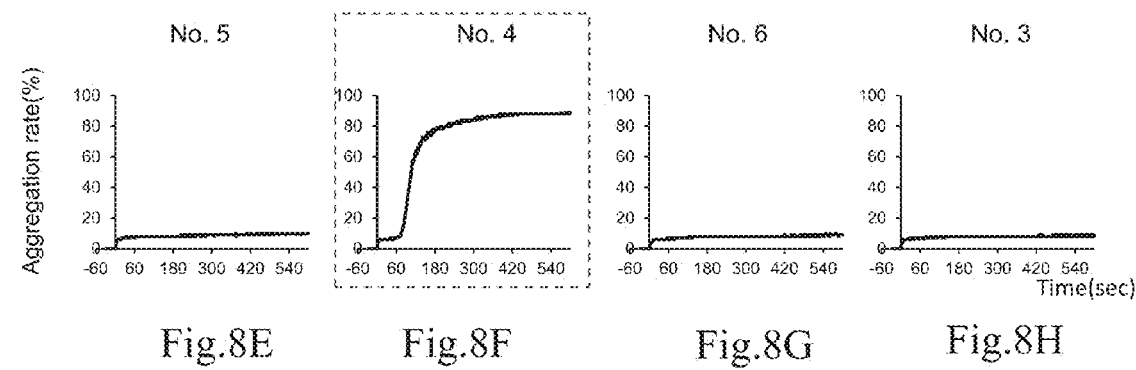
Figures 8I, 8J:
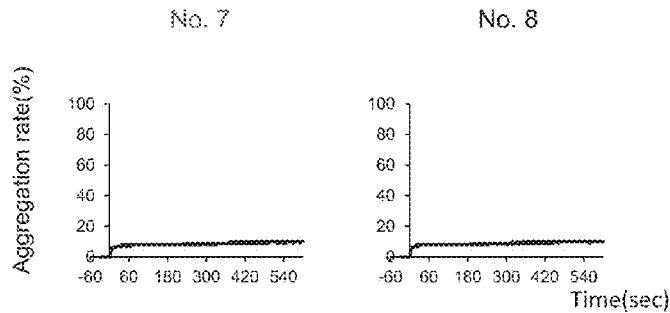

It was determined whether each of the rhodocytins derived from the CHO cells used in Example 6 had the platelet aggregation ability. The human platelets were used, and the experimental method in accordance with Example 4 was used. The results are shown in FIGS. 8A to 8J. It was shown that the rhodocytin containing β subunit (R56A) derived from cell No. 4 (FIG. 8F) had the platelet aggregation ability similar to that derived from cell No. 1 being a positive control (FIG. 8D). Neither the rhodocytin derived from cell No. 5 (K53A and R56A) (FIG. 8E), the rhodocytin derived from cell No. 6 (R58A and K60A) (FIG. 8G), the rhodocytin derived from cell No. 3 (R28A and K31A) (FIG. 8H), the rhodocytin derived from cell No. 7 (R28A, K31A, K53A and R56A) (FIG. 8I) nor the rhodocytin derived from cell No. 8 (R28A, K31A, R58A and K60A) (FIG. 8J) had any platelet aggregation ability.

Example 8

Test for Suppressing Platelet Aggregation Caused by Wild-Type Rhodocytin Using Mutant Rhodocytins It was examined whether mutant rhodocytins inhibited the platelet aggregation caused by the platelet aggregating substance. In this example, the wild-type rhodocytin was used as the platelet aggregating substance. The human platelets prepared in accordance with Example 4 were used.

The platelet aggregation ability was measured using the platelet aggregation test apparatus, Hematracer 712 (MCM HEMA TRACER 712, LMS Co., Ltd.). 20 µL of the human platelet solution was mixed with 80 µL of the respective recombinant cell culture media, obtaining mixed solutions. The mixed solutions were incubated for 5 minutes. After 11.1 µL of the culture medium used in culturing CHO cell No. 1 was added to the respective mixed solutions, aggregation rates were measured over time for 10 minutes.

Figure 9H:
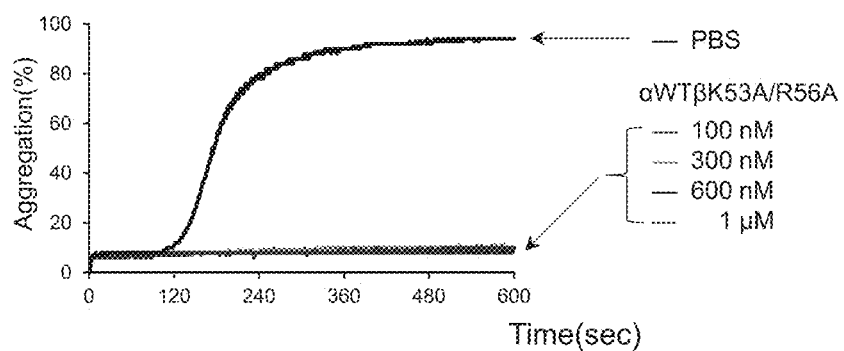
FIGS. 9H to 9I show experimental results for inhibition tests of platelet aggregation caused by collagen, using mutant rhodocytin derived from cell No. 5 (K53A and R56A).
Figure 9I:
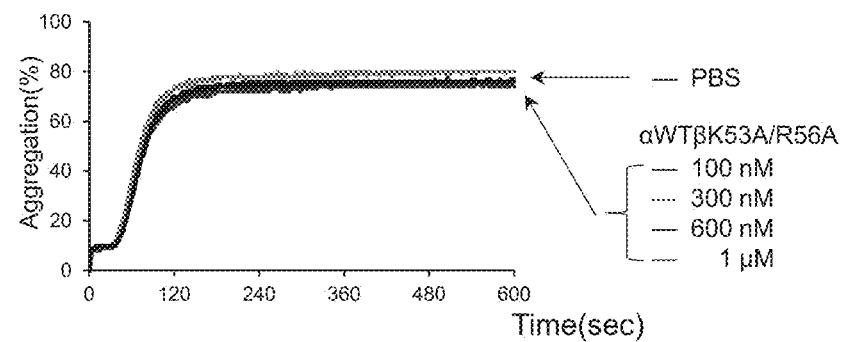

Results are shown in FIG. 9. FIG. 9A shows the result in case where 80 µL of the culture medium used in culturing CHO cell No. 1 and 11.1 µL of the culture medium used in culturing CHO cell No. 1 were used, and FIG. 9B shows the result in case where 80 µL of the culture medium used in culturing CHO cell No. 9 and 11.1 µL of the culture medium used in culturing CHO cell No. 1 were used The rhodocytin derived from cell No. 5 (K53A and R56A) and the rhodocytin derived from cell No. 6 (R58A and K60A) completely inhibited the platelet aggregation caused by the wild-type rhodocytin (FIGS. 9C and 9D). Since the rhodocytin derived from cell No. 7 (R28A, K31A, K53A and R56A) and the rhodocytin derived from cell No. 8 (R28A, K31A, R58A and K60A) delayed the platelet aggregation caused by the wild-type rhodocytin (FIGS. 9F and 9G). It was found that these rhodocytins had partial platelet aggregation inhibiting ability (FIGS. 9F and 9G). Furthermore, it was evaluated that whether the mutant rhodocytin inhibited GPVI-dependent platelet aggregation. In this experiment, the rhodocytin derived from cell No. 5 (K53A and R56A) and collagen (control) were used. Collagen is known to be an agonist to induce GPVI-dependent platelet aggregation. Results are shown in FIGS. 9H and 9I. The rhodocytin derived from cell No. 5 (K53A and R56A) completely inhibited the platelet aggregation caused by the wild-type rhodocytin (FIG. 9H), but did not inhibit the GPVI-dependent platelet aggregation caused by the collagen (FIG. 9I). These results revealed that the rhodocytin derived from cell No. 5 (K53A and R56A) specifically inhibited the CLEC-2-dependent platelet aggregation.

Example 9

Subunit Structures of Wild-Type Rhodocytin

The subunit structures of the wild-type rhodocytin derived from cell No. 1 and the mutant rhodocytin derived from cell No. 5 (K53A and R56A) were analyzed by using SDS-PAGE (density gradient: 4 to 12%) and BN-PAGE (density gradient: 4 to 16%). Each of the culture media used in culturing cells Nos. 1 and 5 was centrifuged at 3,000 rpm for 10 minutes. After removing the suspended cells and matters from the centrifuged culture media, and each of the supernatants was obtained. Furthermore, each of the obtained supernatants was passed through a 0.45 µm filter to remove solid matters such as precipitates, obtaining samples for purification. Purification was carried out by three steps of including gel filtration chromatography, ion exchange chromatography, and desalination. HiPrep 26/60 Sephacryl S-200 HR column (column capacity: 320 mL) (manufactured by GE) was used for the gel filtration chromatography. The buffer including 50 mM Tris-HCl/0.1 M NaCl at pH 8.0 was used and flow rate was set to 1.3 mL/min. Eluted samples were collected as 5 mL/fraction. The wild-type rhodocytin containing fraction and the mutant rhodocytin containing fraction were selected based on the platelet aggregation ability or the platelet aggregation inhibiting ability of the eluted samples as indicators. For the subsequent ion exchange chromatography, three-connected HiTrap Q HPs (5 mL volume×3) (manufactured by GE) was used. Using the same buffer as the buffer used to the gel filtration chromatography, the target protein (i.e., rhodocytin) was eluted by linearly increasing NaCl concentration to 0.1 to 0.5 M gradually. Flow rate was set to 5 mL/min. Electrical conductivity (mS/cm) at elution of the target proteins: wild-type rhodocytin and the mutant rhodocytin derived from cell No. 5 (K53A and R56A) were 35-36 mS/cm. Further, in order to perform the desalination process and the PBS exchange process, four-connected HiTrap Desalting columns (5 mL column volume×4) (manufactured by GE) and desalting/spontaneous drop/centrifugal separation column PD-10 (manufactured by GE) for buffer exchange were used. Each of low concentration samples was concentrated using an Amicon Ultra 15 centrifugal filter unit (for 10 kDa or 30 kDa) (manufactured by Merck). Protein concentrations in the samples were measured by absorptiometry. For SDS-PAGE, an amount of each sample to be applied was 5 µg. For BN-PAGE, an amount of each sample to be applied was 10 µg. Gels after electrophoresis were stained with CBB.

Figure 10A:
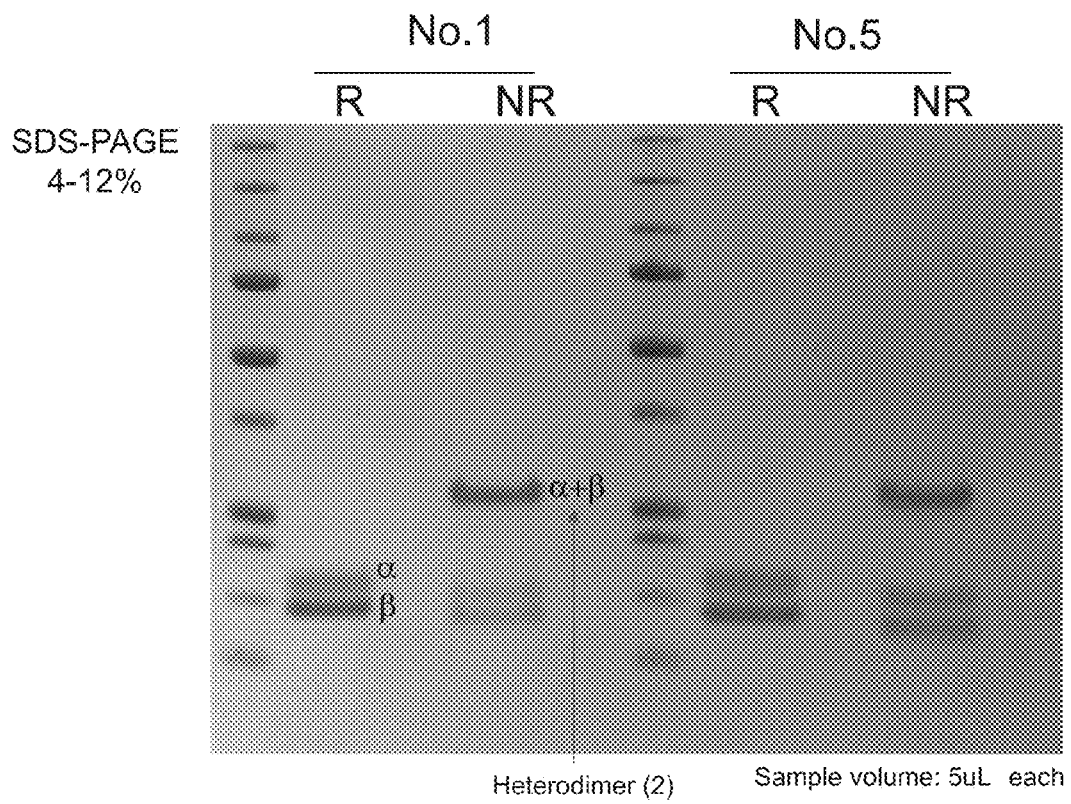
FIGS. 10A and 10B show photographs for electrophoresis performed to evaluate subunit structures of wild-type rhodocytin or mutant rhodocytin derived from cell No. 5 (K53A and R56A). No. 1 refers to the wild-type rhodocytin. No. 5 refers to mutant rhodocytin (K53A and R56A).

A result for SDS-PAGE (4 to 12%) is shown in FIG. 10A. As shown in FIG. 10A, two bands were detected in each of cells No. 1 (wild-type) and No. 5 (K53A and R56A) under reductive condition (R). Based on length of amino acid sequences, it was revealed that one band with higher molecular weight corresponds to the α subunit and another band with lower molecular weight corresponds to the β subunit. Under non-reductive condition (NR), a heterodimer composed of the α subunit and the β subunit was detected in each of cells No. 1 (K53A) and No. 5 (R56A). These results revealed that both wild-type rhodocytin and mutant rhodocytin form multimers through disulfide bonds.

Figure 10B:
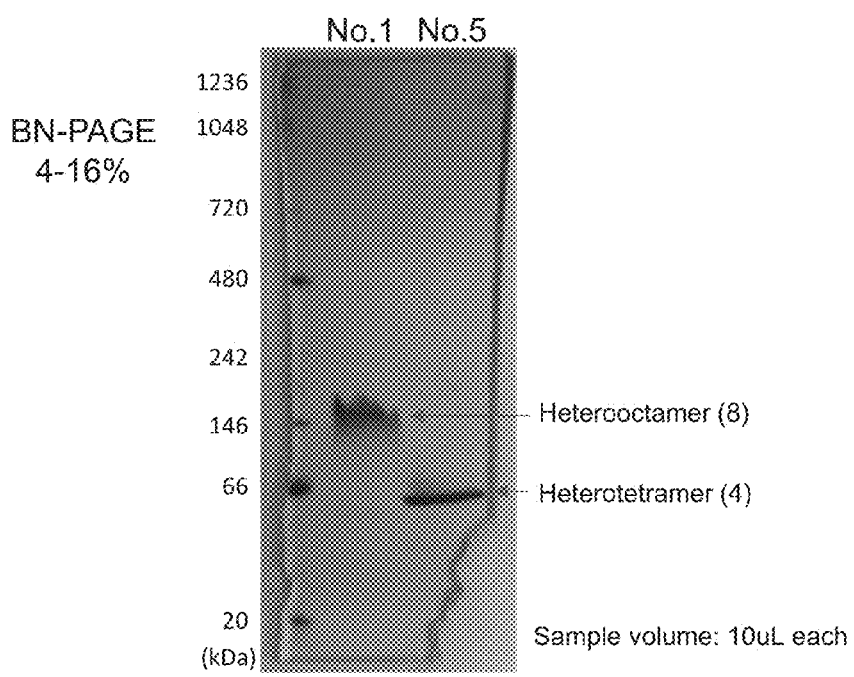

A result for BN-PAGE (4 to 16%) is shown in FIG. 10B. As shown in FIG. 10B, in cell No. 5 (K53A and R56A), a band appeared at a position indicating a heterotetramer, while in cell No. 1, a band appeared at a position indicating a heterooctamer. Until now, the wild-type rhodocytin has been reported to be composed of a heterotetramer, but in this experiment it was found that the wild-type rhodocytin was composed of a heterooctamer.

Figure 11:
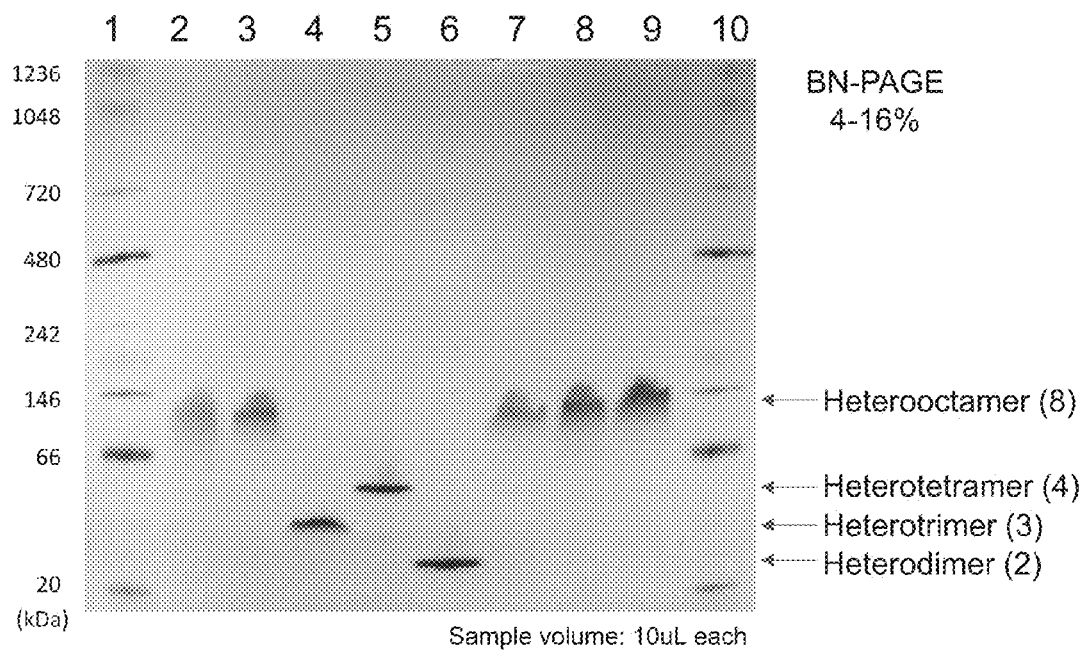
FIG. 11 shows a photograph for electrophoresis performed to evaluate subunit structures of wild-type rhodocytin or mutant rhodocytins.

In addition, BN-PAGE was performed on the mutant rhodocytins with other amino acid mutations and the native rhodocytin isolated and purified from snake venom. Purification was performed by using the above-mentioned method. Electric conductivities (mS/cm) at elution of target proteins are as follows: the mutant rhodocytin derived from the CHO cells containing the recombinant vector containing the structural gene of the mutant α subunit (D4A) in which the fourth D were substituted with A was 35-36 mS/cm; and the mutant rhodocytins derived from cells No. 3 (R28A and K31A) and No. 7 (R28A, K31A, K53A and R56A) were 27-28 mS/cm. In the mutant rhodocytin derived from cell No. 3 (R28A and K31A), a band appeared at a position indicating a heterotrimer (lane 4 in FIG. 11). In the mutant rhodocytin derived from cell No. 5 (K53A and R56A), a band appeared at a position indicating a heterotetramer (lane 5 in FIG. 11). In the mutant rhodocytin derived from cell No. 7 (R28A, K31A, K53A and R56A), a band appeared at position indicating a heterodimer (lane 6 in FIG. 11). In the native rhodocytin and all wild-type rhodocytins, bands appeared at positions where molecular weight of these rhodocytins were higher than that of the mutant rhodocytin derived from cell No. 5 (K53A and R56A), indicating a heterotetramer (lanes 2, 3, 8 and 9 and FIG. 11). Lane 7 corresponds to the mutant rhodocytin derived from the CHO cells containing the recombinant vector containing the gene of the mutant type α subunit having the amino acid corresponding to position 4 being a substitution of D with A. In lane 7, a band appeared at a position indicating a heterooctamer, like the wild-type rhodocytin. As a result, the wild-type rhodocytin was found to be an octamer. It was also found that the number of subunits of the mutant rhodocytin varies depending on the position of amino acid mutation. Table 10 lists results shown in FIGS. 10 and 11.

TABLE 10

| β subunit | Platelet aggregation | CLEC-2 binding | Inhibition of platelet aggregation by rhodocytin | Multimeric complex (BN-PAGE) |
|---|---|---|---|---|
| Wild-type | Aggregated | Bound | None | 8 |
| K53A, R56A | None | Bound | Inhibited | 4 |
| R28A, K31A | None | Bound | None | 3 |
| R28A, K31A, K53A, R56A | None | Bound | Partially inhibited | 2 |

Example 10

Test for Inhibiting Platelet Aggregation Caused by Wild-Type Rhodocytin Using Various Concentrations of Mutant Rhodocytins The platelet aggregation ability was evaluated by using the mutant rhodocytins at various concentrations. The experiment was carried out based on Example 8. The concentration of the wild-type rhodocytin was 10 nM. Results are shown in FIG. 12.

Figure 12A:
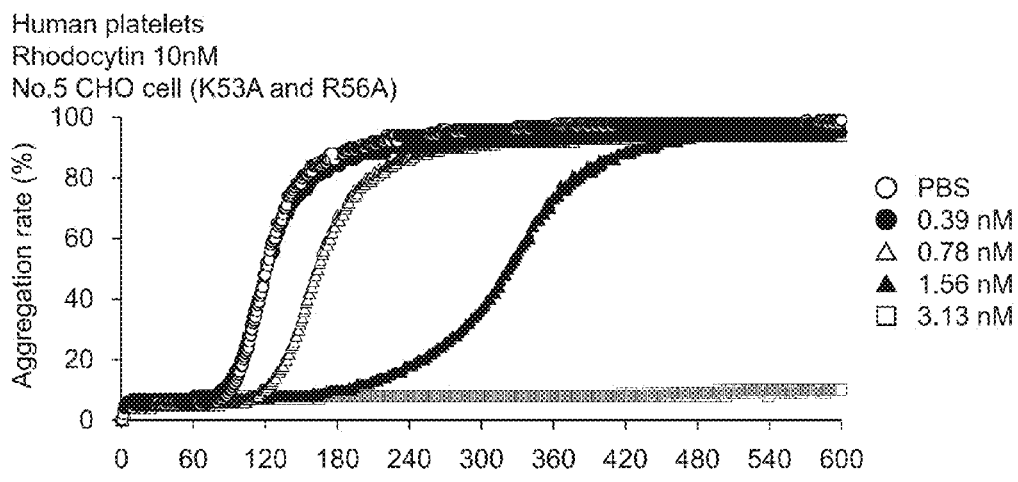
FIGS. 12A to 12C show experimental results for suppression tests of platelet aggregation caused by wild-type rhodocytin, using various concentrations of mutant rhodocytins.
Figure 12B:
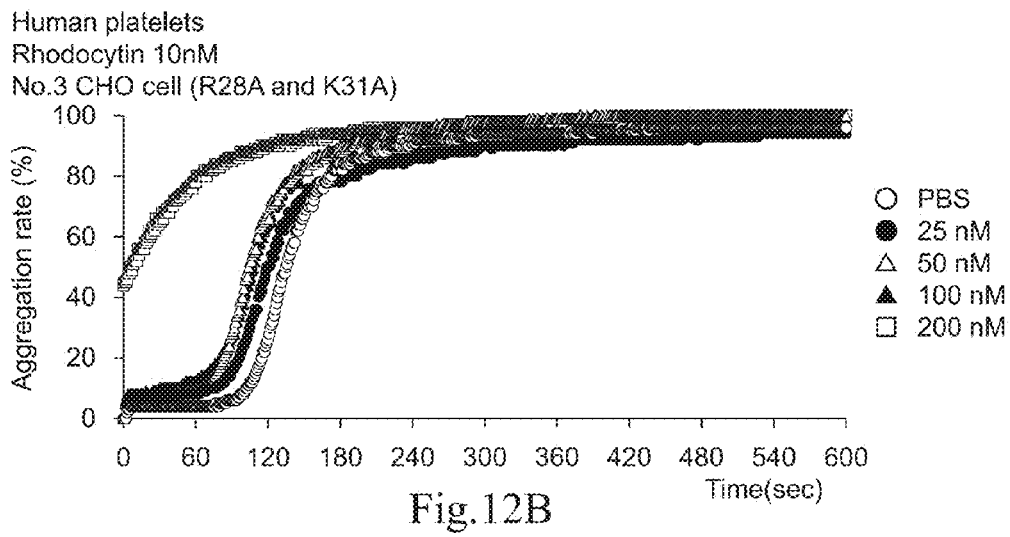
Figure 12C:
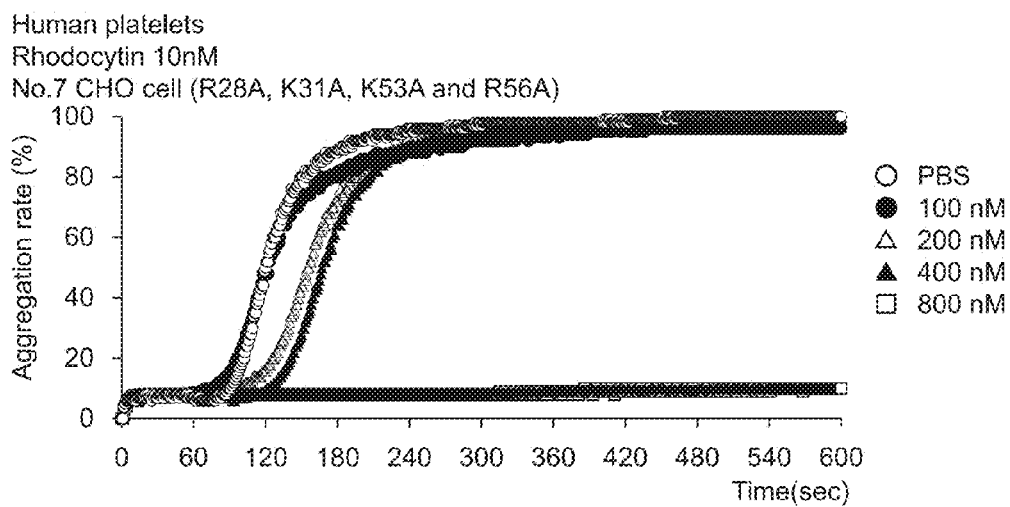

The mutant rhodocytin derived from cell No. 5 (K53A and R56A) had an inhibitory effect at a concentration of at least 1.5625 nM and completely inhibited the platelet aggregation caused by the wild-type rhodocytin at a concentration of at least 3.125 nM (FIG. 12A). The mutant rhodocytin derived from cell No. 3 (R28A and K31A) did not inhibit the platelet aggregation caused by the wild-type rhodocytin (FIG. 12B). The mutant rhodocytin derived from cell No. 7 (R28A, K31A, K53A and R56A) had a suppressive effect at a concentration of 200 to 400 nM, and completely inhibited the platelet aggregation caused by the wild-type rhodocytin at a concentration of at least 800 nM (FIG. 12C).

Figure 13A:
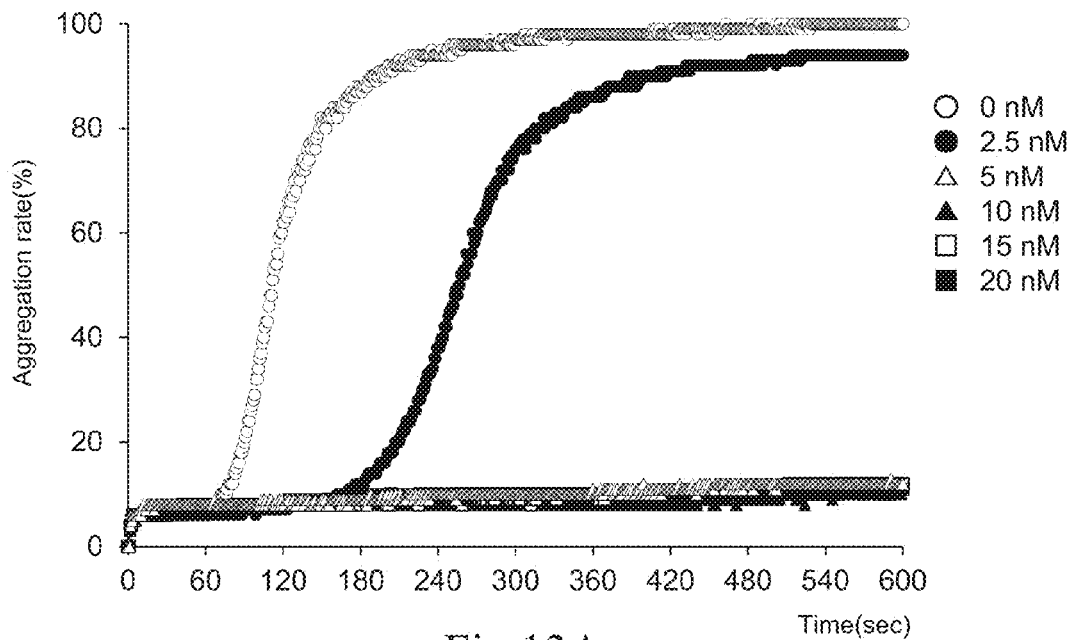
FIGS. 13A and 13B show experimental results of suppression tests of platelet aggregation caused by wild-type rhodocytin, using various concentrations of mutant rhodocytin derived from cell No. 5 (K53A and R56A).
Figure 13B:
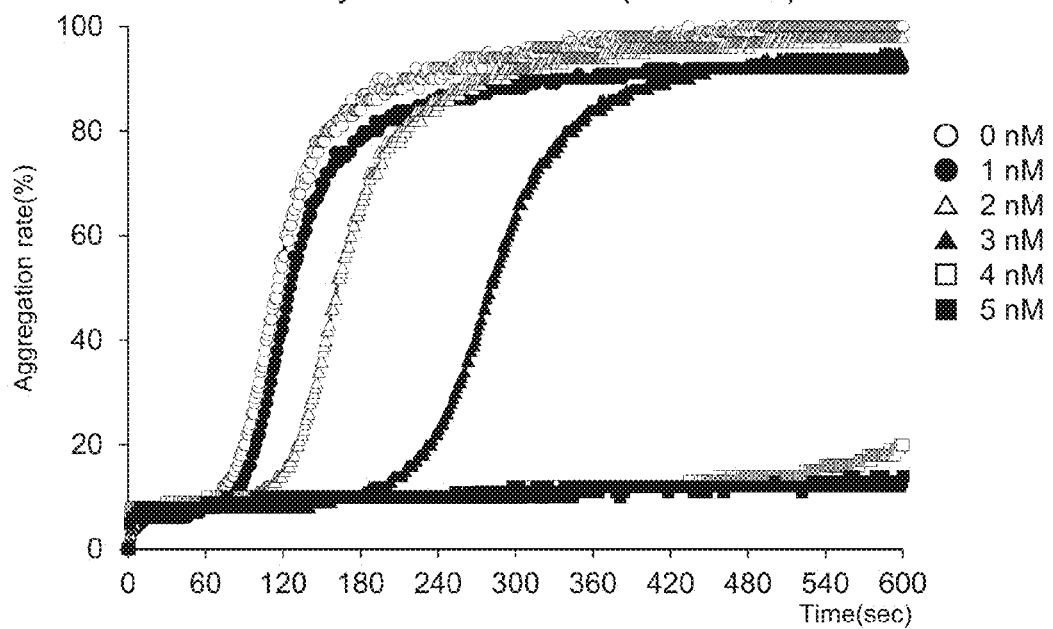

Furthermore, the platelet aggregation ability was evaluated by using the mutant rhodocytin derived from cell No. 5 (K53A and R56A) at 0, 1, 2, 2.5, 3, 4, 5, 10, 15 and 20 nM. As shown in FIG. 13, the mutant rhodocytin derived from cell No. 5 (K53A and R56A) completely inhibited the platelet aggregation caused by the wild-type rhodocytin at a concentration of 4 nM or more.

Example 11

Determination of Binding to Human CLEC-2 by Flow Cytometer

It was evaluated that whether the mutant rhodocytins inhibited the interaction between CLEC-2 and podoplanin (PDPN).

As a human CLEC-2 expressing cell, T-REx human CLEC-2 expressing 293 cells (J Biol Chem. 2007 Sep. 7; 282 (36): 25993-26001) capable of the expression induced by doxycycline (Dox) were used.

The T-REx Human CLEC-2 expressing 293 cells were cultured in the serum DMEM medium containing a final concentration of 10 μg/mL doxycycline until an occupancy rate with respect to 15 cm diameter culture dish was reached to 100%. The culture medium was discarded and the cells were washed once with 1×PBS. 2 ml of trypsin-EDTA-Na solution was added to each culture dish. After the solution spread throughout each culture dish, the trypsin-EDTA-Na solutions were collected, and the culture dishes were incubated at 37° C. for 2 minutes. After the incubation, the CHO cells were suspended in the solution containing 20 mL of DMEM and 0.2 mL of P/S solution, the suspensions were collected in each 50 mL Falcon tube, the tubes were centrifuged at 1,000 rpm for 5 minutes at room temperature. After discarding the supernatant in each tube, the T-REx human CLEC-2 expressing 293 cells were adjusted to $5 \times 10^6$ cells/mL by using the serum DMEM.

According to Example 3, the culture media derived from cell No. 1 (wild-type), cell No. 5 (K53A and R56A), cell No. 3 (R28A and K31A) and cell No. 7 (R28A, K31A, K53A and R56A) were used as samples. The native rhodocytin means a rhodocytin isolated from snake venom. The negative control was PBS. Each sample was adjusted so that respective concentrations of the rhodocytins in each samples were 1 μM, 100 nM and 10 nM.

A human IgG Fc was fused to PDPN to produce a PDPN-human Fc fusion protein. The human IgG Fc was used as a negative control. The amount of each IgG Fc used in the experiment was 0.5 μg.

The samples containing various concentrations (1 μM, 100 nM and 10 nM) of rhodocytins and 0.5 μg of the PDPN-human Fc fusion protein were simultaneously added to and mixed with 50 μL of the respective suspensions regarding the T-REx human CLEC-2 expressing 293 cells. After the incubation for 30 minutes at room temperature, 400 μL of 1×PBS was added to the incubated suspensions for wash, followed by centrifugation at 3,000 rpm for 5 minutes at room temperature. The supernatants were discarded to collect the 293 T-REx human CLEC-2 expressing cells. Anti-human IgG antibodies Alexa 488 (Molecular Probes) were added to the collected T-REx human CLEC-2 expressing 293 cells, followed by incubation at room temperature for 30 minutes to prepare samples. For detection, Accuri C6 Flow Cytometer (Becton, Dickinson and Company) was used.

As a negative control, the binding to the human CLEC-2 was examined in the same manner as above, except the use of the mixture of 50 μL of the suspension of the T-REx human CLEC-2 expressing cells, 50 μL of PBS and the human IgG Fc. In addition, as a positive control, the binding to the human CLEC-2 was examined in the same manner as above, except the use of the mixture of 50 μL of the suspension of the T-REx human CLEC-2 expressing cells, 50 μL of PBS and the PDPN-human Fc fusion protein.

Figure 14:
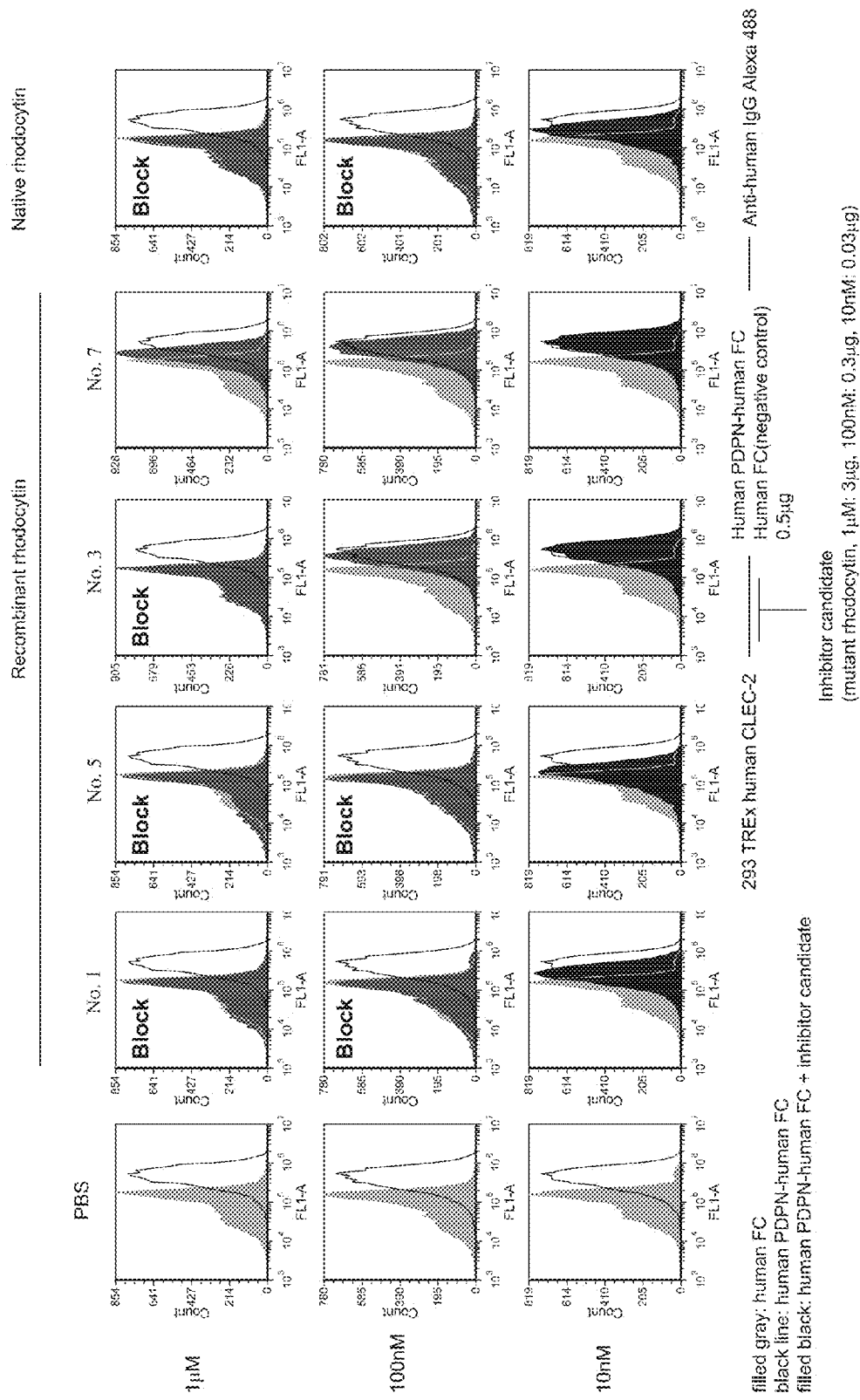
FIG. 14 shows results of flow cytometry for evaluating inhibitory effects of wild-type rhodocytin or mutant rhodocytins on the binding between human CLEC-2 and podoplanin.

Results are shown in FIG. 14. It was revealed that since the regions for the culture medium of cell No. 1 (wild-type), the culture medium of cell No. 5 (K53A and R56A) and the native rhodocytin (black region in FIG. 14) were overlapped with the region of the negative control at concentrations of 1 μM and 100 μM (gray region in FIG. 14), the mutant rhodocytin derived from cell No. 5 (K53A and R56A) was bound to the human CLEC-2 and inhibited the binding between the human CLEC-2 and podoplanin. It was also revealed that since the region of cell No. 3 (R28A and K31A) was overlapped with the region of the negative control (gray region in FIG. 14) at a concentration of 1 μM, the mutant rhodocytin derived from cell No. 5 (K53A and R56A) was bound to the human CLEC-2 and inhibited the binding between the human CLEC-2 and podoplanin. The mutant rhodocytin derived from cell No. 7 (R28A, K31A,

25

K53A and R56A) at a concentration of 1 μM or less did not inhibit the binding between the human CLEC-2 and podoplanin.

Example 12

Suppression of Cancer Cell-Induced Platelet Aggregation by Mutant Rhodocytins

It was evaluated that whether the mutant rhodocytins inhibited cancer cell-induced platelet aggregation.

As the cancer cells, human podoplanin (hPod)-expressing CHO cells (hPod-CHO) were used (1×10$^6$ cells/μL and 5×10$^6$ cells/μL). The human platelets were adjusted to 100× 10$^4$ PLT/μL based on Example 4. 100 nM and 600 nM of the wild-type rhodocytins derived from cell No. 5 (K53A and R56A) were used as samples. PBS was used as a negative control.

Figure 15A:
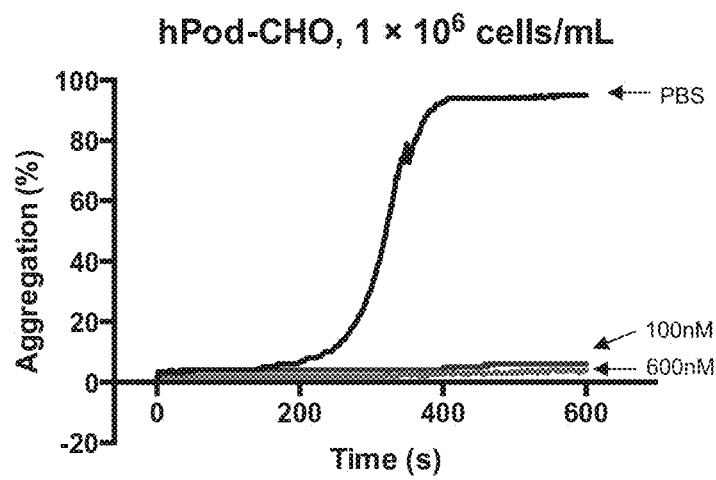
FIGS. 15A and 15B show experimental results of suppression tests of cancer cell-induced platelet aggregation, using mutant rhodocytins.
Figure 15B:
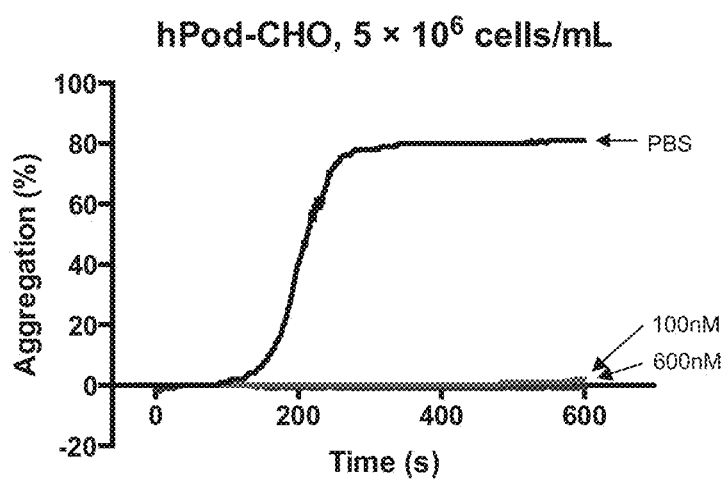

Results are shown in FIG. 15. In both of 1×10$^6$ cells/μL and 5×10$^6$ cells/μL of hPod-CHO, 100 nM of the wild-type rhodocytin derived from cell No. 5 (K53A and R56A) inhibited hPod-CHO induced human platelet aggregation.

Example 13

Suppression of Hematogenous Metastasis of Cancer Cells Using Mutant Rhodocytin

It was evaluated that whether the mutant rhodocytins inhibited the hematogenous metastasis of the cancer cells.

As the cancer cells, the human podoplanin (hPod)-expressing CHO cells (hPod-CHO) were used. The mutant rhodocytin (K53A and R56A) at a final concentration of 1 μM was used as a sample. PBS was used as a negative control. 7 week-old female BALB/c nude (nu/nu) mice were used (n=5 in each group). The mutant rhodocytin (K53A and R56A) at a final concentration of 1 μM or PBS along with 1×10$^6$ cells/μL of hPod-CHO was administered to orbit in each mouse to start the experiment. The mutant rhodocytin (K53A and R56A) or PBS was administered every other day. The experiment was carried out for 14 days. After the completion of the experiment, the mice were sacrificed, followed by collecting lungs, blood and lung nodules of the mice.

Figure 16:
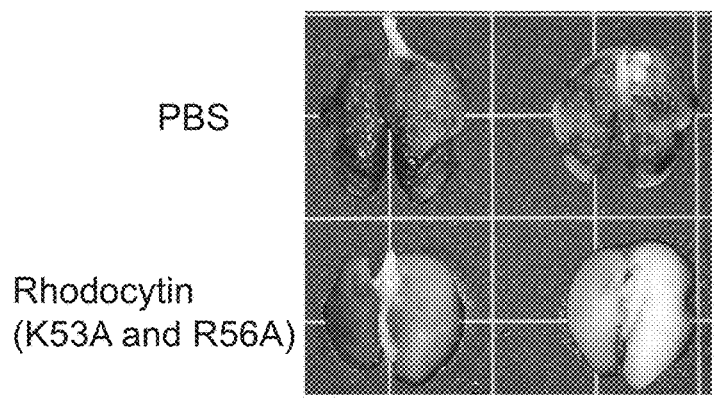
FIG. 16 shows a photograph of the lungs in mice, showing results of suppression of hematogenous metastasis of cancer cells, using mutant rhodocytin.

Results are shown in FIGS. 16 to 19. As shown in the photograph of FIG. 16, it became visually apparent that in the negative control (PBS), the cancer was metastasized to the lung while the mutant rhodocytin (K53A and R56A) suppressed the metastasis of the cancer.

Figures 17A, 17B, 17C:
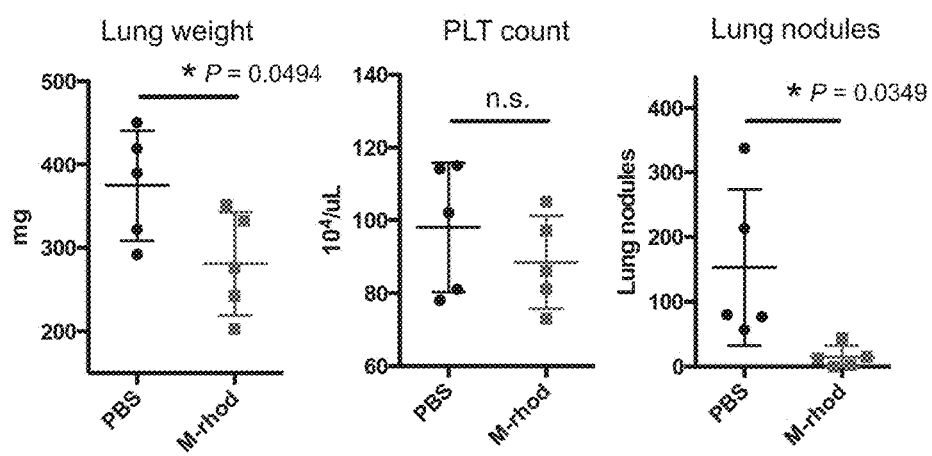
FIG. 17A shows a graph for comparison of lung weight of control mice with lung weight of mice administered with a mutant rhodocytin.
FIG. 17B shows a graph for comparison of the number of platelet counts of control mice with the number of platelet counts of mice administered with mutant rhodocytin.
FIG. 17C shows a graph for comparison of the number of lung nodules with the number of lung nodules of mice administered with mutant rhodocytin.

FIG. 17A shows the comparison of the lung weight in each mouse administered with the mutant rhodocytin (K53A and R56A) with that in each mouse administered with PBS. The lung weight in each mouse administered with PBS increased significantly with the metastasis of the cancer compared to that in each mouse administered with the mutant rhodocytin (K53A and R56A). FIG. 17B shows the comparison of the number of platelets contained in blood of each mouse administered with the mutant rhodocytin (K53A and R56A) with the number of platelets contained in blood of each mouse administered with PBS. There was no significant difference in the number of platelets in both. FIG. 17C shows the comparison of the number of the lung nodules in each mouse administered with the mutant rhodocytin (K53A and R56A) and the number of the lung nodules in each mouse administered with PBS. The mice administered with PBS significantly increased the number of the lung nodules compared to the mice administered with the mutant rhodocytin (K53A and R56A).

Figures 18A, 18B:
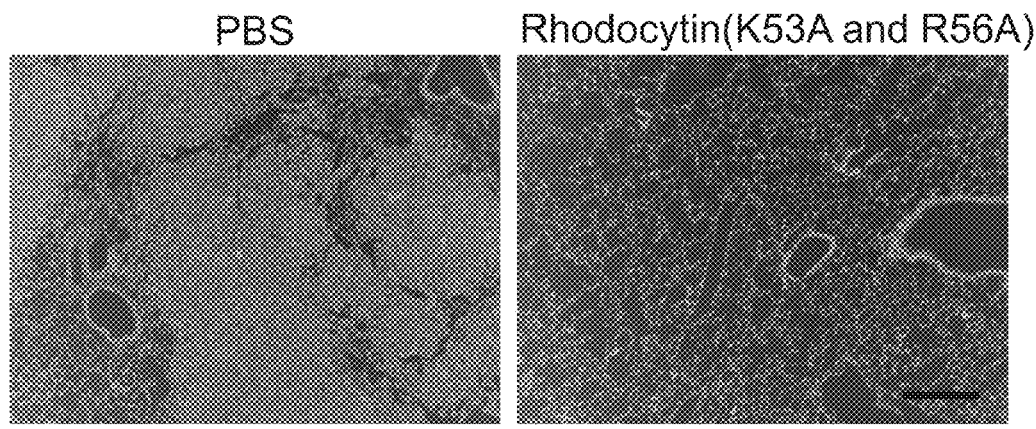
FIGS. 18A and 18B show photographs of hematoxylin and eosin (HE) staining of mouse lungs in an inhibition test for hematogenous metastasis of cancer cells.
Figure 19:
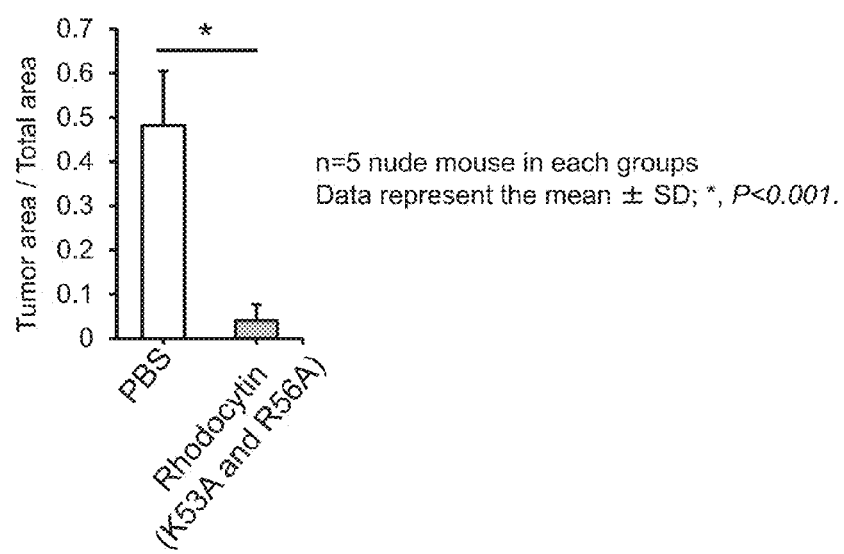
FIG. 19 shows a graph showing ratios of tumor region per whole lung region in mice in an inhibition test for hematogenous metastasis of cancer cells.

FIG. 18 is the photographs of hematoxylin and eosin (HE) staining of lung tissue in the mouse administered with the mutant rhodocytin (K53A and R56A) and the HE staining lung tissue in the mouse administered with PBS. The lung tissue of the mouse administered with PBS was stained as a whole (FIG. 18A), whereas the lung tissue of the mouse administered with the mutant rhodocytin (K53A and R56A) was not stained at all (FIG. 18B). FIG. 19 shows graphically the ratio of tumor area per total lung area. As is apparent from FIG. 19, it was revealed that the mutant rhodocytin (K53A and R56A) significantly inhibited the tumor metastasis.

What is claimed is:

1. A mutant rhodocytin lacking platelet aggregation ability, wherein the mutant rhodocytin comprises 2, 3 or 4 subunits.

2. The mutant rhodocytin according to claim 1, wherein at least one of the subunits is a mutant subunit having one or more amino acid residues different from the wild-type subunit so that the number of the subunits in the mutant rhodocytin is different from the number of subunits in the wild-type rhodocytin.

3. The mutant rhodocytin according to claim 2, wherein the mutant subunit comprises a mutant β subunit having one or more amino acids different from wild-type β subunit.

4. The mutant rhodocytin according to claim 3, wherein the mutant β subunit has amino acid mutations at one or more positions selected from the group consisting of positions [K53 and R56], [R58 and K60] and [R28 and K31] of the wild-type β subunit.

5. The mutant rhodocytin according to claim 3, wherein the mutant β subunit has amino acid mutations at either positions [K53 and R56] or positions [R58 and K60] of the wild-type β subunit.

6. A structural gene encoding the subunit according to claim 2.

7. A vector comprising the structural gene according to claim 6.

8. A transformant comprising the vector according to claim 7.

9. A mutant rhodocytin comprising a mutant β subunit having amino acid mutations at one or more positions selected from the group consisting of positions [K53 and R56], [R58 and K60] and [R28 and K31] of β subunit of wild-type rhodocytin.

10. A mutant rhodocytin comprising a mutant type β subunit having amino acid mutations at either positions [K53 and R56] or [R58 and K60] of β subunit of wild-type rhodocytin.

11. A pharmaceutical composition comprising the mutant rhodocytin according to claim 1.

12. A method for inhibiting platelet aggregation by a platelet aggregating substance, comprising administering the pharmaceutical composition according claim 11 to a subject in need thereof.

* * * * *